(12) United States Patent
Lee

(10) Patent No.: US 10,555,910 B2
(45) Date of Patent: Feb. 11, 2020

(54) OLIGONUCLEOTIDE LIPID NANOPARTICLE COMPOSITIONS, METHODS OF MAKING AND METHODS OF USING THE SAME

(71) Applicant: Ohio State Innovation Foundation, Columbus, OH (US)

(72) Inventor: Robert J. Lee, Columbus, OH (US)

(73) Assignee: Ohio State Innovation Foundation, Columbus, OH (US)

(*) Notice: Subject to any disclaimer, the term of this patent is extended or adjusted under 35 U.S.C. 154(b) by 36 days.

(21) Appl. No.: 15/798,815

(22) Filed: Oct. 31, 2017

(65) Prior Publication Data
US 2018/0049991 A1 Feb. 22, 2018

Related U.S. Application Data

(62) Division of application No. 14/678,589, filed on Apr. 3, 2015, now Pat. No. 9,833,416.

(60) Provisional application No. 61/975,366, filed on Apr. 4, 2014.

(51) Int. Cl.
| | |
|---|---|
| A61K 9/51 | (2006.01) |
| C12N 15/88 | (2006.01) |
| C12N 15/11 | (2006.01) |
| A61K 9/127 | (2006.01) |
| A61K 31/337 | (2006.01) |
| A61K 31/7088 | (2006.01) |
| C12N 15/113 | (2010.01) |
| A61K 45/06 | (2006.01) |

(52) U.S. Cl.
CPC .......... *A61K 9/5123* (2013.01); *A61K 9/1272* (2013.01); *A61K 9/5169* (2013.01); *A61K 31/337* (2013.01); *A61K 31/7088* (2013.01); *A61K 45/06* (2013.01); *C12N 15/111* (2013.01); *C12N 15/113* (2013.01); *C12N 15/88* (2013.01); *C12N 2310/11* (2013.01); *C12N 2310/113* (2013.01); *C12N 2310/315* (2013.01); *C12N 2310/321* (2013.01); *C12N 2310/3231* (2013.01); *C12N 2320/32* (2013.01)

(58) Field of Classification Search
None
See application file for complete search history.

(56) References Cited

U.S. PATENT DOCUMENTS

| | | | | |
|---|---|---|---|---|
| 2009/0023215 A1* | 1/2009 | Jessee | ................. | C07K 14/005 435/455 |
| 2009/0258923 A1* | 10/2009 | Toyobuku | ............ | A61K 9/1272 514/44 A |
| 2013/0289093 A1* | 10/2013 | Bhat | ...................... | A61K 45/06 514/44 A |
| 2015/0374842 A1* | 12/2015 | Brown | ................. | A61K 9/1271 536/24.5 |

FOREIGN PATENT DOCUMENTS

WO WO-2005026372 A1 * 3/2005 ........... A61K 9/1272

OTHER PUBLICATIONS

Han et al (PLoS One 7(6):e398520, 12 pages, 2012) (Year: 2012).*
Mei et al (Technology in Cancer Research & Treatment, 9(1), 2010) (Year: 2010).*

* cited by examiner

*Primary Examiner* — Richard A Schnizer
(74) *Attorney, Agent, or Firm* — MacMillan, Sobanski & Todd, LLC

(57) ABSTRACT

Methods for inhibiting oligonucleotide activity in vitro or in vivo to a cell that are formulated with at least one oligonucleotide encapsulated in a lipid nanoparticle are disclosed.

17 Claims, 31 Drawing Sheets
(20 of 31 Drawing Sheet(s) Filed in Color)
Specification includes a Sequence Listing.

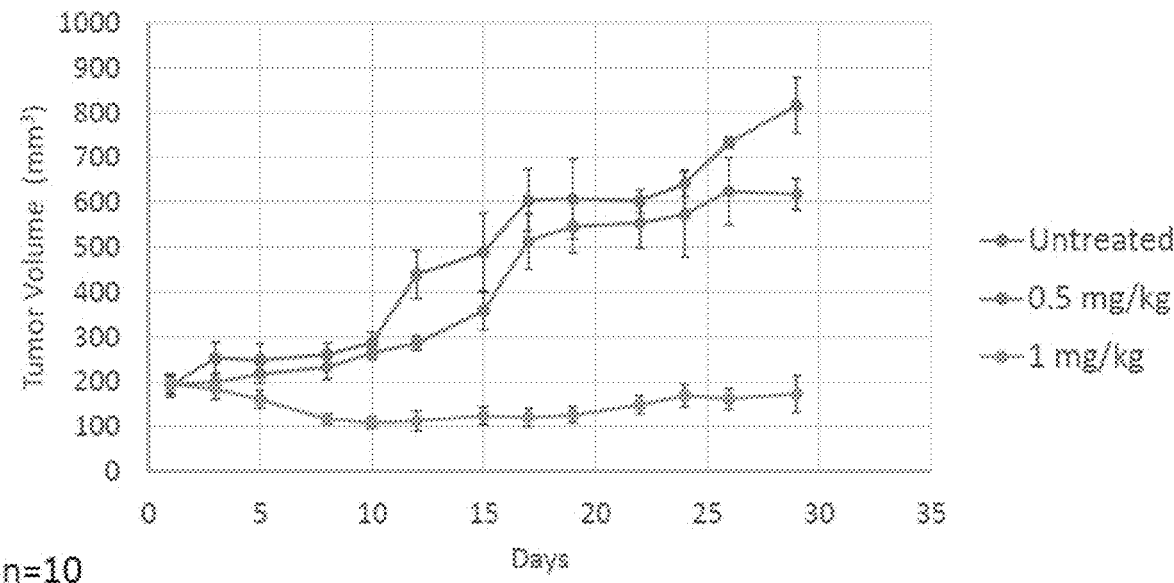
FIG. 5A
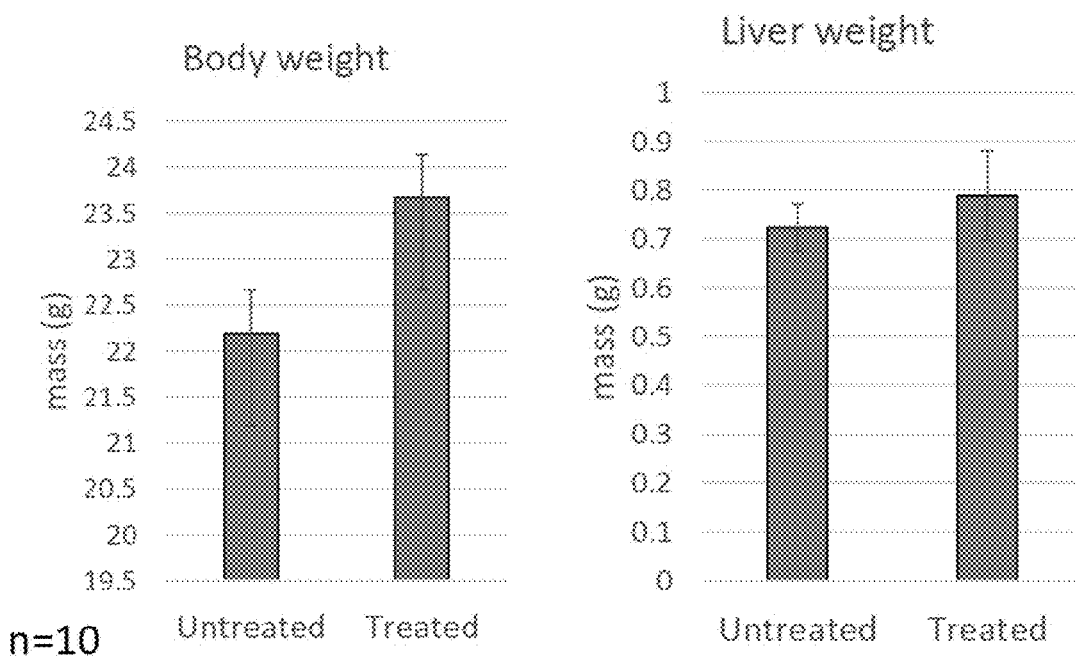
FIG. 5B
FIG. 5C

|  | Color Notation |
|---|---|
| 101 | T*C*A*A*C*A*T*C*A*G*T*C*T*G*A*T*A*A*G*C*T*A |
| 102 | C*A*G*T*C*T*G*A*T*A*A*G*C*T*A |
| 103 | G*A*T*A*A*G*C*T |
| 104 | T*C*A*G*T*C*T*G*A*T*A*A*G*C*T*A |
| 105 | T*C*A*G*T*C-T*G*A*T-A*A-G-C*T*A |
| 106 | T*C*A*G*T*C*T*G*A*T*A*A*G*C*T |
| 107 | T*C*A*G*T*C*T*G*A*T-A*A-G*C*T |
| 108 | T*C*A*G*T*C*T*G*A*T*A*A*G*C*T*A |
| 109 | T*C*A*G*T*C*T*G*A*T-A*A*G-C*T*A |
| 110 | T*C*A*G*T*C*T*G*A*T-A*A*G-C*T*A |
| 111 | T*C*A*G*T*C*T*G*A*T*A*A*G*C*T*A |
| 112 | T*C*A*G*T*C*T*G*A*T*A*A*G*C*T |
| 113 | T*C*A*G*U*C*U*G*A*T*A*A*G*C*T*A |
| 114 | T*C*A*G*T*C*T*G*A*T*A*A*G*C*T |
| 115 | T*C*A*G*T*C-T*G*A*T-A*A-G-C*T*A |
| 116 | T*C*A*G*T*C-T-G*A*T*A-A-G*C*T*A |
| 117 | T*C*A*G*T*C-T-G*A*T*A-A-G*C*T |
| 118 | T*C*A*G*T*C-T-G*A*T-A-A-G*C*T*A |
| 119 | T*C*A*G*T*C*T*G*A*T-A*A*G-C*T |
| 120 | T*C*A*A*C*A*T*C*A-G-T-C-T-G-A-T-A-A-G*C*T*A |
| 121 | T*C*A*A*C*A*T-C-A-G-T-C-T-G-A-T-A*A*G*C*T*A |
| 122 | C*A*T*C-A-G-T-C-T-G-A-T-A-A-G*C*T*A |
| 123 | T*C*A*G-T-C-T-G-A-T-A-A-G*C*T*A |
| 124 | T*G*A*T*A*A*G*C*T |
| 125 | T-G-A-T-A-A-G-C-T |
|  | LNA, 2'OMe, "-" PO linkage "*" PS linkage |

FIG. 15

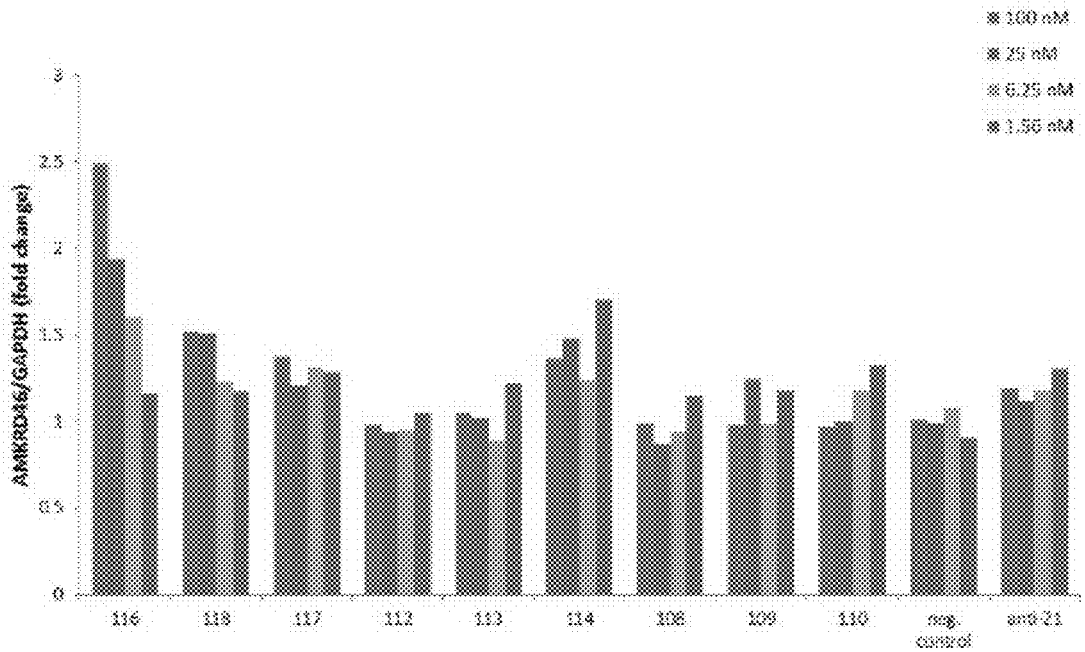

FIG. 16A

Zeta Potential W/O Oligo

| | Tertiary Amine | Quarternary Amine | QTsome |
|---|---|---|---|
| 5.5 | 9.76 | 7.8 | 11.8 |
| 6 | 5.39 | 7.22 | 8.46 |
| 7 | 2.55 | 7.17 | 6.8 |
| 8 | 2.27 | 7.13 | 5.73 |

|   | Saline | | | 2 mg/kg | | |
|---|---|---|---|---|---|---|
|   | Average | SD | SE | Average | SD | SE |
| 1 | 51.78571 | 4.724556 | 1.785714 | 53.57143 | 6.099375 | 2.305347 |
| 4 | 76.71429 | 26.14361 | 9.881354 | 45.85714 | 27.10737 | 10.24562 |
| 6 | 99 | 78.14303 | 29.53529 | 33.85714 | 27.09661 | 10.24156 |
| 8 | 138 | 99.62178 | 37.6535 | 24.78571 | 15.04952 | 5.688184 |
| 11 | 176.1429 | 88.56387 | 33.474 | 23.57143 | 9.791274 | 3.700754 |
| 13 | 208.2143 | 126.0214 | 47.63163 | 28.92857 | 30.14746 | 11.39467 |
| 15 | 270.1429 | 169.4301 | 64.03856 | 23.71429 | 32.68901 | 12.35528 |
| 18 | 303.1429 | 127.2781 | 48.10662 | 27.35714 | 34.02782 | 12.86131 |
| 20 | 378.4286 | 195.5186 | 73.8991 | 40.78571 | 55.18443 | 20.85775 |
| 22 | 601.1429 | 321.3055 | 121.4421 | 36.85714 | 47.26672 | 17.86514 |

OLIGONUCLEOTIDE LIPID NANOPARTICLE COMPOSITIONS, METHODS OF MAKING AND METHODS OF USING THE SAME

RELATED APPLICATIONS

This application is a divisional application of U.S. Ser. No. 14/678,589 filed Apr. 3, 2015, which claims priority to U.S. Provisional Application 61/975,366, filed Apr. 4, 2014, the disclosure of which is hereby incorporated by reference in their entirety.

STATEMENT REGARDING FEDERALLY SPONSORED RESEARCH

This invention was not made with government support and the government has no rights in the invention.

SEQUENCE LISTING

The instant application contains a Sequence Listing which has been submitted via EFS-web and is hereby incorporated by reference in its entirety. The ASCII copy, created on Apr. 3, 2015, is named 604_56088_SEQ_LIST_OSIF-2014-218.txt, and is 19,311 bytes in size.

TECHNICAL FIELD

The present disclosure pertains to lipid nanoparticles (LNPs) usable for the delivery of therapeutic compositions, including, but not limited to nucleic acids (NAs), and to the methods of making the same. In a particular aspect, described herein are quaternary-tertiary lipoamine systems useful for the delivery of anti-miRNA oligonucleotides.

BACKGROUND OF THE INVENTION

Nucleic acid (NA)-based therapies using miRNAs (miRs) and/or anti-miRNA are being developed to promote or inhibit gene expression. miRNAs are non-coding RNAs that can regulate expression of networks of genes by the mechanism of RNA interference (RNAi). This occurs by incorporation of miRNA into an RNA-induced silencing complex (RISC) that mediate translational repression and degradation of target mRNAs. An antimiR is an oligonucleotide that is complementary to a miRNA that inhibits its function thereby de-represses the target genes of the miRNA. As mutations in genes and changes in miRNA profile are believed to be the underlying cause of cancer and other diseases, NA-based agents can directly act upon the underlying etiology, maximizing therapeutic potential. Non-limiting examples of NA-based therapies include: plasmid DNA (pDNA), small interfering RNA (siRNA), small hairpin RNA (shRNA), miR mimic (mimetic), anti-miR/antagomiR/miR inhibitor, and antisense oligonucleotide (ASO). Until the development of the nanoparticle compositions described herein, the clinical translation of NA-based therapies faced several obstacles in their implementation since transporting NAs to their intracellular target was particularly challenging and since NAs are relatively unstable and subject to degradation by serum and cellular nucleases. Further, the high negative charges of NAs made it impossible for diffusion across the cell membrane, further limiting utility.

A liposome is a vesicle composed of one or more lipid bilayers, capable of carrying hydrophilic molecules within an aqueous core or hydrophobic molecules within its lipid bilayer(s). As used herein, "lipid nanoparticles" is a general term to described lipid-based particles in the submicron range. Lipid nanoparticles can have structural characteristics of liposomes and/or have alternative non-bilayer types of structures. Drug delivery by lipid nanoparticles via systemic route requires overcoming several physiological barriers. The reticuloendothelial system (RES) is responsible for clearance of lipid nanoparticles from the circulation. Once escaping the vasculature and reaching the target cell, lipid nanoparticles are typically taken up by endocytosis and must release the drug into the cytoplasm prior to degradation within acidic endosomes and lysosomes.

In particular, the delivery of such nucleic acids (NAs), including siRNA and other therapeutic oligonucleotides is a major technical challenge that has limited their potential for clinical translation.

The development of efficient delivery vehicles is a key to clinical translation of oligonucleotide (ON) therapeutics. It is desired that a lipid nanoparticle formulation should be able to (1) protect the drug from enzymatic degradation; (2) transverse the capillary endothelium; (3) specifically reach the target cell type without causing excessive immunoactivation or off-target cytotoxicity; (4) promote endocytosis and endosomal release; and (5) form a stable formulation with colloidal stability and long shelf-life.

SUMMARY OF THE INVENTION

Provided herein are lipid nanoparticles that can encapsulate therapeutic oligonucleotides with high efficiency and fulfill physical and biological criteria for efficacious delivery.

In one broad aspect, there is provided herein a composition comprising at least one formulated modified anti-miR-21 oligonucleotide comprising a nucleic acid sequence complementary to the sequence of miR-21, wherein the nucleic acid sequence may include chemical modifications such as phosphorothioate linkages and 2'-O-methoxyethyl modifications.

In another broad aspect, there is provided herein a method for lowering the biological activity of miR-21 in vitro comprising: i) contacting a biological sample expressing miR-21 therein, with a formulated modified anti-miR-21 oligonucleotide, wherein the anti-miR-21 oligonucleotide comprises a nucleic acid sequence complementary to the sequence of miR-21; and, ii) lowering the biological activity of miR-21 in vitro.

In another broad aspect, there is provided herein a method of lowering the biological activity of miR-21 in vivo in a subject comprising: i) administering to the subject a formulated anti-miR-21oligonucleotide, wherein the anti-miR-21 oligonucleotide comprises a nucleic acid sequence complementary to the sequence of miR-21; and, ii) lowering the biological activity of miR-21 in vivo in the subject.

In another broad aspect, there is provided herein a method for increasing chemo-sensitivity of a cancer cell in a subject comprising: i) administering to the subject a formulated anti-miR-21oligonucleotide, wherein the anti-miR-21 oligonucleotide comprising a nucleic acid sequence complementary to the sequence of miR-21, and, ii) increasing the chemotherapy-sensitivity of the cancer cell.

In another broad aspect, there is provided herein a method comprising administering the composition as described herein to a subject in an amount sufficient to regulate expression of PTEN, and/or to regulate one or more of cell proliferation, cell invasion and metastasis.

In another broad aspect, there is provided herein a method comprising administering the composition as described herein to a subject in an amount sufficient to regulate expression of RECK and/or TIMP, and/or to regulate one or more of cell invasion and metastasis.

In another broad aspect, there is provided herein, a pharmaceutical composition comprising a composition as described claim herein, and a pharmaceutically acceptable excipient.

In certain embodiments, the modified anti-miR-21 oligonucleotide is formulated with lipid nanoparticles.

In certain embodiments, wherein the nucleic acid sequence consists of the sequence of 5'-U*C*A*ACAUCAGUCUGAUAAG*C*U*A-3' (SEQ ID NO:3), wherein the sequence contains phosphorothioate linkages (*).

In certain embodiments, the lipid nanoparticles comprise cationic lipids.

In certain embodiments, the cationic lipids comprise quaternary cationic lipids and tertiary cationic lipids.

In certain embodiments, the cationic liquids in the composition comprise a "QTsome™" lipid nanoparticle formulation comprised of a determined ratio of quaternary cationic lipids to tertiary cationic lipids.

In certain embodiments, the ratios of quaternary cationic lipids to tertiary cationic lipids are selected from: 5:40; 15:30; 22.5:22.5; 30:15; and, 40:5.

In certain embodiments, the tertiary cationic lipids comprise tertiary amine-cationic lipids.

In certain embodiments, the tertiary amine-cationic lipids are chosen from DODAP, DODMA, DC-CHOL, N,N-dimethylhexadecylamine, or combinations thereof.

In certain embodiments, the quaternary cationic lipids comprise quaternary amine-cationic lipids.

In certain embodiments, the quaternary amine-cationic lipids are selected from DOTAP, DOTMA, DDAB, or combinations thereof.

In certain embodiments, the concentration of the tertiary cationic lipids is below about 60.0 molar percent of the total lipid content.

In certain embodiments, the concentration of quaternary cationic lipids is below about 20.0 molar percent of the total lipid content.

In certain embodiments, the composition comprises the lipids DODMA and DOTMA in a molar ratio selected from 45:0, 5:40, 15:30, 22.5:22.5, 30:15, or 40:5.

In certain embodiments, the composition comprises the lipids DMHDA and DOTAP in a molar ratio selected from 90:10, 70:30, 50:50, 30:70, or 10:90.

In certain embodiments, the "QTsome™" lipid nanoparticle formulation has a formulation comprising: DOTAP/DODMA/DOPC/Cholesterol/PEG-DPPE.

In certain embodiments, the "QTsome™" lipid nanoparticle formulation has a formulation comprising: DOTAP/DODMA/DOPC/Cholesterol/PEG-DPPE at 15:25:36:20:4 mol/mol. For example, in certain embodiments, the formulation comprises: DOTAP/DODMA/DOPC/Cholesterol/PEG-DPPE, where the total molar percent of DOTAP and DODMA is 40:40 mol/mol.

In certain embodiments, the biological sample is a cell culture.

In certain embodiments, the cell culture is a cancer cell culture.

In certain embodiments, the cell culture is a primary cell culture from a cancer biopsy.

In certain embodiments, the biological activity is measured as the expression levels of miR-21 target genes.

In certain embodiments, the miR-21 target genes are PTEN and RECK.

In certain embodiments, the subject has, or is suspected of having, breast cancer, ovarian cancer, lung cancer, non-small cell lung carcinoma, squamous cell lung carcinoma, lung adenocarcinoma, large cell lung carcinoma, or glioma.

In certain embodiments, the subject is a mammal.

In certain embodiments, the subject is a human.

In certain embodiments, the methods described herein further include administering a chemo-therapeutic agent to the subject prior to, simultaneous with, or subsequent to, administration of the anti-miR-21oligonucleotide formulation.

In certain embodiments, the chemo-therapeutic agent comprises paclitaxel.

In certain embodiments, the composition encapsulates one or more additional molecules selected from nucleic acids, proteins, polysaccharides, lipids, radioactive substances, therapeutic agents, prodrugs, nutritional supplements, antibiotics, biomarkers, or combinations thereof.

In certain embodiments, the encapsulated molecules comprise a nucleic acid selected from plasmid DNAs, antisense oligonucleotides, miRs, anti-miRs, shRNAs, siRNAs, or combinations thereof.

In certain embodiments, the encapsulation rate of therapeutic agents or nucleotides is 20% or higher.

In certain embodiments, the composition has a diameter of less than 300 nm. In certain embodiments, the composition has a mean particle diameter of about 105±50 nm.

In certain embodiments, the pharmaceutical composition is administered perorally, intravenously, subcutaneously, or transdermally. In certain embodiments, the pharmaceutical composition is prepared as an orally administered tablet. In certain embodiments, the pharmaceutical composition is prepared as a sterile solution. In certain embodiments, the pharmaceutical composition is prepared as a sterile suspension. In certain embodiments, the pharmaceutical composition is prepared as a lyophilized powder.

In certain embodiments, the oligonucleotide agent is selected from anti-miRs, miR mimics, antisense oligos, siRNA, aptamers, and any combination of these classes of oligonucleotides.

Various objects and advantages of this invention will become apparent to those skilled in the art from the following detailed description of the preferred embodiment, when read in light of the accompanying drawings.

BRIEF DESCRIPTION OF THE DRAWINGS

The patent or application file may contain one or more drawings executed in color and/or one or more photographs. Copies of this patent or patent application publication with color drawing(s) and/or photograph(s) will be provided by the U.S. Patent and Trademark Office upon request and payment of the necessary fees.

FIG. 5A is a graph showing the tumor regression in A549 subcutaneous xenograft mouse model after QT/AM-21 treatment.

FIG. 5B is a graph showing the endpoint measurements of body weights in QT/AM-21 treated A549 subcutaneous xenograft mice.

FIG. 5C is a graph showing the endpoint measurements of liver weights in QT/AM-21 treated A549 subcutaneous xenograft mice.

FIG. 15 is a list of anti-miR-21 compounds 101-125 (SEQ ID NOs:4-28), in order of appearance) which were designed and tested.

FIG. 16A is a graph showing activity of compounds 116, 118, 117, 112, 113, 114, 108, 109, 110, a negative control, and anti-miR-21 of SEQ ID NO:3, in ANKRD46 (ANKRD46/GAPDH (fold change) at 100 nM, 25 nM, 6.25 nM, 1.56 nM).

DETAILED DESCRIPTION OF THE INVENTION

Figure 1:
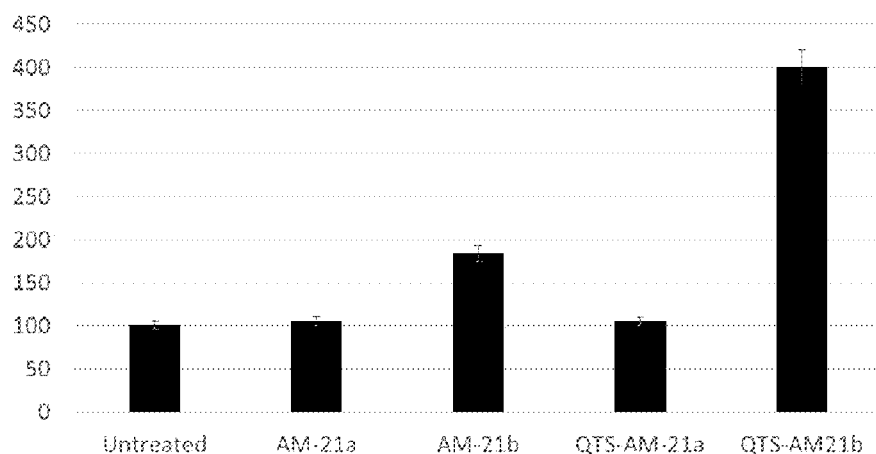
FIG. 1 is a representative graph showing of the upregulation of target PTEN gene after QTsome™ encapsulating anti-miR-21 (QT/AM-21) treatment in vitro in KB cell culture.

Various embodiments are described herein in the context of lipid nanoparticles. Those of ordinary skill in the art will realize that the following detailed description of the embodiments is illustrative only and not intended to be in any way limiting. Other embodiments will readily suggest themselves to such skilled persons having the benefit of this disclosure. Reference to an "embodiment," "aspect," or "example" herein indicate that the embodiments of the invention so described may include a particular feature, structure, or characteristic, but not every embodiment necessarily includes the particular feature, structure, or characteristic. Further, repeated use of the phrase "in one embodiment" does not necessarily refer to the same embodiment, although it may.

Not all of the routine features of the implementations or processes described herein are shown and described. It will, of course, be appreciated that in the development of any such actual implementation, numerous implementation-specific decisions will be made in order to achieve the developer's specific goals, such as compliance with application- and business-related constraints, and that these specific goals will vary from one implementation to another and from one developer to another. Moreover, it will be appreciated that such a development effort might be complex and time-consuming, but would nevertheless be a routine undertaking for those of ordinary skill in the art having the benefit of this disclosure.

General Description and Definitions

Lung cancer is the most common cancer worldwide. The 5-year relative survival rate about 15.7%. Non-small cell lung cancer (NSCLC) accounts for the majority of lung cancers, and is generally categorized into the following types: squamous cell carcinoma, adenocarcinoma, and large cell carcinoma. The risk factors include exposure to cigarette smoke or other airborne carcinogens. NSCLC originates in epithelial cells of the central bronchiole and terminal alveoli. NSCLC is relatively insensitive to chemotherapy and radiation therapy. miR-21 is upregulated in NSCLC, and while not wishing to be bound by theory, the inventors herein now believe that such upregulated miR-21 is target for treatment of NSCLC.

microRNA (miRs) miRs are often differentially expressed between tumor and non-tumor tissue. miRNAs are Small non-protein coding RNA, generally 20-25 nucleotides long, and are capable of regulating hundreds of mRNAs in multiple biological pathways. miRNAs are incorporated in to RNA-induced silencing complexes (RISC) and regulate gene expression through RNA interference. Recognition by RISC leads to target mRNA translational repression. In addition, matching of targets generally occurs in the 3'-UTR of mRNA.

miR-21 is a regulator for a large number of genes. Targets include pathways responsible for cell proliferation, invasion, metastasis, and evasion of apoptosis. Administration of an oligonucleotide miR-inhibitor against miR-21 (anti-miR-21, AM-21) is now shown herein to reverse miR-21 activity.

The genes PTEN and PDCD4 function as tumor suppressors. PTEN inhibits Akt pathway via reversal of PI3K phosphorylation, while PDCD4 inhibits translation initiation factors eIF4A and eIF4G. miR-21 expression is inversely correlated with PTEN and PDCD4.

Asymmetric dimethylarginine (ADMA) is a competitive inhibitor of endothelial nitric oxide synthase. Nitric oxide is responsible for inhibition of apoptosis and regulation of angiogenesis. Dimethylaminohydrolase (DDAH1) is responsible for ADMA elimination and is correlated with increased miR-21 expression.

Reversion-inducing-cysteine-rich protein with kazal motifs (RECK) and metalloproteinase inhibitor 3 (TIMP3) function as metalloproteinase inhibitors. RECK and TIMP3 regulate tumor cell invasion, metastasis, and angiogenesis.

Paclitaxel (PTX) is a common treatment in lung, ovarian, and breast cancers. Several studies suggest that resistance to PTX is linked to overexpression of miR-21 via hypoxia-inducible factor-1α (HIF-1α).

However there are barriers to using miRNAs and anti-miRNAs due, in part, to the difficulty in the delivery of the miRNAs/anti-miRNAs to a target site. In general, the characteristics of miRNAs/anti-miRNAs themselves pose difficulties as the miRNAs/anti-miRNAs are: high molecular weight, have high anionic charge, generally show instability in serum, there is rapid clearance, they have poor pharmacokinetic properties, and may cause undesirable off-target effects.

Subject" means a human or non-human animal selected for treatment or therapy.

"Subject in need thereof" means a subject identified as in need of a therapy or treatment. In certain embodiments, a subject has liver cancer. In such embodiments, a subject has one or more clinical indications of liver cancer or is at risk for developing liver cancer.

"At risk for developing cancer" means the state in which a subject is predisposed to developing cancer.

"Administering" means providing a pharmaceutical agent or composition to a subject, and includes, but is not limited to, administering by a medical professional and self-administering.

"Parenteral administration," means administration through injection or infusion. Parenteral administration includes, but is not limited to, subcutaneous administration, intravenous administration, or intramuscular administration.

"Administered concomitantly" refers to the co-administration of two agents in any manner in which the pharmacological effects of both are manifest in the patient at the same time. Concomitant administration does not require that both agents be administered in a single pharmaceutical composition, in the same dosage form, or by the same route of administration. The effects need only be overlapping for a period of time and need not be coextensive.

"Chemoembolization" means a procedure in which the blood supply to a tumor is blocked surgically, mechanically, or chemically and chemotherapeutic agents are administered directly into the tumor.

"Duration" means the period of time during which an activity or event continues. In certain embodiments, the duration of treatment is the period of time during which doses of a pharmaceutical agent or pharmaceutical composition are administered.

"Therapy" means a disease treatment method. In certain embodiments, therapy includes, but is not limited to, chemotherapy, surgical resection, liver transplant, and/or chemoembolization.

"Treatment" means the application of one or more specific procedures used for the cure or amelioration of a disease. In certain embodiments, the specific procedure is the administration of one or more pharmaceutical agents.

"Amelioration" means a lessening of severity of at least one indicator of a condition or disease. In certain embodiments, amelioration includes a delay or slowing in the progression of one or more indicators of a condition or disease. The severity of indicators may be determined by subjective or objective measures which are known to those skilled in the art.

"Prevention" refers to delaying or forestalling the onset or development or progression of a condition or disease for a period of time, including weeks, months, or years.

"Prevent the onset of" means to prevent the development a condition or disease in a subject who is at risk for developing the disease or condition. In certain embodiments, a subject at risk for developing the disease or condition receives treatment similar to the treatment received by a subject who already has the disease or condition.

"Delay the onset of" means to delay the development of a condition or disease in a subject who is at risk for developing the disease or condition. In certain embodiments, a subject at risk for developing the disease or condition receives treatment similar to the treatment received by a subject who already has the disease or condition.

"Therapeutic agent" means a pharmaceutical agent used for the cure, amelioration or prevention of a disease.

"Anti-cancer therapy" means a therapy aimed at treating or preventing cancer. In certain embodiments, anti-cancer therapy comprises chemotherapy. In certain embodiments, anti-cancer therapy comprises radiation therapy.

"Chemotherapeutic agent" means a pharmaceutical agent used to treat cancer.

"Chemotherapy" means treatment of a subject with one or more pharmaceutical agents for the treatment of cancer.

"Metastasis" means the process by which cancer spreads from the place at which it first arose as a primary tumor to other locations in the body. The metastatic progression of a primary tumor reflects multiple stages, including dissociation from neighboring primary tumor cells, survival in the circulation, and growth in a secondary location.

"Overall survival time" means the time period for which a subject survives after diagnosis of or treatment for a disease. In certain embodiments, the disease is cancer.

"Progression-free survival" means the time period for which a subject having a disease survives, without the disease getting worse. In certain embodiments, progression-free survival is assessed by staging or scoring the disease. In certain embodiments, progression-free survival of a subject having liver cancer is assessed by evaluating tumor size, tumor number, and/or metastasis.

"Biomarker" means a substance that is used as an indicator of a biologic state. Biomarkers are objectively measured and evaluated as an indicator of normal biologic processes, pathogenic processes, or pharmacologic responses to a therapeutic intervention.

"Cancer biomarker" means a substance that is used as an indicator of a cancerous state. For example, a cancer biomarker may indicate the presence of cancer, or the response to an anti-cancer therapy.

"Improved organ function" means the change in organ function toward normal organ function. In certain embodiments, organ function is assessed by measuring molecules found in a subject's blood.

"Dose" means a specified quantity of a pharmaceutical agent provided in a single administration. In certain embodiments, a dose may be administered in two or more boluses, tablets, or injections.

"Dosage unit" means a form in which a pharmaceutical agent is provided.

"Therapeutically effective amount" refers to an amount of a pharmaceutical agent that provides a therapeutic benefit to an animal.

"Pharmaceutical composition" means a mixture of substances suitable for administering to an individual that includes a pharmaceutical agent.

"Pharmaceutical agent" means a substance that provides a therapeutic effect when administered to a subject.

"Active pharmaceutical ingredient" means the substance in a pharmaceutical composition that provides a desired effect.

"Acceptable safety profile" means a pattern of side effects that is within clinically acceptable limits "Target nucleic acid," "target RNA," "target RNA transcript" and "nucleic acid target" all mean any nucleic acid capable of being targeted by antisense compounds.

"Targeting" means the process of design and selection of nucleobase sequence that will hybridize to a target nucleic acid and induce a desired effect.

"Targeted to" means having a nucleobase sequence that will allow hybridization to a target nucleic acid to induce a desired effect. In certain embodiments, a desired effect is reduction of a target nucleic acid.

"Expression" means any functions and steps by which a gene's coded information is converted into structures present and operating in a cell.

"Natural nucleobase" means a nucleobase that is unmodified relative to its naturally occurring form.

A "stabilizing modification" means a modification to a nucleoside that provides enhanced stability to a modified oligonucleotide, in the presence of nucleases, relative to that provided by nucleosides or 2'-deoxynucleosides linked by phosphodiester internucleoside linkages. For example, in certain embodiments, a stabilizing modification is a stabilizing nucleoside modification.

Compositions of the present invention comprise oligomeric compounds comprising oligonucleotides having nucleobase sequences that share identity with endogenous miRNA or miRNA precursor nucleobase sequences. An oligonucleotide selected for inclusion in a composition of the present invention may be one of a number of lengths. Such an oligonucleotide can be from 7 to 100 linked nucleosides in length. For example, an oligonucleotide sharing nucleobase identity with a miRNA may be from 7 to 30 linked nucleosides in length. An oligonucleotide sharing identity with a miRNA precursor may be up to 100 linked nucleosides in length.

In certain embodiments, an oligonucleotide consists of 7 to 30 linked nucleosides. In certain embodiments, an oligonucleotide consists of 7, 8, 9, 10, 11, 12, 13, 14, 15, 16, 17, 18, 19, 20, 21, 22, 23, 24, 25, 26, 28, 29, or 30 linked nucleotides.

In certain embodiments, an oligonucleotide consists of 15 to 30 linked nucleosides. In certain embodiments, an oligonucleotide consists of 15 linked nucleosides. In certain embodiments, an oligonucleotide consists of 16 linked nucleosides. In certain embodiments, an oligonucleotide consists of 17 linked nucleosides. In certain embodiments, an oligonucleotide consists of 18 linked nucleosides. In certain embodiments, an oligonucleotide consists of 19 linked nucleosides. In certain embodiments, an oligonucleotide consists of 20 linked nucleosides. In certain embodiments, an oligonucleotide consists of 21 linked nucleosides. In certain embodiments, an oligonucleotide consists of 22 linked nucleosides. In certain embodiments, an oligonucleotide consists of 23 linked nucleosides. In certain embodiments, an oligonucleotide consists of 24 linked nucleosides. In certain embodiments, an oligonucleotide consists of 25 linked nucleosides. In certain embodiments, an oligonucleotide consists of 26 linked nucleosides. In certain embodiments, an oligonucleotide consists of 27 linked nucleosides. In certain embodiments, an oligonucleotide consists of 28 linked nucleosides. In certain embodiments, an oligonucleotide consists of 29 linked nucleosides. In certain embodiments, an oligonucleotide consists of 30 linked nucleosides.

In certain embodiments, an oligonucleotide consists of 19 to 23 linked nucleosides. In certain embodiments, an oligonucleotide is from 40 up to 50, 60, 70, 80, 90, or 100 linked nucleosides in length.

In certain embodiments, an oligonucleotide has a sequence that has a certain identity to a miRNA or a precursor thereof. Nucleobase sequences of mature miRNAs and their corresponding stem-loop sequences described herein are the sequences found in miRBase, an online searchable database of miRNA sequences and annotation, found at the website microRNA"dot"sanger"dot"ac"dot"uk. Entries in the miRBase Sequence database represent a predicted hairpin portion of a miRNA transcript (the stem-loop), with information on the location and sequence of the mature miRNA sequence. The miRNA stem-loop sequences in the database are not strictly precursor miRNAs (pre-miRNAs), and may in some instances include the pre-miRNA and some flanking sequence from the presumed primary transcript. The miRNA nucleobase sequences described herein encompass any version of the miRNA, including the sequences described in Release 10.0 of the miRBase sequence database and sequences described in any earlier Release of the miRBase sequence database. A sequence database release may result in the re-naming of certain miRNAs. A sequence database release may result in a variation of a mature miRNA sequence. The compositions of the present invention encompass oligomeric compound comprising oligonucleotides having a certain identity to any nucleobase sequence version of a miRNAs described herein.

In certain embodiments, an oligonucleotide has a nucleobase sequence at least 60%, 65%, 70%, 75%, 80%, 85%, 90%, 95%, 97%, 98% or 99% A identical to the miRNA over a region of 7, 8, 9, 10, 11, 12, 13, 14, 15, 16, 17, 18, 19, 20, 21, 22, 23, 24, 25, 26, 27, 28, 29, or 30 nucleobases. Accordingly, in certain embodiments the nucleobase sequence of an oligonucleotide may have one or more non-identical nucleobases with respect to the miRNA. In certain embodiments, the miRNA is miR-21.

In certain embodiments, an oligonucleotide has a nucleobase sequence at least 60%, 65%, 70%, 75%, 80%, 85%, 90%, 95%, 97%, 98% or 99% A identical to the precursor over a region of 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, or 100 nucleobases. In certain embodiments, the miRNA precursor is a miR-21 precursor.

Compositions of the present invention may comprise oligonucleotides having a percentage region identity and percentage overall identity that are different from one another. In certain embodiments, a region of the nucleobase sequence of an oligonucleotide is 100% identical to the nucleobase sequence of the miRNA, but the oligonucleotide does not have 100% overall identity to the entire miRNA. In certain such embodiments, the number of nucleosides of the oligonucleotide is greater than the length of the miRNA, but the oligonucleotide has a region that is 100% identical to the miRNA.

Compositions described herein may comprise oligonucleotides having seed region identity with a miRNA. In certain embodiments, the nucleobase sequence of an oligonucleotide has at least 80% seed region identity with the nucleobase sequence of a miRNA. In certain embodiments, the nucleobase sequence of an oligonucleotide has at least 85% seed region identity with the nucleobase sequence of a miRNA. In certain embodiments, the nucleobase sequence of an oligonucleotide has at least 90% seed region identity with the nucleobase sequence of a miRNA. In certain embodiments, the nucleobase sequence of an oligonucleotide has at least 95% seed region identity with the nucleobase sequence of a miRNA. In certain embodiments, the nucleobase sequence of an oligonucleotide has 100% seed region identity with the nucleobase sequence of a miRNA.

Compositions herein may also comprise locked nucleic acid (LNA) substituted oligonucleotides. Locked nucleic acid substituted oligonucleotides have increased nuclease stability and greatly increased RNA target binding affinity. Therefore, locked nucleic acid is useful to enhance the activity of anti-miRs. For example, the compounds 101-119 shown in FIG. 15 (SEQ ID NOs:3-21) are LNA-containing oligonucleotides. In other, non-limiting examples, other types of modifications such as unlocked nucleic acid (UNA), morpholine substituted, 2'-methoxyethyl (MOE), 2'-F, peptide nucleic acid (PNA), conformationally restricted nucleosides (CRN) are also useful to construct anti-miRs.

Certain Nanoparicles

The nanoparticles described herein are especially useful for the delivery of miRNAs/anti-miRNAs. The nanoparticles include cationic polymers or lipid components which provide improved pharmacokinetics and increased cellular uptake. The nanoparticles described herein provide protection of the anti-miR against degradation. Also, the nanoparticles provide improved safety parameters, provide passive targeting by enhanced permeation and retention (EPR) effect, and the capability of targeting specific cell types with ligands.

Endosomal escape is a rate limiting factor in anti-miR delivery. Described herein are fusogenic lipids that are used to help the nanoparticle avoid degradation in the lysosome by promoting endosomal lysis. Useful fusogenic lipids include phosphatidylethanolamines and cholesterol.

The lipid nanoparticles described herein provide a useful platform for the delivery of both traditional therapeutic compounds and NA-based therapies. Drugs formulated using lipid nanoparticles provide desirable pharmacokinetic (PK) properties in vivo, such as increased blood circulation time and increased accumulation at the site of solid tumors due to enhanced permeability and retention (EPR) effect. Moreover, in certain embodiments, the lipid nanoparticles may be surface-coated with polyethylene glycol to reduce opsonization of lipid nanoparticles by serum proteins and the resulting RES-mediated uptake, and/or coated with cell-specific ligands to provide targeted drug delivery.

It is desired that the zeta potential of lipid nanoparticles not be excessively positive or negative for systemic delivery. Lipid nanoparticles with a highly positive charge tend to interact non-specifically with non-target cells, tissues, and circulating plasma proteins, and may cause toxicity and rapid clearance. Alternatively, lipid nanoparticles with a highly negative charge cannot effectively incorporate NAs, which are themselves negatively charged, and may trigger rapid RES-mediated clearance, reducing therapeutic efficacy. Lipid nanoparticles with a neutral to moderate charge are best suited for in vivo drug and gene delivery.

Provided herein are lipid nanoparticles (lipid nanoparticles) with improved transfection activity. The lipid nanoparticles may either partition hydrophobic molecules within the lipid membrane or encapsulate water-soluble particles or molecules within the aqueous core.

In certain embodiments, the lipid nanoparticles are produced by combining cationic lipids with quaternary amine headgroups and cationic lipids with tertiary amine headgroups. In certain embodiment, the lipid nanoparticles are small peptidic lipid nanoparticles (SPLN) and comprise a peptide such as gramicidin or JTS1. Exemplary lipid nanoparticles are disclosed in PCT WO2013/177419, the entire contents of which are expressly incorporated herein.

Combinations of these different embodiments are further provided. The lipid nanoparticles have a diameter of less than 300 nm, or in particular embodiments between about 50 and about 200 nm. These lipid nanoparticles show enhanced transfection and reduced cytotoxicity, especially under high serum conditions found during systemic administration. The lipid nanoparticles are applicable to a wide range of current therapeutic agents and systems, serum stability, and targeted delivery, with high transfection efficiency.

The term "lipid nanoparticle" as used herein refers to any vesicles formed by one or more lipid components. The lipid nanoparticle formulations described herein may include cationic lipids. Cationic lipids are lipids that carry a net positive charge. The positive charge is used for association with negatively charged therapeutics such as ASOs and anti-miRs via electrostatic interaction. In specific embodiments and in abbreviations in the Figures, the lipid nanoparticle may be referred to herein as "QTsome™ lipid nanoparticle formulation," as "QTsome™" or as "QT."

Suitable cationic lipids include, but are not limited to: 3β-(N-(N',N'-dimethylaminoethane)-carbamoyl)cholesterol hydrochloride (DC-Chol); 1,2-dioleoyl-3-trimethylammonium-propane (DOTAP); 1,2-dioleoyl-3-dimethylammonium-propane (DODAP); dimethyldioctadecylammonium bromide salt (DDAB); 1,2-dilauroyl-sn-glycero-3-ethylphosphocholine chloride (DL-EPC); N-(1-(2,3-dioleyloyx)propyl)-N-N-N-trimethyl ammonium chloride (DOTMA); N-(1-(2,3-dioleyloyx) propyl)-N-N-N-dimethyl ammonium chloride (DODMA); N,N-dioctadecyl-N,N-dimethylammonium chloride (DODAC); N-(1-(2,3-dioleyloxy)propyl)-N-2-(sperminecarboxamido)ethyl)-N,N-dimethylammonium trifluoracetate (DOSPA); 1,2-dimyristyloxypropyl-3-dimethylhydroxyethyl ammonium bromide (DMRIE); dioctadecylamidoglycylspermine (DOGS); neutral lipids conjugated to cationic modifying groups; and combinations thereof. In addition, a number of cationic lipids in available preparations could be used, such as LIPOFECTIN® (from GIBCO/BRL), LIPOFECTAMINE® (from GIBCO/MRL), siPORT NEOFX® (from Applied Biosystems), TRANSFECTAM® (from Promega), and TRANSFECTIN® (from Bio-Rad Laboratories, Inc.). The cationic lipids of the present disclosure may be present at concentrations ranging from about 0 to about 80.0 molar percent of the lipids in the formulation, or from about 5.0 to about 50.0 molar percent of the formulation.

In certain embodiments, the lipid nanoparticle formulations presently disclosed may also include anionic lipids. Anionic lipids are lipids that carry a net negative charge at physiological pH. These anionic lipids, when combined with cationic lipids, are useful to reduce the overall surface charge of lipid nanoparticles and introduce pH-dependent disruption of the lipid nanoparticle bilayer structure, facilitating nucleotide release by inducing nonlamellar phases at acidic pH or induce fusion with the cellular membrane.

Examples of suitable anionic lipids include, but are not limited to: fatty acids such as oleic, linoleic, and linolenic acids; cholesteryl hemisuccinate; 1,2-di-O-tetradecyl-sn-glycero-3-phospho-(1'-rac-glycerol) (Diether PG); 1,2-dimyristoyl-sn-glycero-3-phospho-(1'-rac-glycerol) (sodium salt); 1,2-dimyristoyl-sn-glycero-3-phospho-L-serine (sodium salt); 1-hexadecanoyl,2-(9Z,12Z)-octadecadienoyl-sn-glycero-3-phosphate; 1,2-dioleoyl-sn-glycero-3-(phospho-rac-(1-glycerol)) (DOPG); dioleoylphosphatidic acid (DOPA); and 1,2-dioleoyl-sn-glycero-3-phospho-L-serine (DOPS); anionic modifying groups conjugated to neutral lipids; and combinations thereof. The anionic lipids of the present disclosure are present at concentrations up to about 60.0 molar percent of the formulation, or from about 5.0 to about 25.0 molar percent of the formulation.

In certain embodiments, charged lipid nanoparticles are advantageous for transfection, but off-target effects such as cytotoxicity and RES-mediated uptake may occur. Hydrophilic molecules such as polyethylene glycol (PEG) may be conjugated to a lipid anchor and included in the lipid nanoparticles described herein to discourage lipid nanoparticle aggregation or interaction with membranes. Hydrophilic polymers may be covalently bonded to lipid components or conjugated using crosslinking agents to functional groups such as amines.

Suitable conjugates of hydrophilic polymers include, but are not limited to: polyvinyl alcohol (PVA); polysorbate 80; 1,2-distearoyl-sn-glycero-3-phosphoethanolamine-N-PEG2000 (DSPE-PEG2000); D-alpha-tocopheryl polyethylene glycol 1000 succinate (TPGS); dimyristoylphosphatidylethanolamine-PEG2000 (DMPE-PEG2000); and dipalmitoylphosphatidlyethanolamine-PEG2000 (DPPE-PEG2000). The hydrophilic polymer may be present at concentrations ranging from about 0 to about 15.0 molar percent of the formulation, or from about 5.0 to about 10.0 molar percent of the formulation. The molecular weight of the PEG used is between about 100 and about 10,000 Da, or from about 100 to about 2,000 Da.

The lipid nanoparticles described herein may further comprise neutral and/or amphipathic lipids as helper lipids. These lipids are used to stabilize the formulation, reduce elimination in vivo, or increase transfection efficiency. The lipid nanoparticles may be formulated in a solution of saccharides such as, but not limited to, glucose, sorbitol, sucrose, maltose, trehalose, lactose, cellubiose, raffinose, maltotriose, dextran, or combinations thereof, to promote lyostability and cryostability.

Neutral lipids have zero net charge at physiological pH. One or a combination of several neutral lipids may be included in any lipid nanoparticle formulation disclosed herein.

Suitable neutral lipids include, but are not limited to: phosphatidylcholine (PC), phosphatidylethanolamine, ceramide, cerebrosides, sphingomyelin, cephalin, cholesterol, diacylglycerols, glycosylated diacylglycerols, prenols, lysosomal PLA2 substrates, N-acylglycines, and combinations thereof.

Other suitable lipids include, but are not limited to: phosphatidylcholine, phosphatidic acid, phosphatidylethanolamine, phosphatidylglycerol, phosphatidylcholine, and lysophosphatidylethanolamine; sterols such as cholesterol, demosterol, sitosterol, zymosterol, diosgenin, lanostenol, stigmasterol, lathosterol, and dehydroepiandrosterone; and sphingolipids such as sphingosines, ceramides, sphingomyelin, gangliosides, glycosphingolipids, phosphosphingolipids, phytoshingosine; and combinations thereof.

The lipid nanoparticle formulations described herein may further comprise fusogenic lipids or fusogenic coatings to promote membrane fusion. Examples of suitable fusogenic lipids include, but are not limited to, glyceryl mono-oleate, oleic acid, palmitoleic acid, phosphatidic acid, phosphoinositol 4,5-bisphosphate ($PIP_2$), and combinations thereof.

The lipid nanoparticle formulations described herein may further comprise cationic lipids. The headgroups of such lipids may be primary, secondary, tertiary, or quaternary amines in nature. In certain embodiments, the lipid nanoparticles comprise a mixture of tertiary and quaternary amines.

Suitable tertiary aminolipids include, but are not limited to: DODAP; DODMA; N,N-dimethylhexadecylamine (DMHDA); DC-CHOL; 1,2-DiLinoleyloxy-N,N-dimethylaminopropane (DLinDMA), 1,2-Dilinolenyloxy-N,N-dimethylaminopropane (DLenDMA), 1,2-distearyloxy-N,N-Dimethylaminopropane (DSDMA), ionizable cationic lipids DLinDAP, DLinKDMA, and DLinKC2-DMA.

Suitable quaternary aminolipids include, but are not limited to: DOTAP, DOTMA, DDAB, 1,2-dilinoleyloxy-3-trimethylaminopropane chloride salt (DLin-DMA.Cl), 1,2-dilinoleoyl-3-trimethylaminopropane chloride salt (DLin-TAP.Cl), 1,2-Dilinolenyloxy-3-trimethylaminopropane chloride salt. (DLen-TMA.Cl), and1,2-Dilinolenyloxy-3-trimethylaminopropane chloride salt (DLen-TAP.Cl).

Combinations of multiple aminolipids, particularly of tertiary and quaternary cationic lipids, are beneficial towards lipid nanoparticle delivery of therapeutic agents. In certain embodiments, the cationic lipids may be present in concentrations up to about 60 molar percent combined.

The lipid nanoparticle formulations described here may further comprise cationic polymers or conjugates of cationic polymers. Cationic polymers or conjugates thereof may be used alone or in combination with lipid nanocarriers.

Suitable cationic polymers include, but are not limited to: polyethylenimine (PEI); pentaethylenehexamine (PEHA); spermine; spermidine; poly(L-lysine); poly(amido amine) (PAMAM) dendrimers; polypropyleneiminie dendrimers; poly(2-dimethylamino ethyl)-methacrylate (pDMAEMA); chitosan; tris(2-aminoethyl)amine and its methylated derivatives; and combinations thereof. Chain length and branching are important considerations for the implementation of polymeric delivery systems. High molecular weight polymers such as PEI (MW 25,000) are used as transfection agents, but suffer from cytotoxicity. Low molecular weight PEI (MW 600) does not cause cytotoxicity, but is limited due to its inability to facilitate stable condensation with nucleic acids.

Anionic polymers may be incorporated into the lipid nanoparticle formulations presently disclosed as well. Suitable anionic polymers include, but are not limited to: poly(propylacrylic acid) (PPAA); poly(glutamic acid) (PGA); alginates; dextrans; xanthans; derivatized polymers; and combinations thereof.

In certain embodiments, the lipid nanoparticle formulation includes conjugates of polymers. The conjugates may be crosslinked to targeting agents, lipophilic moieties, peptides, proteins, or other molecules that increase the overall therapeutic efficacy.

Suitable crosslinking agents include, but are not limited to: N-succinimidyl 3-(2-pyridyldithio)-propionate (SPDP); dimethyl 3,3'-dithiobispropionimidate (DTBP); dicyclohexylcarbodiimide (DCC); diisopropyl carbodiimide (DIC); 1-ethyl-3-(3-dimethylaminopropyl)carbodiimide (EDC); N-hydroxysulfosuccinimide (Sulfo-NHS); N'-N'-carbonyldiimidazole (CDI); N-ethyl-5-phenylisoxazolium-3'sulfonate (Woodward's reagent K); and combinations thereof.

The lipid nanoparticle formulations may further comprise peptides and/or proteins. Peptides and proteins, especially those derived from bacteria and viruses or used as antibiotic agents, may aid in membrane permeation. The peptides or proteins may be directly mixed with lipids, covalently attached, or conjugated to lipid moieties with crosslinking agents.

Suitable peptides and proteins include, but are not limited to: gramicidin A, B, C, D, and S; HA2; JTS-1; proteinase K (PrK); trichorovin-Xlla (TV-Xlla); rabies virus glycoprotein (RVG); interleukin-β; HIV-Tat; herpes simplex virus (HSV) VP22 protein; and combinations thereof. In certain embodiments, JTS-1 and/or gramicidin is used at about 0 to about 40 molar percent. In certain embodiments, PrK at a concentration of about 0 to about 30 molar percent is applied by direct mixing with oligonucleotide or conjugation to hexadecyl isothiocyanate for lipid nanoparticle surface coating of PrK.

The addition of targeting agents to the lipid nanoparticle provides increased efficacy over passive targeting approaches. Targeting involves incorporation of specific targeting moieties such as, but not limited to, ligands or antibodies against cell surface receptors, peptides, lipoproteins, glycoproteins, hormones, vitamins, antibodies, antibody fragments, prodrugs, and conjugates or combinations of these moieties.

In certain embodiments, maximization of targeting efficiency includes the surface coating of the lipid nanoparticle with the appropriate targeting moiety rather than encapsulation of the targeting agent. This method optimizes interaction with cell surface receptors.

It is to be understood that targeting agents may be either directly incorporated into the lipid nanoparticle during synthesis or added in a subsequent step. Functional groups on the targeting moiety as well as specifications of the therapeutic application (e.g., degradable linkage) dictate the appropriate means of incorporation into the lipid nanoparticle. Targeting moieties that do not have lipophilic regions cannot insert into the lipid bilayer of the lipid nanoparticle directly and require prior conjugation to lipids before insertion or must form an electrostatic complex with the lipid nanoparticles.

Also, under certain circumstances, a targeting ligand cannot directly bind to a lipophilic anchor. In these circumstances, a molecular bridge in the form of a crosslinking agent may be utilized to facilitate the interaction. In certain embodiments, it is advantageous to use a crosslinking agent if steric restrictions of the anchored targeting moiety prevent sufficient interaction with the intended physiological target. Additionally, if the targeting moiety is only functional under certain orientations (e.g., monoclonal antibody), linking to a lipid anchor via crosslinking agent is beneficial. Traditional methods of bioconjugation may be used to link targeting agents to lipid nanoparticles. Reducible or hydrolysable linkages may be applied to prevent accumulation of the formulation in vivo and subsequent cytotoxicity.

Various methods of lipid nanoparticle preparation are suitable to synthesize the lipid nanoparticles of the present disclosure. For example, ethanol dilution, freeze-thaw, thin film hydration, sonication, extrusion, high pressure homogenization, detergent dialysis, microfluidization, tangential flow diafiltration, sterile filtration, and/or lyophilization may be utilized. Additionally, several methods may be employed to decrease the size of the lipid nanoparticles. For example, homogenization may be conducted on any devices suitable for lipid homogenization such as an Avestin Emulsiflex C5® device. Extrusion may be conducted on a Lipex Biomembrane extruder using a polycarbonate membrane of appropriate pore size (0.05 to 0.2 μm). Multiple particle size reduction cycles may be conducted to minimize size variation within the sample. The resultant lipid nanoparticles may then be passed through a size exclusion column such as Sepharose CL-4B or processed by tangential flow diafiltration to purify the lipid nanoparticles.

Any embodiment of the lipid nanoparticles described herein may further include ethanol in the preparation process. The incorporation of about 30-50% ethanol in lipid nanoparticle formulations destabilizes the lipid bilayer and promotes electrostatic interactions among charged moieties such as cationic lipids with anionic oligonucleotides, such as ASO and siRNA. Lipid nanoparticles prepared in high ethanol solution are diluted before administration. Alternatively, ethanol may be removed by dialysis, or diafiltration, which also removes non-encapsulated NA.

In certain embodiment, it is desirable that the lipid nanoparticles be sterilized. This may be achieved by passing of the lipid nanoparticles through a 0.2 or 0.22 μm sterile filter with or without pre-filtration.

Physical characterization of the lipid nanoparticles can be carried through many methods. Dynamic light scattering (DLS) or atomic force microscopy (AFM) can be used to determine the average diameter and its standard deviation. In certain embodiments, it is especially desirable that the lipid nanoparticles have about a 200 nm diameter. Zeta potential measurement via zeta potentiometer is useful in determining the relative stability of particles. Both dynamic light scattering analysis and zeta potential analysis may be conducted with diluted samples in deionized water or appropriate buffer solution. Cryogenic transmission electron microscopy (Cryo-TEM) and scanning electron microscopy (SEM) may be used to determine the detailed morphology of lipid nanoparticles.

The lipid nanoparticles described herein are stable under refrigeration for several months. Lipid nanoparticles requiring extended periods of time between synthesis and administration may be lyophilized using standard procedures. A cryoprotectant such as 10% sucrose may be added to the lipid nanoparticle suspension prior to freezing to maintain the integrity of the formulation. Freeze drying loaded lipid nanoparticle formulations is recommended for long term stability.

Quaternary Amine-Cationic and Tertiary Amine-Cationic Lipid Nanoparticle Formulations ("QTSOME™")

While the physical characteristics of lipid nanoparticles promote enhanced permeation and retention (EPR) in the fenestrated tumor vasculature, endosomal escape remains a challenge for conventional lipid nanoparticle formulations. To this end, lipid nanoparticles comprising positively charged quaternary or tertiary amine-based cationic lipids for the complexation of nucleic acids have been developed. Quaternary amine-based cationic lipids carry a permanent positive charge and are capable of forming stable electrostatic complexes with nucleic acids. Tertiary amine-cationic lipids, however, are conditionally ionizable and their positive charge is largely regulated by pH. Provided herein are lipid nanoparticles comprising a combination of quaternary and tertiary amine-cationic lipids ("QTsome™" lipid nanoparticle formulations), which provides a mechanism by which therapeutic agents may be released from lipid nanoparticles within the endosome. "QTsome™" lipid nanoparticle formulations are conditionally ionizable and facilitate disruption of the lipid bilayer and oligonucleotide endosomal release under the acidic conditions of the endosome. Quaternary amino-cationic lipids are permanently charged, ensuring strong interaction between the lipids and the oligonucleotide, thereby ensuring stability. The combination of tertiary and quaternary cationic lipids provides an optimum pH response profile that is not possible with each class of lipid individually. "QTsome™" lipid nanoparticle formulations are more active than regular cationic liposomes in transfecting cells.

"QTsome™" lipid nanoparticle formulations demonstrate greater transfection activity than standard cationic lipid formulations. Fine tuning the balance between quaternary and tertiary amine-cationic lipids allows for the precise controlled release of nucleic acids into the cytosol. In a particular embodiment, the use of particular release parameters provides a technique whereby the activity of nucleic acid-based therapeutics can be maximized For example, it is noted that tertiary amine-cationic lipids have pH-dependent ionization profiles when used alone. Since a single lipid species may not provide a desired level of control of lipid nanoparticle charge characteristics, a combination of a tertiary and a quaternary amine-cationic lipid can be used, thus resulting in significantly improved activity of such combinations in siRNA delivery.

It is to be understood that both the tumor environment and endosomes have acidic pH. While not wishing to be bound by theory, it is now believe that when QTsomes get into the tumor, they may acquire positive surface charge due to the acidity of the tumor environment and interact with the plasma membrane of tumor cells. The endosomes are even more acidic and can trigger further increase in cationic charge; but, both types of pH trigger contribute to the in vivo activity of QTsomes.

Applications

Depending on the application, the lipid nanoparticles disclosed herein may be designed to favor characteristics such as increased interaction with nucleic acids, increased serum stability, lower RES-mediated uptake, targeted delivery, or pH sensitive release within the endosome. Because of the varied nature of lipid nanoparticle formulations, any one of the several methods provided herein may be applied to achieve a particular therapeutic aim. Cationic lipids, anionic lipids, PEG-lipids, neutral lipids, fusogenic lipids, aminolipids, cationic polymers, anionic polymers, polymer conjugates, peptides, targeting moieties, and combinations thereof may be applied to meet specific aims.

The lipid nanoparticles described herein can be used as platforms for therapeutic delivery of oligonucleotide (ON) therapeutics, such as siRNA, shRNA, miRNA, anti-miR, and antisense ODN. These therapeutics are useful to manage a wide variety of diseases such as various types of cancers, leukemias, viral infections, and other diseases. For instance, targeting moieties such as cyclic-RGD, folate, transferrin, or antibodies greatly enhance activity by enabling targeted drug delivery. A number of tumors overexpress receptors on their cell surface. Non-limiting examples of suitable targeting moieties include transferrin (Tf), folate, low density lipoprotein (LDL), and epidermal growth factors. In addition, tumor vascular endothelium markers such as alpha-v-beta-3 integrin and prostate-specific membrane antigen (PSMA) are valuable as targets for targeted lipid nanoparticles. In certain embodiments, lipid nanoparticle formulations having particles measuring about 300 nm or less in diameter with a zeta potential of less than 50 mV and an encapsulation efficiency of greater than 20.0% are useful for NA delivery.

Implementation of embodiments of the lipid nanoparticle formulations described herein alone or in combination with one another synergizes with current paradigms of lipid nanoparticle design.

A wide spectrum of therapeutic agents may be used in conjunction with the lipid nanoparticles described herein. Non-limiting examples of such therapeutic agents include antineoplastic agents, anti-infective agents, local anesthetics, anti-allergics, antianemics, angiogenesis, inhibitors, beta-adrenergic blockers, calcium channel antagonists, antihypertensive agents, anti-depressants, anti-convulsants, anti-bacterial, anti-fungal, anti-viral, anti-rheumatics, anthelminithics, antiparasitic agents, corticosteroids, hormones, hormone antagonists, immunomodulators, neurotransmitter antagonists, anti-diabetic agents, anti-epileptics, anti-hemmorhagics, anti-hypertonics, antiglaucoma agents, immunomodulatory cytokines, sedatives, chemokines, vitamins, toxins, narcotics, imaging agents, and combinations thereof.

Nucleic acid-based therapeutic agents are highly applicable to the lipid nanoparticle formulations of the present disclosure. Examples of such nucleic acid-based therapeutic agents include, but are not limited to: pDNA, siRNA, miRNA, anti-miRNA, ASO, and combinations thereof. To protect from serum nucleases and to stabilize the therapeutic agent, modifications to the substituent nucleic acids and/or phosphodiester linker can be made. Such modifications include, but are not limited to: backbone modifications (e.g., phosphothioate linkages); 2' modifications (e.g., 2'-O-methyl substituted bases); zwitterionic modifications (6'-aminohexy modified ODNs); the addition of a lipophilic moiety (e.g., fatty acids, cholesterol, or cholesterol derivatives); and combinations thereof. The modified sequences synergize with the lipid nanoparticle formulations disclosed herein. For example, addition of a 3'-cholesterol to an ODN supplies stability to a lipid nanoparticle complex by adding lipophilic interaction in a system otherwise solely held together by electrostatic interaction. In addition, this lipophilic addition promotes cell permeation by localizing the ODN to the outer leaflet of the cell membrane. Applying a peptide such as gramicidin or JTS-1 further promotes cell permeation of the formulation due to its fusogenic properties. Alternatively, addition of an enzyme such as proteinase K could further aid the ODN in resisting degradation.

Depending on the therapeutic application, the lipid nanoparticles described herein may be administered by the following methods: peroral, parenteral, intravenous, intramuscular, subcutaneous, intraperitoneal, transdermal, intratumoral, intraarterial, systemic, or convection-enhanced delivery. In particular embodiments, the lipid nanoparticles are delivered intravenously, intramuscularly, subcutaneously, or intratumorally. Subsequent dosing with different or similar lipid nanoparticles may occur using alternative routes of administration.

Pharmaceutical compositions of the present disclosure comprise an effective amount of a lipid nanoparticle formulation disclosed herein, and/or additional agents, dissolved or dispersed in a pharmaceutically acceptable carrier. The phrases "pharmaceutical" or "pharmacologically acceptable" refers to molecular entities and compositions that produce no adverse, allergic or other untoward reaction when administered to an animal, such as, for example, a human. The preparation of a pharmaceutical composition that contains at least one compound or additional active ingredient will be known to those of skill in the art in light of the present disclosure, as exemplified by Remington's Pharmaceutical Sciences, 2003, incorporated herein by reference. Moreover, for animal (e.g., human) administration, it will be understood that preparations should meet sterility, pyrogenicity, general safety and purity standards as required by FDA Office of Biological Standards.

A composition disclosed herein may comprise different types of carriers depending on whether it is to be administered in solid, liquid or aerosol form, and whether it need to be sterile for such routes of administration as injection. Compositions disclosed herein can be administered intravenously, intradermally, transdermally, intrathecally, intraarterially, intraperitoneally, intranasally, intravaginally, intrarectally, topically, intramuscularly, subcutaneously, mucosally, in utero, orally, topically, locally, via inhalation (e.g., aerosol inhalation), by injection, by infusion, by continuous infusion, by localized perfusion bathing target cells directly, via a catheter, via a lavage, in cremes, in lipid compositions (e.g., liposomes), or by other method or any combination of the forgoing as would be known to one of ordinary skill in the art (see, for example, Remington's Pharmaceutical Sciences, 2003, incorporated herein by reference).

The actual dosage amount of a composition disclosed herein administered to an animal or human patient can be determined by physical and physiological factors such as body weight or surface area, severity of condition, the type of disease being treated, previous or concurrent therapeutic interventions, idiopathy of the patient and on the route of administration. Depending upon the dosage and the route of administration, the number of administrations of a preferred dosage and/or an effective amount may vary according to the response of the subject. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, an active compound may comprise between about 2% to about 75% of the weight of the unit, or between about 25% to about 60%, for example, and any range derivable therein. Naturally, the amount of active compound(s) in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

In certain embodiments, a composition herein and/or additional agents is formulated to be administered via an alimentary route Alimentary routes include all possible routes of administration in which the composition is in direct contact with the alimentary tract. Specifically, the pharmaceutical compositions disclosed herein may be administered orally, buccally, rectally, or sublingually. As such, these compositions may be formulated with an inert diluent or with an assimilable edible carrier.

In further embodiments, a composition described herein may be administered via a parenteral route. As used herein, the term "parenteral" includes routes that bypass the alimentary tract. Specifically, the pharmaceutical compositions disclosed herein may be administered, for example but not limited to, intravenously, intradermally, intramuscularly, intraarterially, intrathecally, subcutaneous, or intraperitoneally (U.S. Pat. Nos. 6,753,514, 6,613,308, 5,466,468, 5,543, 158; 5,641,515; and 5,399,363 are each specifically incorporated herein by reference in their entirety).

Solutions of the compositions disclosed herein as free bases or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms. The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form must be sterile and must be fluid to the extent that easy injectability exists. It must be stable under the conditions of manufacture and storage and must be preserved against the contaminating action of microorganisms, such as bacteria and fungi. The carrier can be a solvent or dispersion medium containing, for example, water, ethanol, polyol (i.e., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption such as, for example, aluminum monostearate or gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, and intraperitoneal administration. In this connection, sterile aqueous media that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety, and purity standards as required by FDA Office of Biologics standards.

Sterile injectable solutions are prepared by incorporating the compositions in the required amount in the appropriate solvent with various of the other ingredients enumerated above, as required, followed by filter sterilization. Generally, dispersions are prepared by incorporating the various sterilized compositions into a sterile vehicle which contains the basic dispersion medium and the required other ingredients from those enumerated above. In the case of sterile powders for the preparation of sterile injectable solutions, some methods of preparation are vacuum-drying and freeze-drying techniques which yield a powder of the active ingredient plus any additional desired ingredient from a previously sterile-filtered solution thereof. A powdered composition is combined with a liquid carrier such as, e.g., water or a saline solution, with or without a stabilizing agent.

In other embodiments, the compositions may be formulated for administration via various miscellaneous routes, for example, topical (i.e., transdermal) administration, mucosal administration (intranasal, vaginal, etc.) and/or via inhalation.

Pharmaceutical compositions for topical administration may include the compositions formulated for a medicated application such as an ointment, paste, cream or powder. Ointments include all oleaginous, adsorption, emulsion and water-soluble based compositions for topical application, while creams and lotions are those compositions that include an emulsion base only. Topically administered medications may contain a penetration enhancer to facilitate adsorption of the active ingredients through the skin. Suitable penetration enhancers include glycerin, alcohols, alkyl methyl sulfoxides, pyrrolidones and luarocapram. Possible bases for compositions for topical application include polyethylene glycol, lanolin, cold cream and petrolatum as well as any other suitable absorption, emulsion or water-soluble ointment base. Topical preparations may also include emulsifiers, gelling agents, and antimicrobial preservatives as necessary to preserve the composition and provide for a homogenous mixture. Transdermal administration of the compositions may also comprise the use of a "patch." For example, the patch may supply one or more compositions at a predetermined rate and in a continuous manner over a fixed period of time.

In certain embodiments, the compositions may be delivered by eye drops, intranasal sprays, inhalation, and/or other aerosol delivery vehicles. Methods for delivering compositions directly to the lungs via nasal aerosol sprays has been described in U.S. Pat. Nos. 5,756,353 and 5,804,212 (each specifically incorporated herein by reference in their entirety). Likewise, the delivery of drugs using intranasal microparticle resins (Takenaga et al., 1998) and lysophosphatidyl-glycerol compounds (U.S. Pat. No. 5,725,871, specifically incorporated herein by reference in its entirety) are also well-known in the pharmaceutical arts and could be employed to deliver the compositions described herein. Likewise, transmucosal drug delivery in the form of a polytetrafluoroetheylene support matrix is described in U.S. Pat. No. 5,780,045 (specifically incorporated herein by reference in its entirety), and could be employed to deliver the compositions described herein.

It is further envisioned the compositions disclosed herein may be delivered via an aerosol. The term aerosol refers to a colloidal system of finely divided solid or liquid particles dispersed in a liquefied or pressurized gas propellant. The typical aerosol for inhalation consists of a suspension of active ingredients in liquid propellant or a mixture of liquid propellant and a suitable solvent. Suitable propellants include hydrocarbons and hydrocarbon ethers. Suitable containers will vary according to the pressure requirements of the propellant. Administration of the aerosol will vary according to subject's age, weight and the severity and response of the symptoms.

EXAMPLES

Certain embodiments of the present invention are defined in the Examples herein. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

Materials and Methods

Materials 1,2-Dioleyloxy-N,N-dimethyl-3-aminopropane (DODMA) was obtained from Corden Pharma (Boulder, Colo., USA). 1,2-dioleoyl-3-trimethylammonium-propane (DOTAP) and 1,2-dioleoyl-sn-glycero-3-phosphocholine (DOPC) were purchased from Avanti Polar Lipids (Alabaster, Ala., USA). Cholesterol (CHOL) and Cremephor EL were obtained from Sigma Aldrich (St. Louis, Mo., USA). N-(carbonyl-methoxypolyethyleneglycol 2000)-1,2-dipalmitoyl-sn-glycero-3-phosphoethanolamine (DPPE-PEG) was purchased from NOF America Corp. (White Plains, N.Y., USA). The AM-21 sequence, u*c*a*acaucagucugauaag*c*u*a (SEQ ID NO: 1), where lower case letters represent 2'-O-methyl bases and asterisks represent phosphorothioate linkages, was obtained from Alpha DNA (Montreal, Quebec, CA) at desalted purity. PrimeTime qPCR assay primer probes and kits for DDAH1, PTEN, RECK, PDCD4, TIMP3 target genes and GAPDH housekeeping gene were purchased from Integrated DNA Technologies (Coralville, Iowa, USA).

Synthesis of QT

QT were prepared by serial ethanol dilution method. Briefly, all lipids (X/Y/36/20/4 mol/mol, DODMA/DOTAP/DOPC/CHOL/DPPE-PEG) were dissolved in ethanol and combined with an equal volume of AM-21 dissolved in citric acid buffer (20 mM, pH 4.5), maintaining a 10:1, lipid:AM weight ratio. DODMA and DOTAP content were varied with the total molar percent of tertiary and quaternary amine maintained at 40 molar percent composition (X+Y=40). This solution was further diluted by equivalent volumes (1:1) of citric acid buffer, NaCl/NaOH buffer (300 mM NaOH, 20 mM NaOH, pH 7.4), and PBS (10 mM, pH 7.4). The resultant LN solution was concentrated by tangential diafiltration to remove excess ethanol and to reach the appropriate final concentration. Samples were stored at 4° C. prior to characterization.

Mean Particle Diameter and Surface Charge

Aliquots of QT/AM-21 were diluted in PBS. Particle size was measured by dynamic light scattering (DLS) on a NICOMP 370 Submicron Particle Sizer (NICOMP, Santa Barbara, Calif., USA). Aliquots of QT/AM-21 or complexes containing only tertiary or quaternary amine were diluted in citric acid buffer or PBS to demonstrate the pH dependency of surface charge. Zeta potential measurement was conducted on a Zeta PALS Analyzer (Brookhaven Instruments Corp., Worcestershire, N.Y., USA).

Drug Loading and Stability

Encapsulation efficiency was determined by Quant-iT™" Ribogreen RNA assay kit (Life Technologies, Carlsbad, Calif., USA). Briefly, QT/AM-21 complexes were lysed with Triton X-100 and mean fluorescent intensity was compared with intact QT/AM-21 at (480 nm $\lambda_{ex}$, 520 nm $\lambda_{em}$). Relative encapsulation efficiency was determined with the formula:

$$(\%) = (1FI_{without\ Triton\ X-100}/FI_{with\ Triton\ X-100}) \times 100\%.$$

Formulation stability was evaluated at −20, 4, and 25° C. over a period of 30 days. The particle size was periodically monitored by DLS. 10% sucrose was added as a cryoprotectant prior to storage.

Cell culture

A549 cells were purchased from the American Type Culture Collection (Rockville, Md., USA) and grown in RPMI 1640 (Corning, Tewksbury, Mass., USA) supplemented with 10% fetal bovine serum (FBS, Sigma Aldrich, St. Louis, Mo., USA) and 100 units/mL penicillin and 100 mg/mL streptomycin. Cells were maintained at 37° C. and grown under a humidified atmosphere containing 5% $CO_2$.

In Vivo Gene Regulation

Cells were grown in 24-well plates at a density of $7.0 \times 10^5$ cells/well 24 h prior to transfection. QT/AM-21 of varying lipid composition or QT/negative control (NC) were administered at 50 nM in the presence of 20% serum containing media to determine the optimal QT composition. QT/AM-21 was also tested at 1.56, 6.25, 25, and 100 nM to demonstrate dose dependency of treatment. Cells were incubated at 37° C. with transfection media for 4 h and then washed three times with PBS. Fresh complete cell culture media was added and the cells were incubated at 37° C. for an additional 44 h. RNA was isolated from cells by RNeasy 96 kit (Qiagen, Valencia, Calif., USA). qRT-PCR was conducted with Taqman® MicroRNA Assay (Life Technologies) or EXPRESS One-Step Superscript® qRT-PCR kit (Life Technologies) on an Applied Biosystems StepOnePlus™ RT-PCR system (Life Technologies). The relative amount of DNA was calculated and compared according to the $2^{-\Delta\Delta Ct}$ method.

Cell Viability Assay

Cells were grown in 96-well plates at a density of $2.0 \times 10^4$ cells/well. Cells were treated with controls or QT/AM-21 at 50, 100, or 200 nM, with and without PTX (4.1 nM) dissolved in a small volume of 1:1 Cremophor EL:ethanol solution. Relative cell viability was quantified by CellTiter 96® AQueous One Solution Cell Proliferation Assay (Promega, Madison, Wis., USA) according to the manufacturer's protocol 72 h following the start of treatment. Briefly, 20 µL MTS assay solution was added to each well and the plates were incubated for 1 h. The absorbance at 490 nm was recorded to determine cytotoxicity relative to the untreated control.

Migration Assay

A wound healing model was conducted to examine the migratory ability of A549 cells following treatment. A549 cells were plated at a density of $6.0 \times 10^5$ cells/well in a 33 mm petri dish 24 h prior to transfection. A scratch wound across the dish was made using a 10 µL pipet tip immediately before treatment. Culture media was removed and replaced with transfection media containing QT/AM-21 or appropriate controls diluted in complete media. Cells were allowed to proliferate at 37° C. for 48 h. Distances between edges of the wound were measured on a Nikon E800 microscope (Nikon, Tokyo, Japan) and SPOT Advanced Imaging Software (v5.0, Diagnostic Instruments Inc., Sterling Heights, Mich., USA).

Invasion Assay

Matrigel (BD Biosciences, San Jose, Calif., USA) was combined with serum-free RPMI 1640 culture media in a 1:1 ratio. 70 µL of gel was added to each well insert of a 24-well plate. The gel was allowed to set for 1 h at 37° C. A549 cells were seeded at $7.5 \times 10^5$ cells/well in a volume of 100 µL/well on top of the gel in the insert. Transfection media containing various formulations or controls at 2×concentration in a 100 µL volume were added to the top of the well inserts. 500 µL 10% fetal bovine supplemented media was added as a chemoattractant below the transwell insert. The plate was incubated at 37° C. for 48 h. Following the incubation period, cells remaining in the top of the well inserts were removed with a cotton swab. Well inserts were rinsed with PBS and placed in 500 uL 0.25% trypsin solution for 1 h at 37° C. Detached cells were counted on a hemocytometer.

Tumor Regression Analysis

A549 mouse xenograft models were generated by inoculating female athymic nude mice with $1.0 \times 10^6$ cells/mouse. Tumors were allowed to reach a size of $\geq 100$ mm$^3$ before treatment began (~2 weeks). Mice (n=10 per group) were dosed by tail vein injection with saline control, 0.5, or 1 mg/kg QT/AM-21. Tumor progression was routinely monitored through the course of the study. Tumor volume was calculated according to the formula: $V=(L \cdot W^2)/2$. Mice were dosed every three days for the first three treatments and then once a week following the first dose for a total of seven doses. All mice were treated according to the guidelines deemed appropriate by the Institutional Animal Care and Use Committee (IACUC) of the Ohio State University (OSU).

Combination Therapy Analysis

Female athymic nude mice (n=5 per group) were implanted with $1.0 \times 10^6$ A549 cells/mouse and treatment began when tumors reached a size of $\geq 100$ mm$^3$. Mice were treated by tail vein injection with saline control or 1 mg/kg QT/AM-21. Mice receiving PTX treatment as monotherapy or combination therapy received PTX dissolved in 1:1 Cremephor EL:ethanol solution at a dose of 3 mg/kg via intraperitoneal injection. Mice were dosed on days 1, 3, 5, 8, 15, 22, 29 and were monitored over a 4 week period. 48 h following the last dose, mice were euthanized and tumors were collected for gene regulation study.

In Vivo Gene Regulation

Tumors were harvested and placed in TRIzol reagent (Life Technologies) following treatment and homogenized. mRNA was isolated per the manufacturer's protocol. qRT-PCR was then completed according to the same procedure as outlined in the in vitro section.

Statistical Analysis

All studies were done in triplicate unless otherwise mentioned. Statistical analysis was conducted on Microscoft Excel Software (2013, Redmond, Wash., USA). Student's t-test was used to determine statistical significance between two or more groups. p≤0.05 was selected as the cutoff for statistical significance.

Example 1

Increased Expression of Target Genes in "QTsome™" Lipid Nanoparticle Formulation Formulated Anti-miR-21 (AM-21) Treated KB Cell In Vitro KB cells (Hela derivative cancer cells) were cultured in vitro and transfected with free, unformulated AM-21, or "QTsome™" lipid nanoparticle formulation that is formulated with AM-21. Two anti-miR-21 oligonucleotides were used for "QTsome™" lipid nanoparticle formulation and transfection (AM-21a and AM-21b).

```
AM-21a:
                                         (SEQ ID NO: 1)
5'-u*c*a*acaucagucugauaag*c*u*a-3';
and AM-21b:
                                         (SEQ ID NO: 2)
5'-5'-u*c*a*acaucagucugauaag*c*u*a-CHOL-3'.
```

In either AM, all bases are 2'O-methylated. *represent phosphorothioate linkages.

The transfection efficiency was measured and compared. As shown in FIG. 1, "QTsome™" lipid nanoparticle formulation greatly enhance the transfection of AM-21 oligonucleotide into KB cells, where in FIG. 1, the Y-Axis is PTEN expression level (%).

Example 2

Increased Expression of Target Genes in "QTsome™" Lipid Nanoparticle Formulation Formulated Anti-miR-21 (AM-21) Treated Lung Cancer Cells In Vitro Lung cancer A549 cells (human lung adenocarcinoma epithelial cell line) were cultured in vitro as standard cell culture. Cells were cultured in RPMI 1640 media supplemented with 10% FBS and 1% antibiotics/antimycotics in a 5% $CO_2$ atmosphere at 37° C.

The lung cancer A549 cells were then treated with either free, unformulated anti-miR-21 (AM-21, 5'-U*C*A*ACAUCAGUCUGAUAAG*C*U*A-3', SEQ ID NO:3), or "QTsome™" lipid nanoparticle formulation formulated anti-miR-21 (SEQ ID NO:2), QT/AM-21. The untreated A549 cells were used as control.

A549 cells were grown to 70% confluency. Serum-free transfection media containing 100 nM AM-21 was added to cells for 4h. Following transfection, fresh serum-containing culture media was added to cells. AM-21b: 5'-5'-u*c*a*acaucagucugauaag*c*u*a-CHOL-3' (SEQ ID NO. 2) was used.

To confirm the effect of anti-miR-21 treatment on inhibiting miR-21 activity in A549 cells, the expression levels of two target genes of miR-21: RECK and PTEN were measured after AM-21 treatment.

RNA was extracted by TRIzol reagent per manufacturer's protocol. cDNA was generated by Maxima First Strand cDNA synthesis kit per manufacture's protocol. RT-PCR was completed on an Applied Biosystems StepOne Plus system using Luminaris Color HighGreen High ROX qPCR Master Mix according to the manufacturer's protocol. RECK and PTEN mRNA levels were measured relative to GAPDH.

Figure 2A:
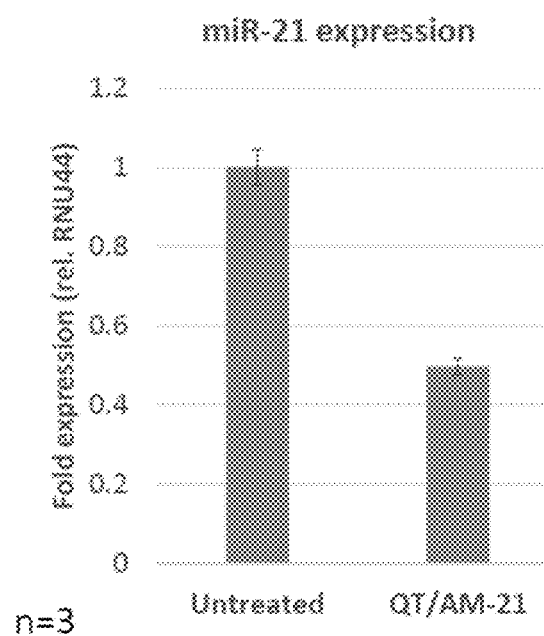
FIG. 2A is a graph showing miR21 expression in untreated and QT/AM-21 treated cells showing down-regulation.
Figure 2B:
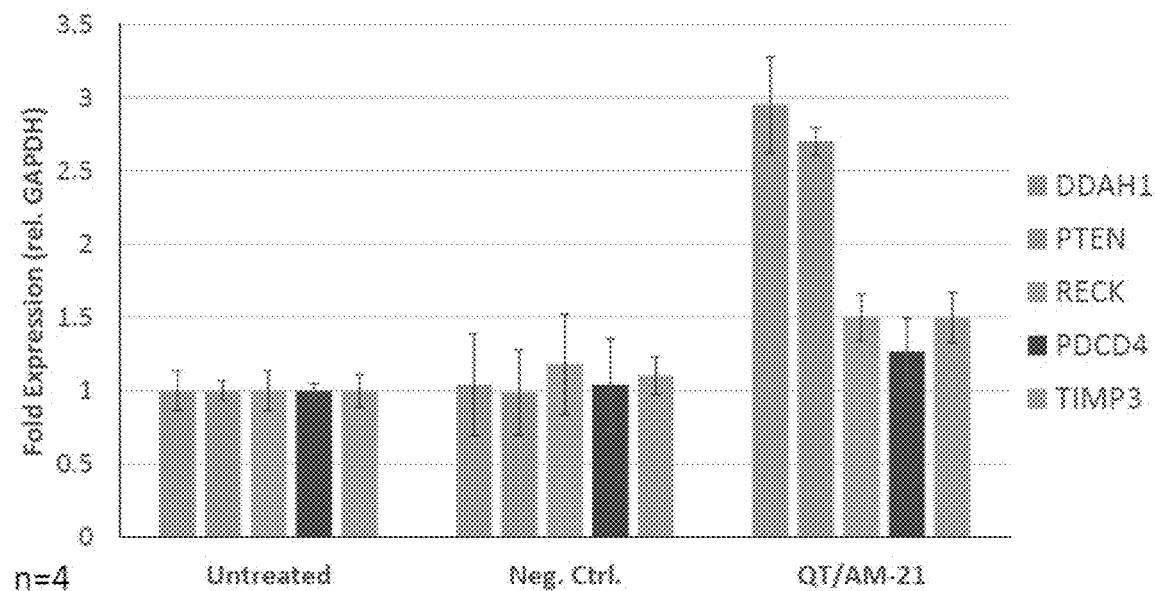
FIG. 2B is a graph that shows target genes (i.e., DDAH1, PTEN, RECK, PDCD$ and TIMP3) de-repression after "QTsome™" lipid nanoparticle formulation formulated anti-miR-21 (QT/AM-21) treatment in A549 lung cancer cells. The composition of "QTsome™" lipid nanoparticle formulation used was: DOTAP/DODMA/DOPC/Cholesterol/PEG-DPPE (15:25:36:20:4 mol/mol). In this composition, DOTAP is a quaternary amine cationic lipid whereas DODMA is tertiary amine cationic lipid.

As shown in FIG. 2A and FIG. 2B, A549 cells (NSCLC) were transfected 4 h with 100 nM AM-21. The level of miR-21 decreased following treatment by over 40%. QT/AM-21 demonstrate over 2.5-fold upregulation for PTEN and DDAH1 and moderate upregulation for RECK, PDCD4, and TIMP3. That is, the expression of RECK in both free AM-21 and QT/AM-21 treated A549 cells is upregulated, and the expression level in QT/AM-21 treated A549 cells is about 2.75 times higher, as compared to the expression in untreated control A549 cells. It is also shown that the expression of PTEN is upregulated about 1.5 times only in QT/AM-21 treated A549 cells. The data indicate anti-miR-21 is effective on inhibiting the activity of anti-miR-21, resulting in increased expression of its target mRNAs. FIG. 2B shows that the upregulation of target genes occurs in a dose dependent manner for DDAH1, PTEN, and RECK.

Figure 3A:
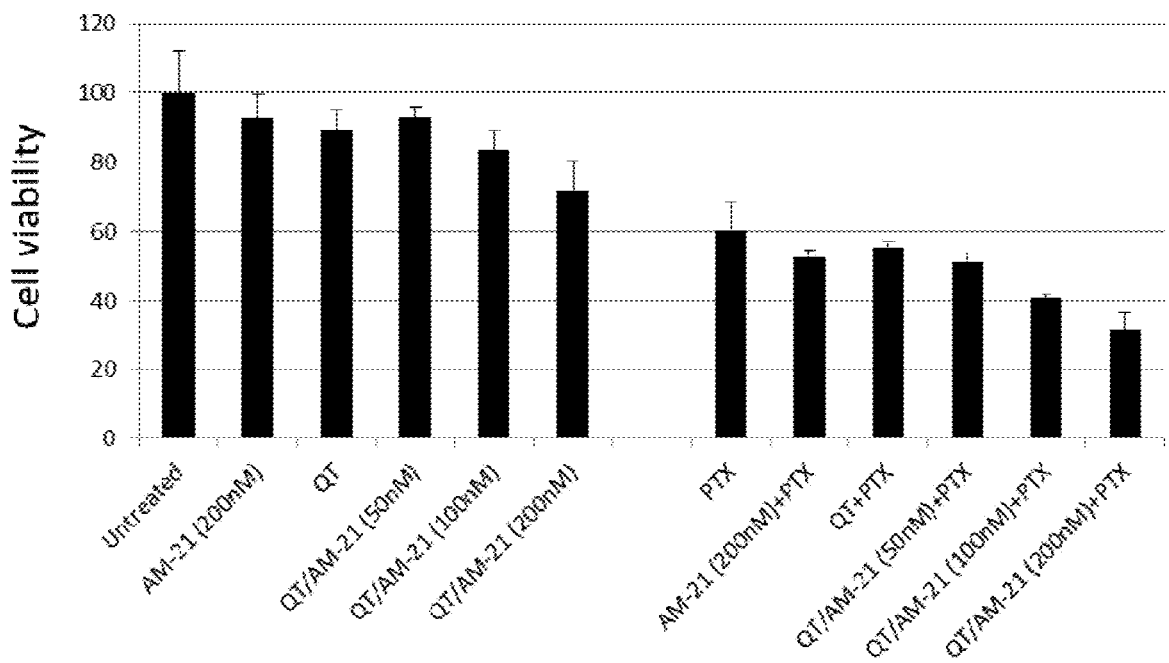
FIG. 3A and FIG. 3B are graphs showing the cell viability after the treatment of: AM-21 (200 nM), QT, QT/AM-21 (50 nM, 100 nM, 200 nM)), paclitaxel (PTX), or the combination of PTX and QT/AM-21.

Thus, treatment with 100 nM QT/AM-21 resulted in moderate to strong down regulation of miR-21 and upregulation of its gene targets (FIG. 3A, FIG. 2B). Relative to the untreated control, miR-21 in the treated group decreased by 50.3±2.1% following administration of QT/AM-21. Little to no effect on target gene regulation was observed for the scrambled NC group. Tumor suppressors PTEN and PDCD4 were upregulated 2.7 and 1.3-fold respectively. Matrix metalloprotease inhibitors RECK and TIMP3 were both upregulated by approximately 1.5-fold. Migration inhibitors ANKRD46 and DDAH1 were upregulated 1.2 and 3.0-fold respectively.

Figure 2C:
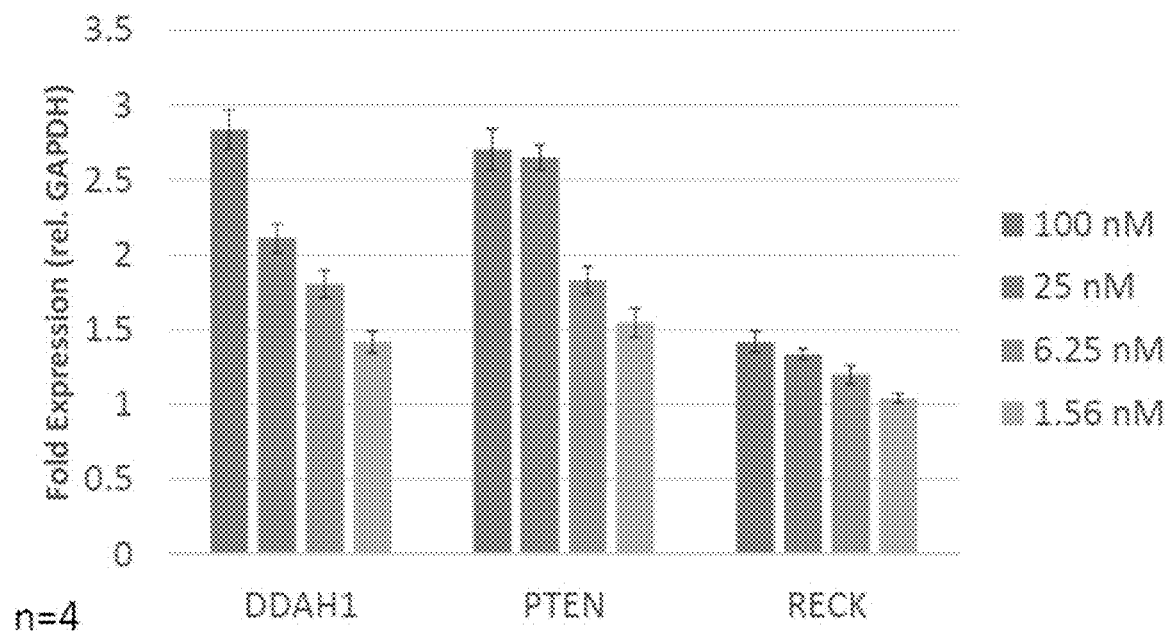
FIG. 2C is a graph showing dose dependent derepression ofmiR-21 targets DDAH1, PTEN and RECK.

FIG. 2C shows dose dependency results where varying dosages of QT/AM-21 between 1.56 to 100 nM were administered and qRT-PCR was conducted to evaluate the relationship between AM concentration and miR-21 target gene upregulation. DDAH1, PTEN, and RECK all demonstrated a direct correlation between dose and response. DDAH1 and PTEN were relatively more sensitive to changes in concentration relative to RECK.

Example 3

Synergistic Effects of QT/AM-21 with other Anti-cancer Treatments

A549 cells were cultured as in Example 2, and treated with either QT/AM-21 (5'-U*C*A*ACAUCAGUCUGAUAAG*C*U*A-3', SEQ ID NO:3) at three different concentrations (50 nM, 100 nM or 200 nM), paclitaxel (PTX) or a combination of PTX and QT/AM-21 (PTX/50 nM QT/AM-21; PTX/QT/100 nM-21; TX/200 nM QT/AM-21). (Dosage of PXT was 4nM).

The cells were incubated with the drugs for 72 h; after which the cells were harvested and tested for cytotoxicity and viability using MTS assay kit by Promega. Absorbance scanning was done at 490 nm to determine relative cell viabilities.

The data show that free, unformulated AM-21 and "QTsome™" lipid nanoparticle formulation do not confer significant cytotoxicity. Only the higher concentration (200 nM QT/AM-21) treatment generates some degree of cytotoxicity.

Figure 3B:
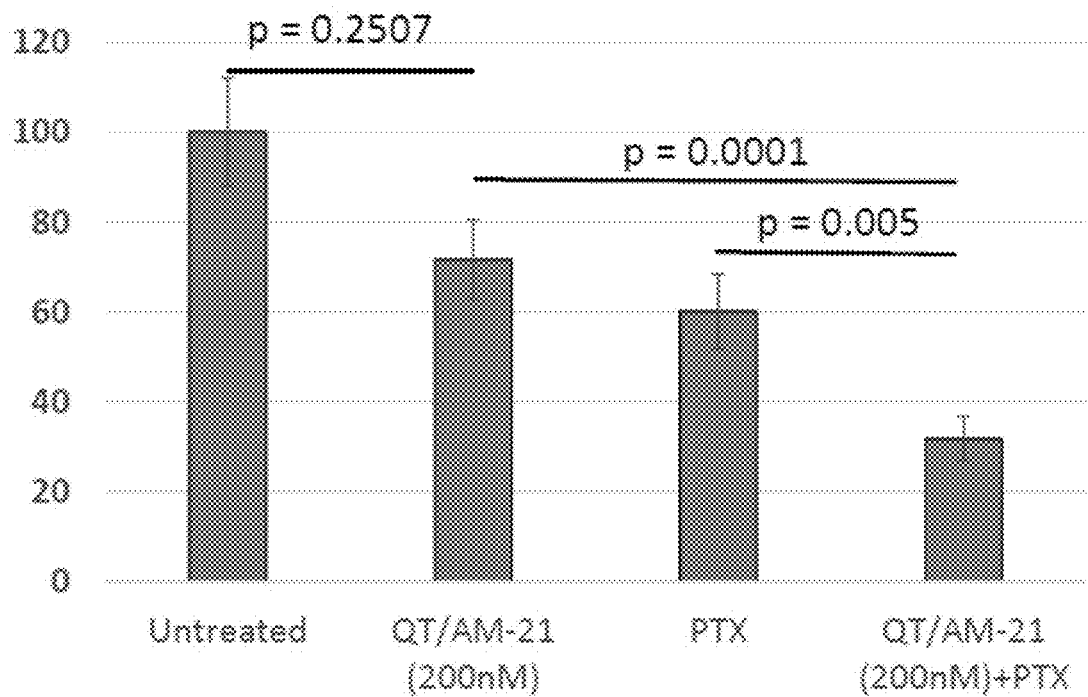

As shown in FIG. 3A and FIG. 3B, about 70% and 65% of cancer cells treated with 200 nM QT/AM-21 and PTX respectively, as compared to the untreated control cancer cells, are still alive, while the effect of the combined treatment with QT/AM-21 and PTX is statistically significantly stronger than either individual treatment ($p<0.05$), leading only about 35% of cells alive after the treatment. These data show that QT/AM-21 is capable of increasing the chemosensitization in cancer cells, e.g., lung cancer cells.

Figure 3C:
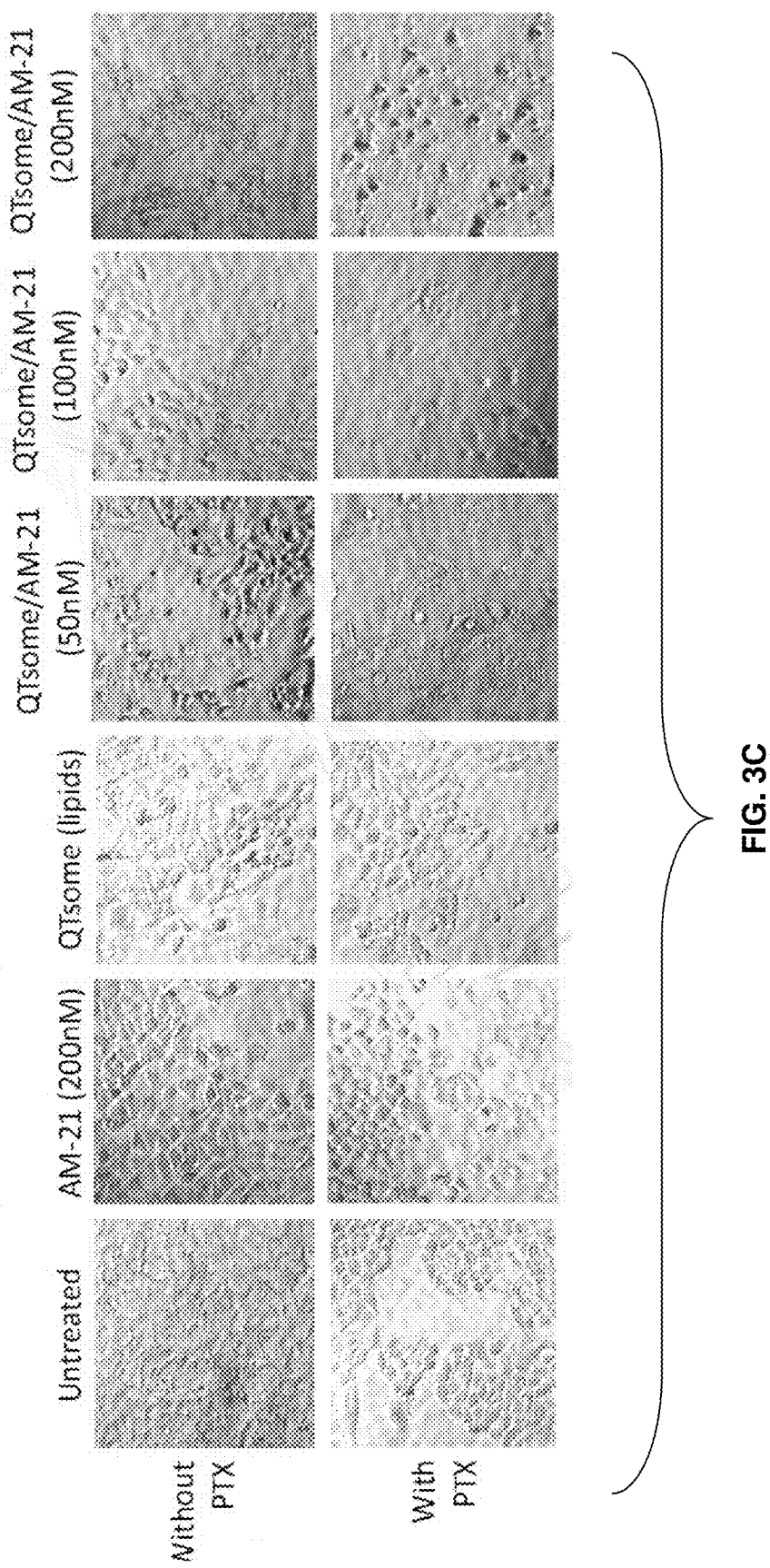
FIG. 3C is a set of photographs showing paclitaxel (PTX) chemo-sensitivity data for untreated, and cells treated with anti-miR21 (AM-21) (200 nM); "QTsome™" lipid nanoparticle formulation (lipids), "QTsome™" lipid nanoparticle formulation/AM-21 (50 nM); "QTsome™" lipid nanoparticle formulation/AM-21 (100 nm); and "QTsome™" lipid nanoparticle formulation/AM-21 (200 nM).

FIG. 3C is a set of photographs showing sensitivity data with and without paclitaxel (PTX) for untreated, anti-miR21 (AM-21) (200 nM); "QTsome™" lipid nanoparticle formulation (lipids), "QTsome™" lipid nanoparticle formulation/AM-21 (50 nM); "QTsome™" lipid nanoparticle formulation/AM-21 (100 nm); and "QTsome™" lipid nanoparticle formulation/AM-21 (200 nM). The combination of PTX and QTsome™/AM-21 results in substantial gains of cytotoxicity, as indicated by the changes in cellular morphology.

Thus, FIGS. 3A-3C show cell viability where treatment with free AM-21 or QT lipids did not result in significant cytotoxicity as analyzed by MTS assay (FIG. 3A). Likewise, the combination of QT/AM-21 at 50 nM did not demonstrate much cytotoxicity. However, moderate increases in cytotoxicity were observed at increased concentrations of QT/AM-21 (100, 200 nM). Addition of PTX alone diminished cell viability by 40%. Addition of free AM-21 or QT lipids to PTX did not result in significant decreases in cell viability. However, substantial gains in cytotoxicity were attributed to the addition of QT/AM-21 at increasing doses. Cell viability was reduced to 51.2%, 41.0%, and 31.8% for 50, 100, and 200 nM doses, respectively. The difference between untreated and QT/AM-21 groups was not significant, but differences between the QT/AM-21 and PTX monotherapies and the combination therapy had $p<<0.05$. Changes in cell morphology were also noted by microscopy, as seen in FIG. 3B. Minor changes in cellular morphology were observed for control treatment groups and for low doses of QT/AM-21. Major alterations in morphology were observed corresponding to increasing cytotoxicity for increasing doses of QT/AM-21 and especially QT/AM-21 with PTX.

Example 4

QT/AM-21 Inhibits miR-21 in the KB Cell Subcutaneous Xenograft

Figure 4A:
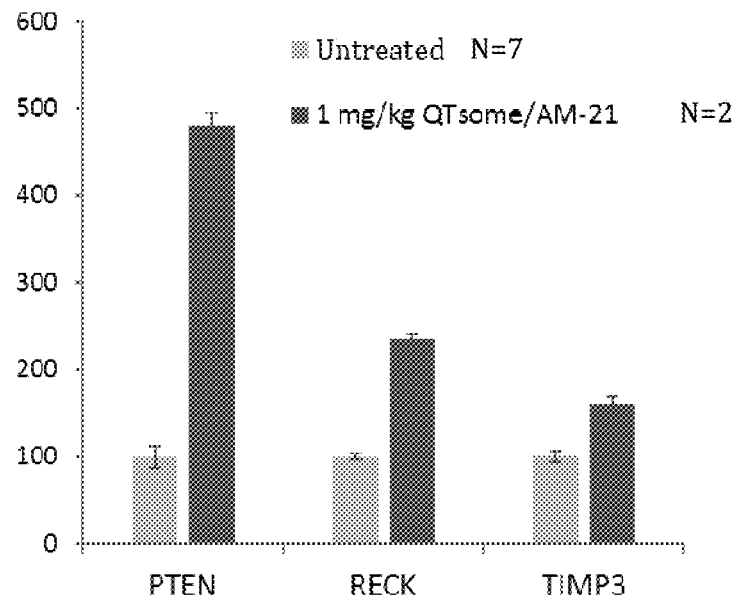
FIG. 4A is a graph that shows target genes (i.e., PTEN, RECK and TIMP3) de-repression after "QTsome™" lipid nanoparticle formulation of anti-miR-21 (AM21) treatment in KB cell subcutaneous xenograft.

Mice (Athymic Ncr-nu/nu) were inoculated subcutaneously with KB cell to establish KB subcutaneous xenograft tumor models. Mice were inoculated with $1\times10^6$ cells/mouse. Mice were allowed to develop over a two week period prior to treatment. Mice with developed tumor at certain size (about 50mm$^3$) were administered with four doses of 2 mg/kg QT/AM-21 (N=2) (days 1, 3, 7 and 10) by intravenous (i.v.) injection. After treatment, tumor tissues were dissected and the expression levels of PTEM, RECK and TIMP3 were measured. The expression levels of all the three genes in QT/AM-21 treated mice are increased, as compared to their expression levels in the untreated mice (N=7), as shown in FIG. 4A.

Figure 4B:
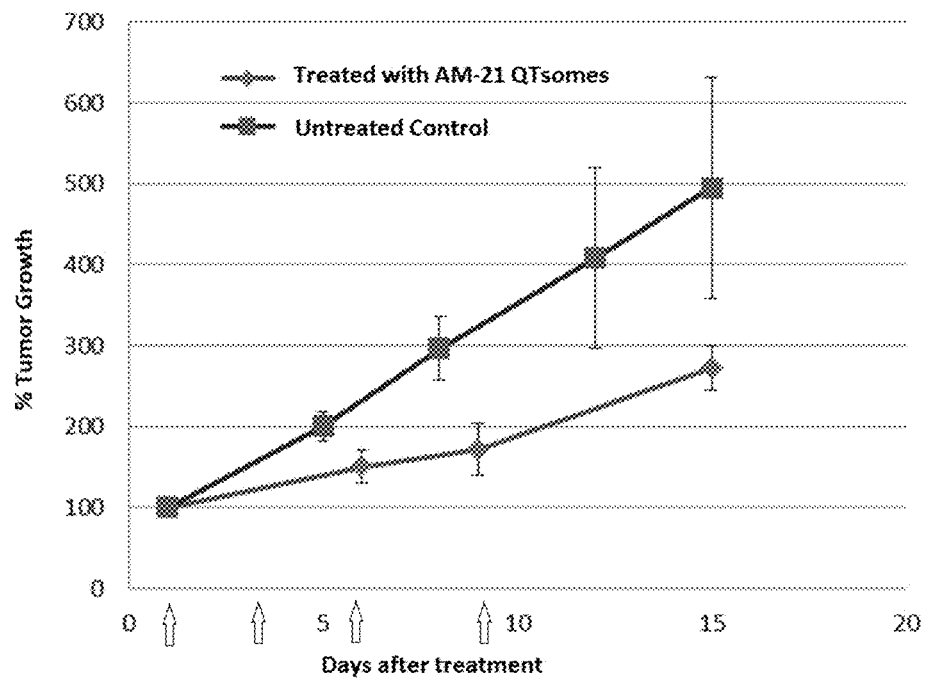
FIG. 4B is a graph showing the measurement of tumor growth after treatment with "QTsome™" lipid nanoparticle formulation of anti-miR-21, showing treatment in KB cell subcutaneous xenograft.

During the course of treatment, tumor growth was measured and compared between the QT/AM-21 treated mice and control mice. The data in FIG. 4B show significant inhibition of tumor growth in QT/AM-21 treated mice ($p<0.05$).

Example 5

QT/AM-21 Induces Tumor Regression in A549 Subcutaneous Xenograft

Mice (Athymic Ncr-nu/nu) were inoculated subcutaneously with A549 cells to establish subcutaneous xenograft tumor models. Mice were inoculated with $1\times10^6$ cells/mouse. Mice were randomized into two groups of seven when tumor volume reached more than 50 mm$^3$ (about two weeks after implantation of A549 cancer cells). QT/AM-21 was administered to mice (N=7) at 2 mg/kg by i.v. injection three times in the first week (days 1, 4 and 7) and once a week thereafter (days 14 and 21). Tumor volumes from treated and untreated (N=7) mice were then measured every other days, as shown in FIG. 5A. Significant decrease in tumor size is achieved through treatment with QTsome™/AM-21 (1 mg/kg)

Figure 5D:
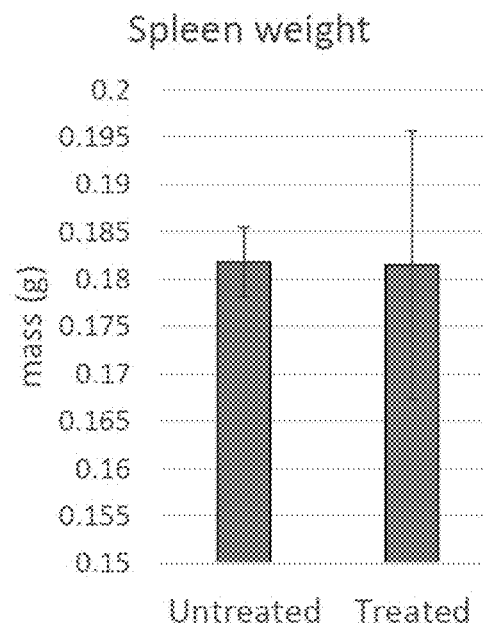
FIG. 5D is a graph showing the endpoint measurements of spleen weights in QT/AM-21 treated A549 subcutaneous xenograft mice.
Figure 5E:
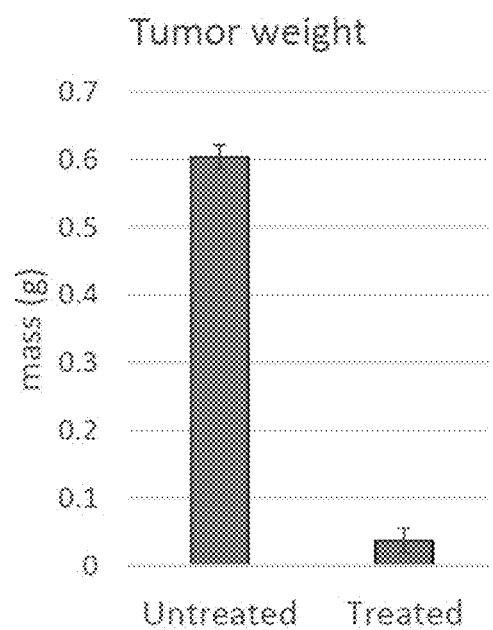
FIG. 5E is a graph showing the endpoint measurements of tumor weights in QT/AM-21 treated A549 subcutaneous xenograft mice.

The data show that QT/AM-21 treatment induces tumor regression in A549 subcutaneous xenograft model. Furthermore, tumors from QT/AM-21 treated mice (N=3) and control mice (N=7) were weighted at the end of treatment (day 24). The tumor weight from QT/AM-21 treated mice is significantly lighter than that from control mice ($p<0.00001$), as shown in FIG. 5E. Except for the differences in tumor weight, no significant differences were observed between untreated control mice and QT/AM-21 treated mice in terms of liver (p=0.5360) (FIG. 5C), and spleen (p=0.9832) weight (FIG. 5D). Only moderate degree of difference in body weight is observed between two groups (p=0.0468), as shown in FIG. 5B.

Figure 5F:
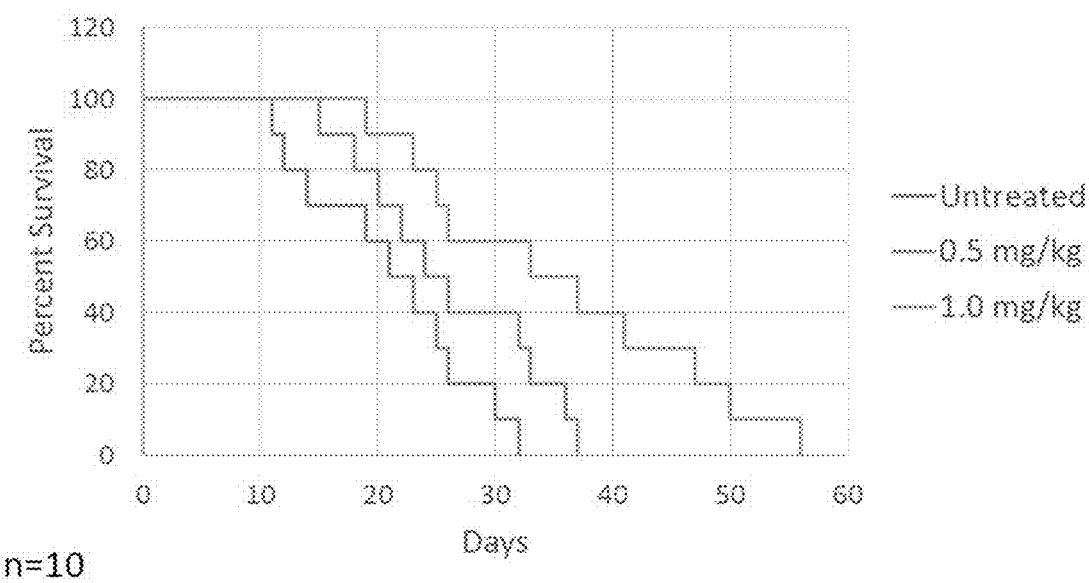
FIG. 5F is a graph showing the Kaplan-Meier survival, as for untreated, and QT/AM-21 (0.5 mg/kg, 1.0 mg/kg) treated xenograft mice.

FIG. 5F shows the Kaplan-Meier survival, as for untreated, and QT/AM-21 (0.5 mg/kg, 1.0 mg/kg). Treatment with 1 mg/kg QT/AM-21 substantially increases survival time of A549 xenograft mice.

Figure 5G:
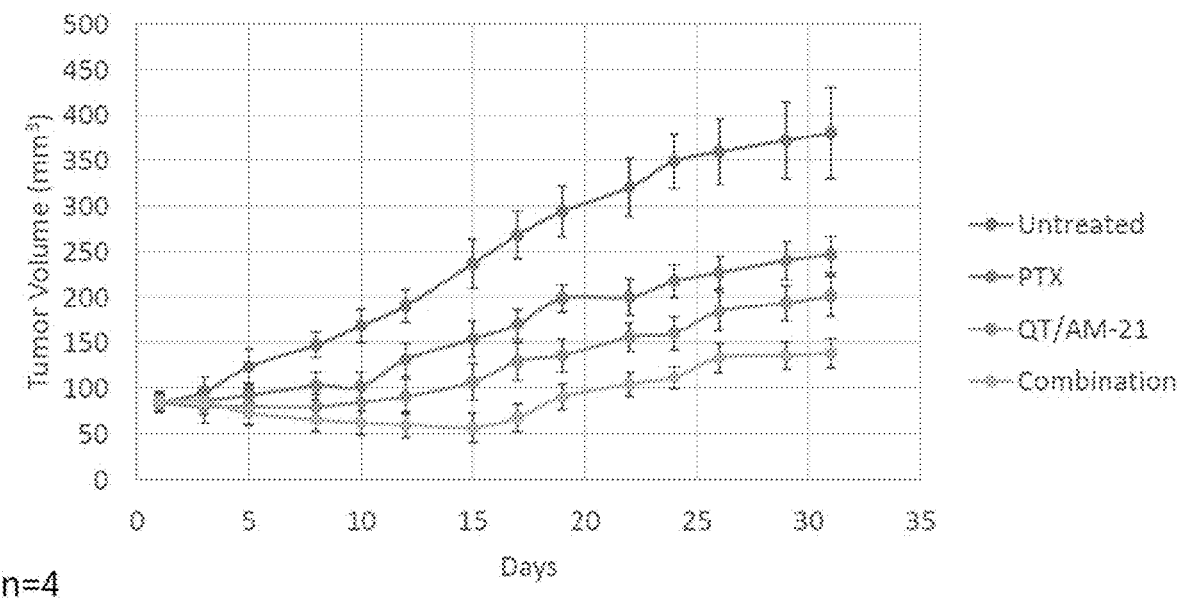
FIG. 5G is a graph showing a combination therapy protocol, showing tumor volume (mm$^3$) for untreated, PTX, QT/AM-21 and a combination of PTX+QT/AM-21 treated xenograft mice.

In a combination therapy protocol, mice were given 1 mg/kg QT/AM-21 and/or 3 mg/kg PTX. As seen in FIG. 5G, treatment with a combination of PTX and QT/AM-21 is able to achieve greater tumor suppression than either agent administered as monotherapy.

Figure 5H:
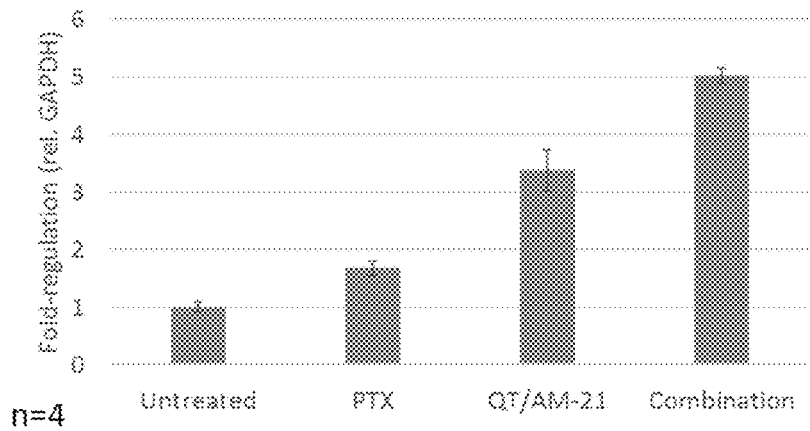
FIG. 5H is a graph showing in vivo gene regulation of DDAH1, fold-regulation (rel. GAPDH) in tumors for untreated, PTX, QT/AM-21 and a combination of PTX+QT/AM-21 treated xenograft mice.
Figure 5I:
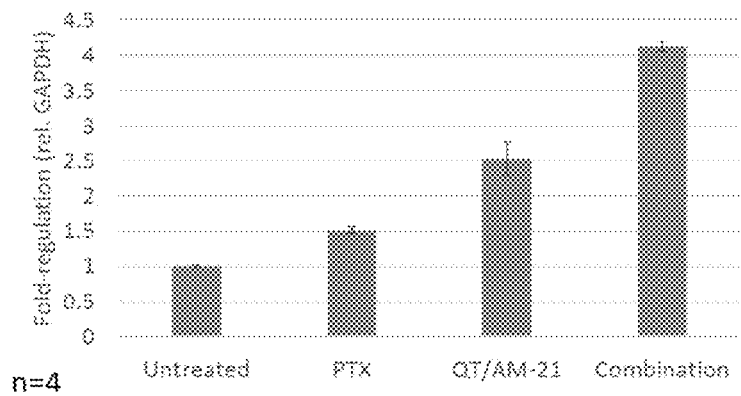
FIG. 5I is a graph showing in vivo gene regulation of PTEN, fold-regulation (rel. GAPDH) in tumors for untreated, PTX, QT/AM-21 and a combination of PTX+QT/AM-21 treated xenograft mice.

In vivo gene regulation of DDAH1 and PTEN are shown in FIG.5H and FIG. 5I, respectively. Treatment with PTX achieves moderate upregulation of DDAH1 and PTEN, while QT/AM-21 brings about strong upregulation. The combination of PTX and QT/AM-21 result in greater gene upregulation than treatment with either agent alone.

In sum, the QTsome™ lipid nanoparticle formulations exhibit small particle size, moderate zeta potential, high drug loading, and long term stability. In vitro analyses indicate strong, dose-dependent upregulation of miR-21 targets as well as increased sensitivity to paclitaxel and reduced migration and invasion with QT/AM-21 treatment. In vivo analyses reveal tumor regression, upregulation of target genes, enhanced anticancer activity with combination therapy, and prolonged survival.

Thus, treatment with QT/AM-21 demonstrates strong anti-tumor activity (FIG. 5A) at 1 mg/kg, but diminished activity at 0.5 mg/kg. Treatment of tumors initiated at ~180 mm$^3$ and ended at 816.75, 618.125, and 172.5 mm$^3$ for the untreated, 0.5 mg/kg, and 1 mg/kg groups respectively. Moderate differences in terms of body weight were observed between the treated and untreated groups, with a difference of about 1.5 g. Liver and spleen weights remained fairly consistent between the two groups, suggesting little to no toxicity for these organs. Tumor weight was over 16-fold lower for the treated group compared to the untreated group (FIGS. 5B-5E). In terms of median survival time, the untreated group was 21 days, the 0.5 mg/kg treated group was 24 days, and the 1 mg/kg treated group was significantly prolonged, at 33 days (FIG. 5F).

With respect to in vivo combination therapy, PTX and QT/AM-21 combination therapy was evaluated for therapeutic efficacy. Treatment began when tumors reached ~80 mm$^3$ in volume. Tumors progressed to 380, 246.4, 201.1, and 138.1 mm$^3$ for the untreated, PTX, QT/AM-21, and combination treatment groups respectively (FIG. 5G). Furthermore, qPCR conducted on tumor sections revealed moderate to strong upregulation of DDAH1 and PTEN (FIG. 5I). DDAH1 and PTEN were only modulated slightly by PTX, 1.7 and 1.5-fold respectively. DDAH1 was upregulated 3.4-fold while PTEN was upregulated 2.5-fold with QT/AM-21. DDAH1 was strongly upregulated by 5-fold and PTEN was upregulated 4.1-fold with the combination therapy.

Example 6

QT/AM-21 Reduces Migration and Invasion of A549 Cells In Vitro

A549 cells were cultured following standard culture procedure and incubated with QT/AM-21 (5'-U*C*A*ACAUCAGUCUGAUAAG*C*U*A-3', SEQ ID NO:3) at three different concentrations (50 nM, 100 nM and 200 nM), or free, unformulated AM-21 (200 nM) for 48 hours. The untreated cells and cells treated with empty "QTsome™" lipid nanoparticle formulation were used as control. The migration of tumor cells was determined. The result demonstrates that QT/AM-21 treatment reduces tumor cell migration, as shown in FIG. 6A.

Figure 6A:
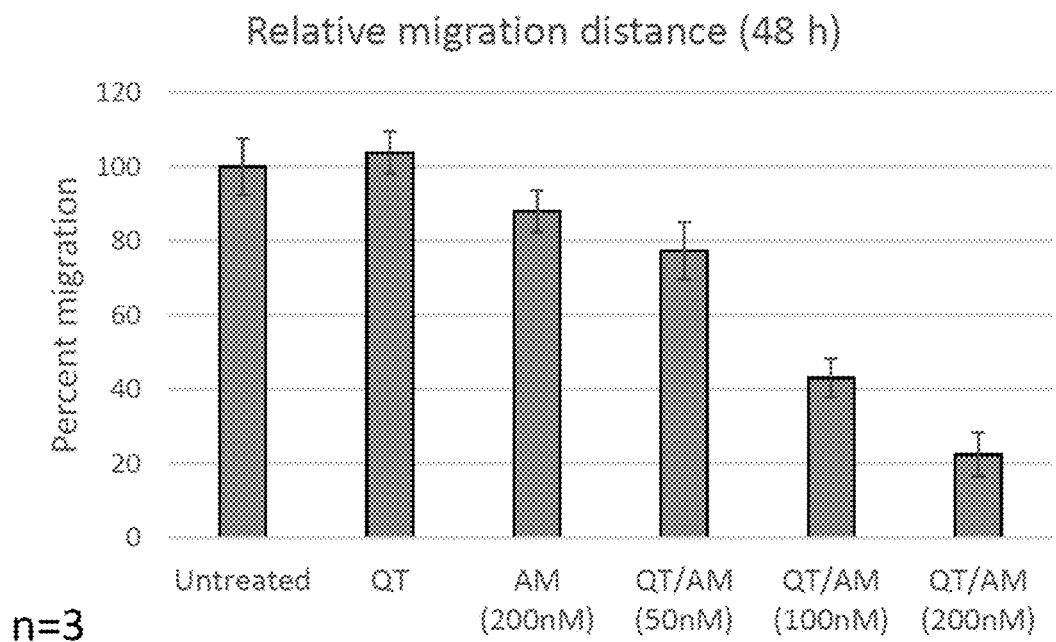
FIG. 6A is a representative histogram that depicts the reduced percent migration of A549 tumor cells after QT/AM-21 treatment for 48 hours.
Figure 6B:
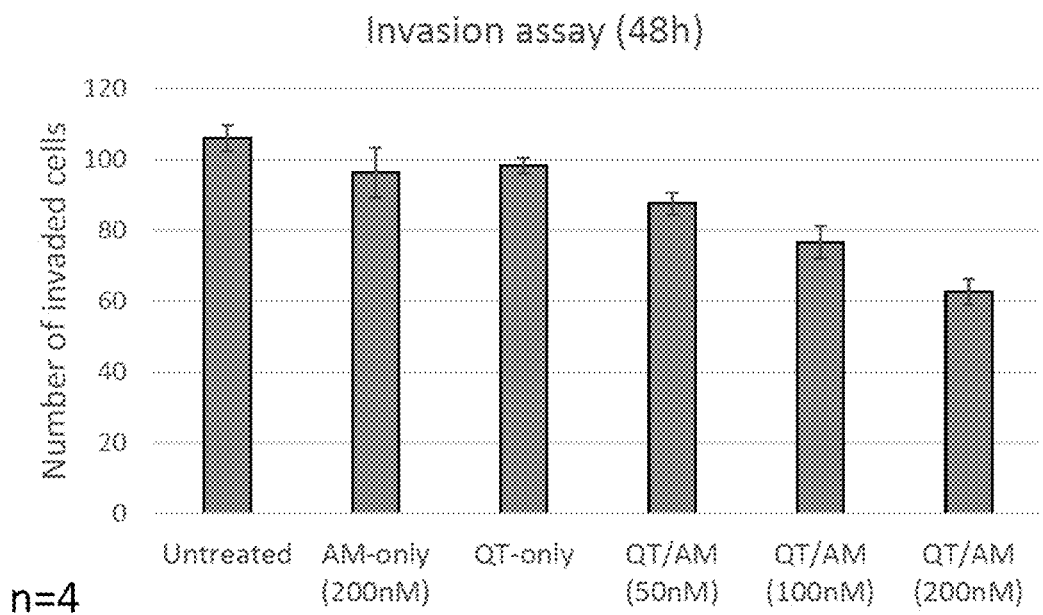
FIG. 6B is graph showing the reduced number of invaded A549 cells in the matrigel invasion assay after QT/AM-21 treatment for 48 hours.

The invaded tumor cells in QT/AM-21 treated culture are significant lower, as compared to the untreated cells or cells only treated with empty "QTsome™" lipid nanoparticle formulation lipid nanoparticles (about 60 Vs about 100) (Number of cells passing through the gel coating), as shown in FIG. 6B.

The data also show that QT/AM-21 is dose dependent as higher treatment level generates a more significant effect on both cell migration and invasion (FIG. 6A and FIG. 6B). (Note: the AM-21 used in Examples was: 5'-U*C*A*ACAUCAGUCUGAUAAG*C*U*A-3', (SEQ ID NO:3) where the sequence contains phosphorothioate linkages (*)).

Thus, the in vitro scratch wound healing assay shows the relative mobility of A549 following treatment with AM-21. QT lipids or AM-21 alone did not confer significant decreases in cell migration in the wound region. With 100 and 200 nM treatment, mobility was reduced to 43.0 and 22.2% relative to the untreated control (FIG. 6A). Matrigel is often used to simulate biological conditions of the basement membrane. The ability of cancer cells to migrate plays a role in determining metastatic potential and increases with cancer progression. Treatment with QT/AM-21 at 50, 100, and 200 nM were able to reduce migration to 87.7, 76.7, and 62.6% respectively, while QT lipids or AM-21 did not significantly retard cell invasion (FIG. 6B).

Example 7

QTSome Formulations

"QTsome™" lipid nanoparticle formulation can significantly increase the effect of AM-21 on the reduction of tumor cell migration, as compared to the free, unformulated AM-21.

A matrigel invasion assay was also performed after 48 hour treatment, as follows: Chilled Matrigel was combined with chilled serum-free RPMI 1640 culture media in a 1:1 ratio. 70 uL of gel was added to each well insert of a 24-well plate. The gel was allowed to set for 1 hour at 37° C. A549 cells were seeded at 75,000 cells/well in a volume of 100 uL/well on top of the gel. Transfection media containing various formulations or controls at 2×concentration in a 100 uL volume were added to the well inserts. The plate was incubated at 37° C. for 48 hours. Following the incubation period, cells remaining in the top of the well inserts were removed with a cotton swab. Well inserts were rinsed with PBS and placed in 500 uL 0.25% trypsin solution for 1 hour at 37° C. Detached cells were counted on a hemocytometer.

Figure 7:
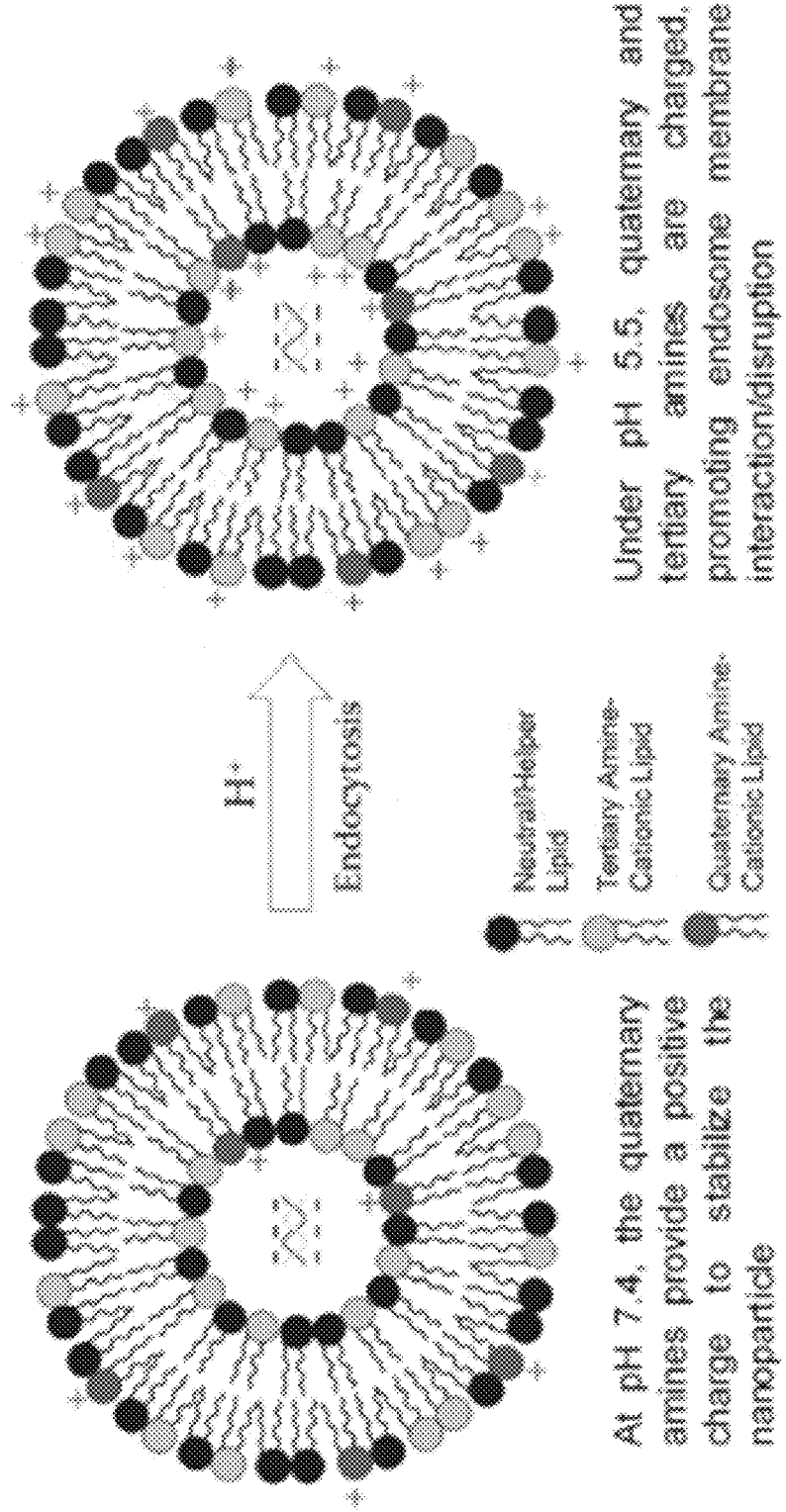
FIG. 7 is a schematic illustration of a "QTsome™" lipid nanoparticle formulation mechanism of action.

FIG. 7 depicts the "QTsome™" lipid nanoparticle formulation mechanism of action. Under pH 7.4, quaternary amine-cationic lipids (QA-CLs) maintain "+" charge to provide stability. Under pH 5.5, both QA-CLs and tertiary amine-cationic lipids (TA-CLs) are charged, which promotes endosome membrane interaction/disruption.

Figure 8:
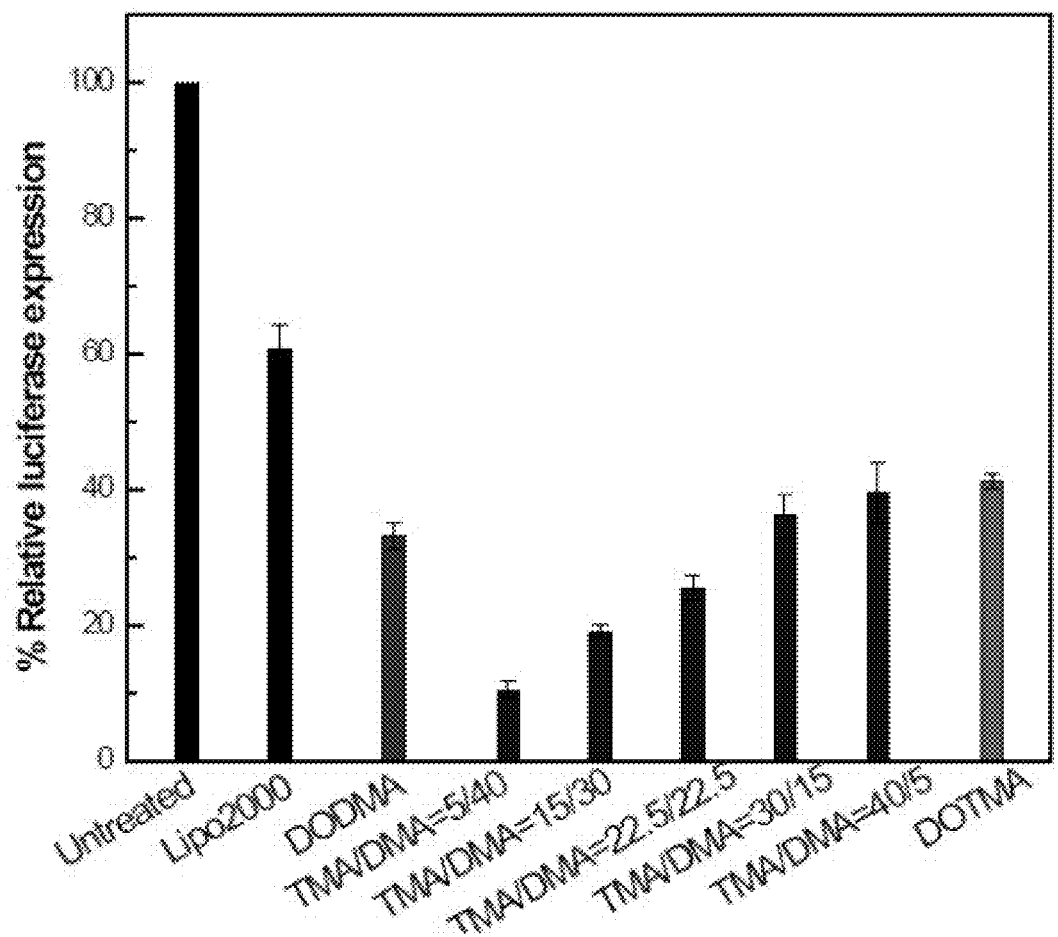
FIG. 8 is a graph showing: down regulation of luciferase expression in SK-HEP-1 cells. Cells expressing luciferase were treated with luciferase-specific siRNA delivered by lipid nanoparticles comprising several different combinations of tertiary amine (DODMA, DMA) and quaternary amine (DOTMA, TMA), ("QTsome™" lipid nanoparticle formulation). Lipofectamine 2000 (Lipo2000) is used as a positive control. Luciferase activity is expressed as a percentage relative to untreated cells.

FIG. 8 depicts the relative luciferase expression of combinations of tertiary and quaternary cationic lipids. At a Q-to-T amine-cationic lipid ratio of 5:40, over 85% downregulation is demonstrated for luciferase siRNA transfection in HCC cells expressing luciferase. For the development of "QTsome™" lipid nanoparticle formulation, lipid stock solutions were created by dissolving lipids in 100% ethanol. All lipids were obtained from Avanti Polar Lipids (USA) or Sigma Aldrich (USA) and used without further purification. Lipids (egg phosphatidylcholine: cholesterol: TPGS, 15:35: 5) were combined with varying concentrations of tertiary (DODMA) and quaternary (DOTMA) amine (45:0, 5:40, 15:30, 22.5:22.5, 30:15, 40:5, 45:0; DODMA:DOTMA) in 1.0 mL vials. Additional ethanol was added to reach a volume of 180 μL. This was then combined with 420 μL 10 mM citric acid buffer to reach a final concentration of 30% ethanol. The formulations were combined with SILENCER Firefly Luciferase (GL2+GL3) siRNA (Invitrogen) at an amine to phosphate (N:P) ratio of 15:1. Formulations were allowed to incubate for 15 minutes prior to dilution with serum-free DMEM (GIBCO) to a total volume of 300 μL. Lipofectamine 2000 (Invitrogen) was used as a positive control and combined with the same amount of siRNA at the same N:P and diluted to the same total volume.

SK-HEP-1 (hepatocellular carcinoma) cells expressing luciferase, grown in DMEM medium at 37° C. under 5% $CO_2$ atmosphere, were plated 24 h prior to transfection at a density of 2×10$^4$ cells per well in a 96-well plate. Cells were grown to approximately 80% confluency and the serum containing media was removed. Cells were transfected with 70 μL transfection media and treated for 4 h. Experiments were performed with four replicates. After treatment was completed, cells were washed with 1X PBS and serum-containing DMEM was restored. 48 h after treatment was completed, cells were analyzed for luciferase expression by a Luciferase Assay Kit (Promega) per the manufacturer's instructions. The results are shown in FIG. 8. The most efficacious transfection activity was exhibited by the formulation containing 5% DOTMA and 40% DODMA, showing over 85% knockdown in luciferase expression.

Figure 9:
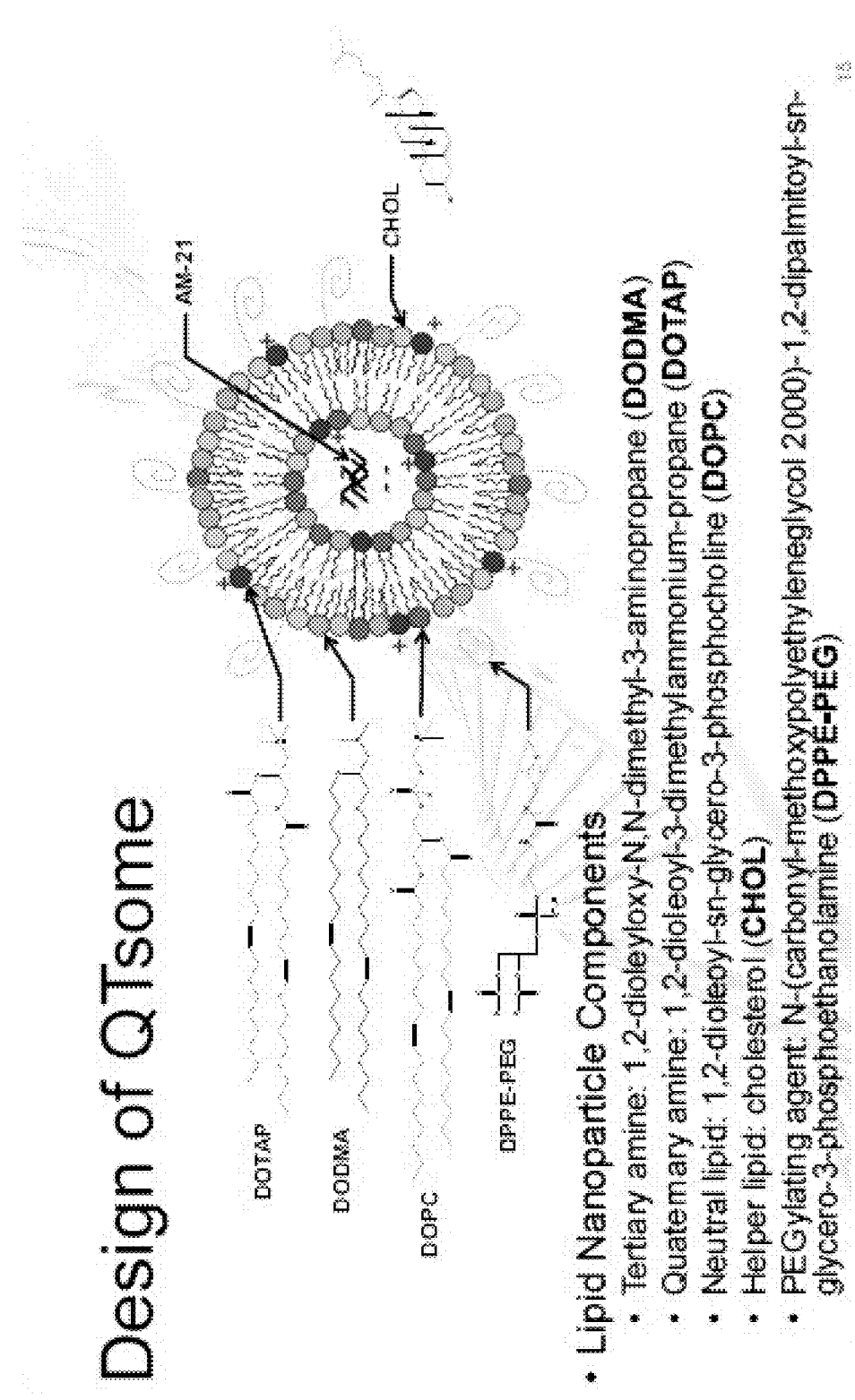
FIG. 9 is a schematic illustration showing a design of "QTsome™" lipid nanoparticle formulation with a list of lipid nanoparticle components:
  tertiary amine: 1,2-dioeyloxy-N,N-dimethyl-3-aminopropane (DODMA);
  quaternary amine: 1,2-dioleoyl-3-dimethylammonium-propane (DOTAP);
  neutral lipid: 1,2-dioleoyl-sn-glycero-3-phosphocholine (DOPC);
  helper lipid: cholesterol (CHOL); and
  PEGylating agent: N-(carbonyl-methoxypolyethyleneglycol 2000)-1,2-dipalmitoyl-sn-glycero-3-phosphoethanolamine (DPPE-PEG).

FIG. 9 is a schematic illustration showing a design of "QTsome™" lipid nanoparticle formulation with a list of lipid nanoparticle components: tertiary amine: 1,2-dioeyloxy-N,N-dimethyl-3-aminopropane (DODMA); quaternary amine: 1,2-dioleoyl-3-dimethylammonium-propane (DOTAP); neutral lipid: 1,2-dioleoyl-sn-glycero-3-phosphocholine (DOPC); helper lipid: cholesterol (CHOL); and PEGylating agent: N-(carbonyl-methoxypolyethyleneglycol 2000)-1,2-dipalmitoyl-sn-glycero-3-phosphoethanolamine (DPPE-PEG).

Figure 10A:
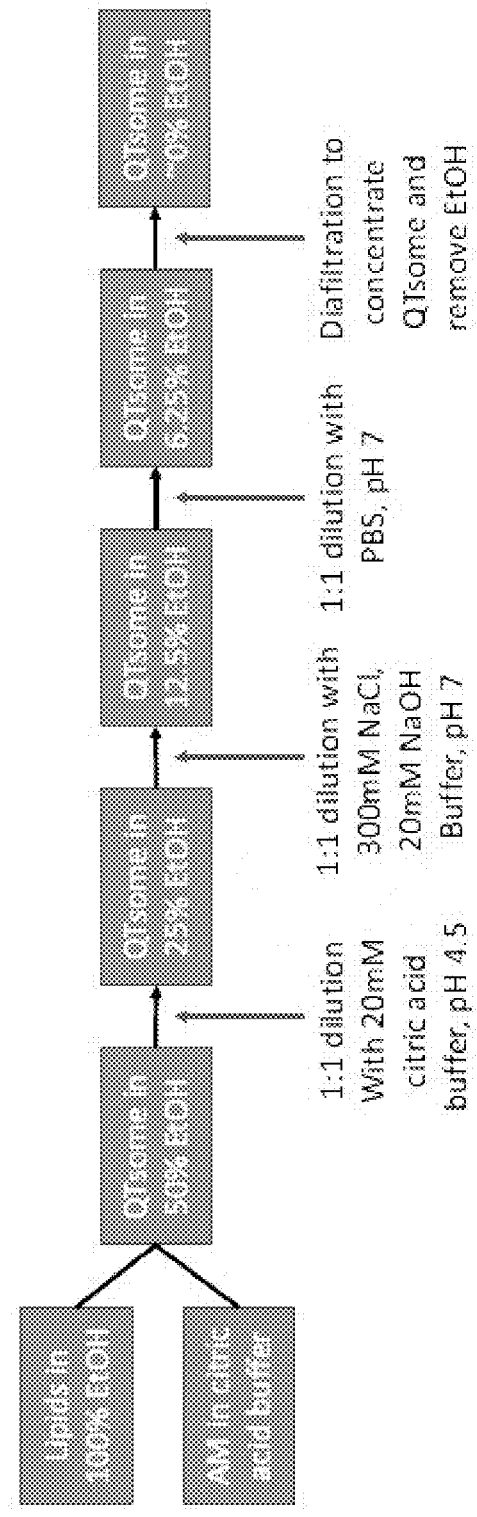
FIG. 10A is a schematic illustration of an example of synthesis of a "QTsome™" lipid nanoparticle formulation.

FIG. 10A is a schematic illustration of an example of synthesis of "QTsome™" lipid nanoparticle formulation, as follows:

In a first step, lipids in 100% EtOH and anti-miR (AM) in citric acid buffer are combined to form "QTsome™" lipid nanoparticle formulation in 50% EtOH."

In a second step, the "QTsome™" lipid nanoparticle formulation in 50% EtOH" is diluted at a 1:1 ratio with 20 nM citric acid buffer, pH 4.5 to form "QTsome™" lipid nanoparticle formulation in 25% EtOH."

In a third step, the "QTsome™" lipid nanoparticle formulation in 25% EtOH" is diluted at a 1:1 ratio with 300 nM NaCl, 20 nM NaOH buffer, pH 7, to form "QTsome™" lipid nanoparticle formulation in 12.5% EtOH."

In a fourth step, the "QTsome™" lipid nanoparticle formulation in 12.5% EtOH" is diluted at a 1:1 ratio with PBS, pH 7, to form "QTsome™" lipid nanoparticle formulation in 6.25% EtOH."

In a fifth step, the "QTsome™" lipid nanoparticle formulation in 6.25% EtOH" is subjected to diafiltration to concentrate "QTsome™" lipid nanoparticle formulation and remove EtOH, to form "QTsome™" lipid nanoparticle formulation in ~0% EtOH."

Figure 10B:
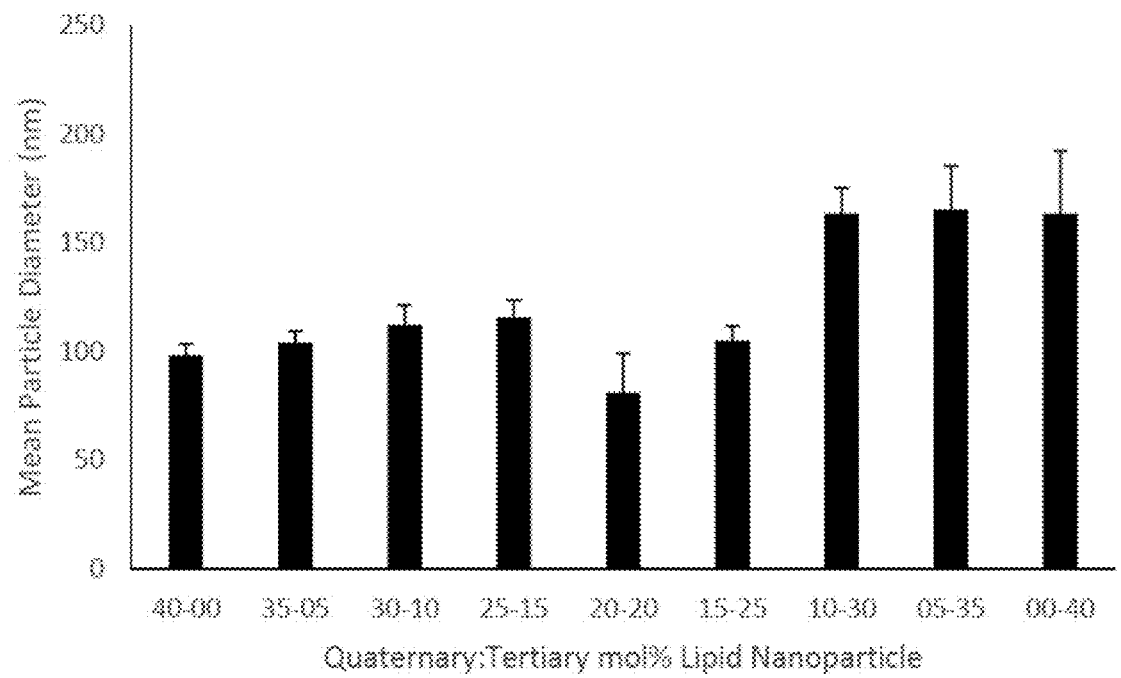
FIG. 10B is a graph showing the optimization of one embodiment of a QTsome™" lipid nanoparticle formulation.

FIG. 10B shows where the ratios of a quaternary: tertiary(% mol) were adjusted to optimize one formulation. Based upon physical characterization and prior in vitro transfection data, 15:25 was selected for the base composition of the QTsome™" lipid nanoparticle formulation.

In certain embodiments, it is desired to have small particles (<150 nm) and moderate zeta potential (+10-30 mV) to potentiate delivery of oligonucleotides. Furthermore, it is desirable that the lipid nanoparticles exhibit high stability and slow release to maximize in vivo delivery and therapeutic efficacy. Particle size measurement by DLS indicated particles of approximately 80-170 nm in diameter (FIG. 10B). Particles with greater amount of quaternary amine (15-40 mol %) achieved particles of smaller size (<120 nm).

Figure 11:
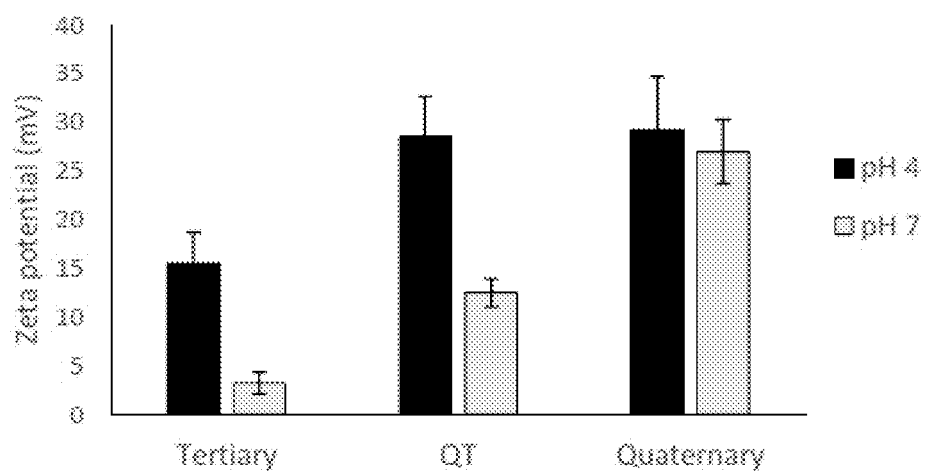
FIG. 11 is a graph showing the effect of pH on surface charge, comparing zeta potential.

FIG. 11 is a graph showing the effect of pH on surface charge, comparing particle size and zeta potential. In certain embodiments, the particle size is less than about 150 nm to facilitate EPR effect and to allow for post-production sterile filtration. Also, in certain embodiments, the zeta potential is moderate to avoid nonspecific uptake by macrophages and (reticuloendothelial system (RES) mediated clearance. In the data shown in the graph in FIG. 11, the mean particle diameter is 104.9+/−54.8 nm. With respect to the zeta potential, placing "QTsome™" lipid nanoparticle formulation under acidic pH cationizes the tertiary amine, leading to increase surface charge.

Zeta potential measurement (FIG. 11) revealed QT particles of 12.49±1.45 mV in PBS (pH 7.4) and 29.89±8.16 mV in citric acid buffer (pH 4.0), thus demonstrating the pH responsive behavior of the conditionally ionizable formulation and potential application in promoting endosomal lysis. The pH responsive behavior of QT fell between the range of charges for lipid nanoparticles containing only tertiary or quaternary amine at similar pH values. The charge on tertiary amines changed from 3 to 15 mV with increasingly acidic pH. Conversely, quaternary amine containing lipid nanoparticles did not vary much with changes in buffer solution (27 and 29 mV). This intermediate pH-responsive property may thus be desirable in certain embodiments for desired in vivo activity of QT.

Figure 12A:
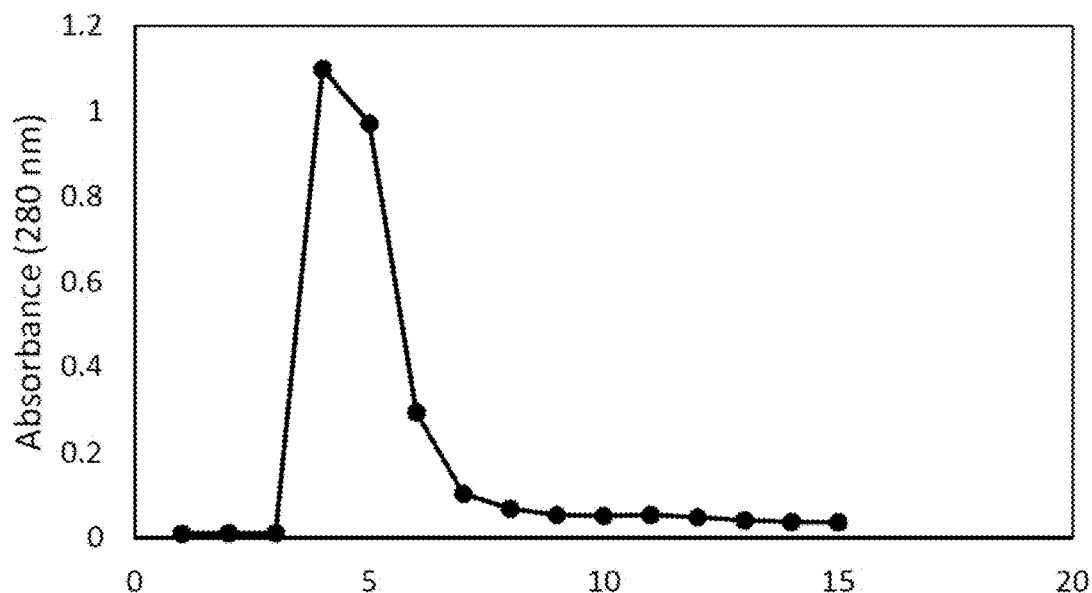
FIG. 12A is a graph showing drug loading efficiency.

FIG. 12A is a graph showing drug loading efficiency. The encapsulation efficiency $(\%) = (1 - FI_{without\ Triton\ X-100}/FI_{with\ Triton\ X-100}) \times 100\%$. The encapsulation efficiency was determined to be 83.3+/−4.17% by Oligreen Assay. The CL4B column separation of "QTsome™" lipid nanoparticle formulation further provides evidence of nearly complete anti-miR (AM) encapsulation.

Encapsulation efficiency studies demonstrated high drug loading of 83.3±4.17% by fluorescent intensity measurement. CL 4B gel-filtration chromatography analysis (FIG. 12A) showed approximately 90% encapsulation of the oligonucleotide within the encapsulated drug fractions with very little oligonucleotide remaining in the free drug fractions.

Figure 12B:
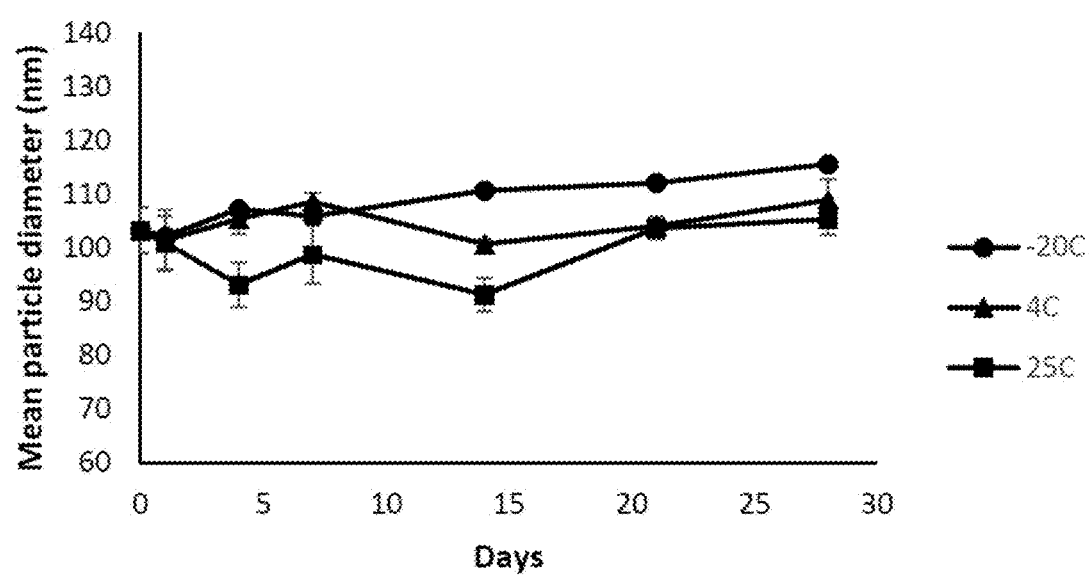
FIG. 12B is a graph showing particle storage stability, comparing mean diameter (nm) at: −20° C. (top line); 4° C. (bottom line); and, 25° C. (middle line) over time (days).

FIG. 12B is a graph showing particle storage stability, comparing mean diameter (nm) at: −20° C. (top line); 4° C. (bottom line); and, 25° C. (middle line) over time (days).

The formulation further demonstrate high stability under storage at −20 (with 10% sucrose as a cryoprotectant), 4, and 25° C. over a period of 30 days, maintaining a size of ~110 nm (FIG. 12B).

Figure 13:
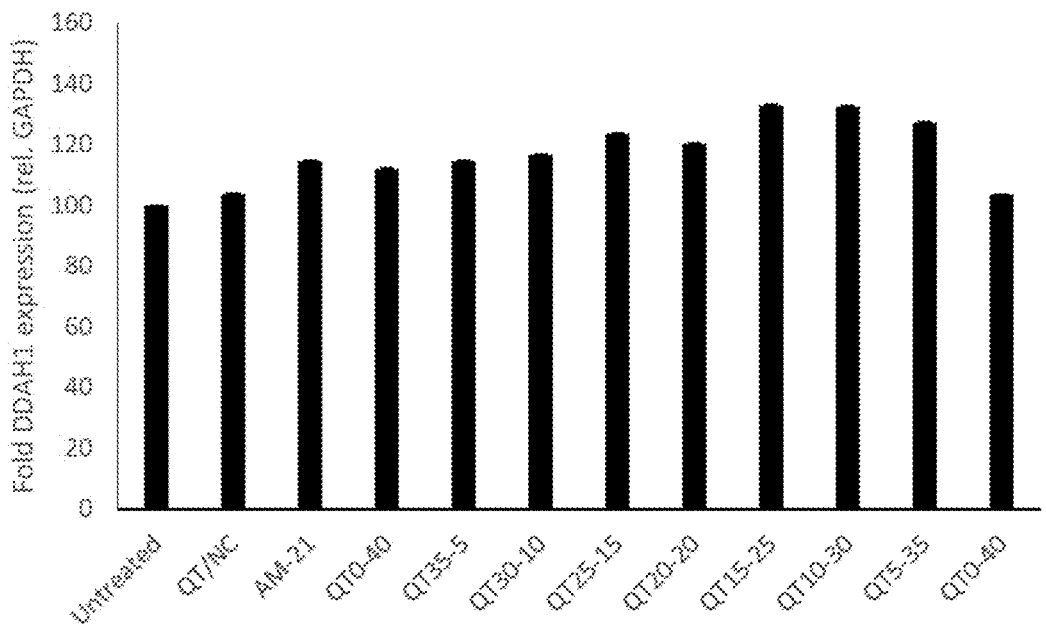
FIG. 13 is a graph showing QT of varying lipoamine composition prepared and evaluated for relative transfection efficiency, in fold increase in DDAH1 expression (rel. GADPH). Data represent the mean±SD of three separate transfections.

FIG. 13 is a graph showing one example of formula optimization where a series of QT formulations were evaluated to determine the different desirable ratios of quaternary and tertiary lipoamine for transfection. Formulations are identified as QT(mol % quaternary amine)-(mol % tertiary amine) in FIG. 13. Treatment with 50 nM AM-21 revealed QT with 15 mol % DOTAP and 25 mol % DODMA to perform best in upregulation of DDAH1 (1.33-fold). This combination of lipids was chosen for further in vitro and in vivo experiments, as described herein. Formulations QT10-30 and QT5-35 also performed well, with 1.32 and 1.27-fold upregulation respectively. Formulations containing only quaternary or tertiary lipoamine did not perform as well relative to the formulations with the various combinations.

Figure 14:
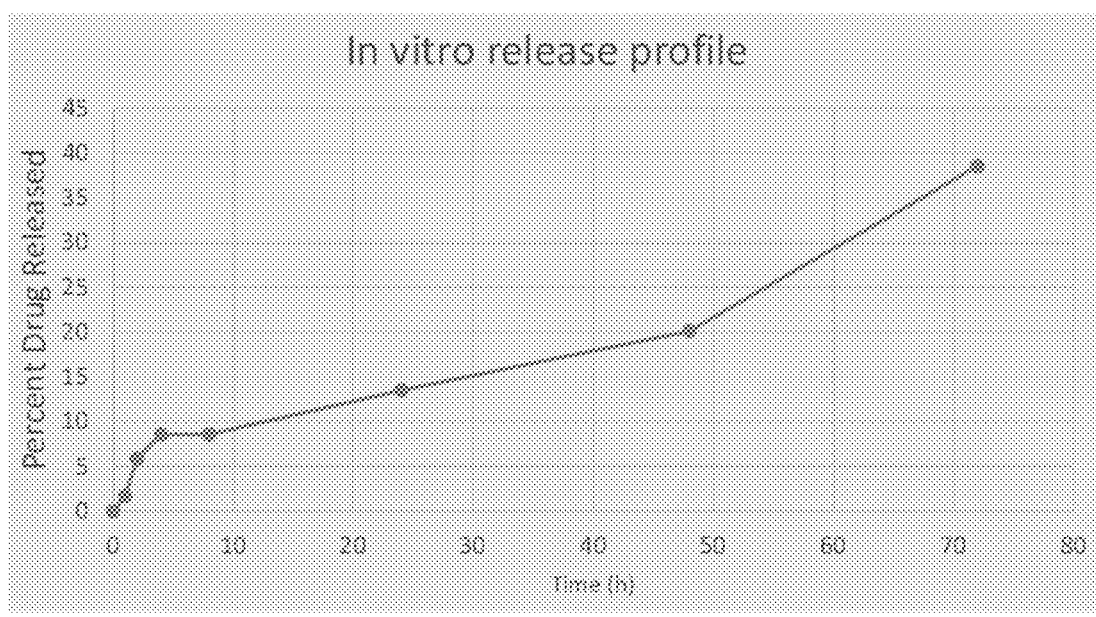
FIG. 14 is a graph showing stability, as measured by an in vitro release profile, comparing percent drug released over time (hours).

FIG. 14 is a graph showing stability, as measured by an in vitro release profile, comparing percent drug released over time (hours). The particle tend to aggregate over time when stored at −20° C., but are stable when stored at 4° C. and 25° C. In addition, dialysis against PBS demonstrates a relatively slow drug release kinetics.

Example 8

FIG. 15 provides a list of anti-miR-21 compounds 101-125 (SEQ ID NOS:4-28) which were designed and tested:

Example 8a

FIG. 16A is a graph showing activity of compounds 116, 118, 117, 112, 113, 114, 108, 109, 110, a negative control, and AM-21 (anti-21), in ANKRD46 (ANKRD46/GAPDH (fold change) at 100 nM, 25 nM, 6.25 nM, 1.56 nM).

Figure 16B:
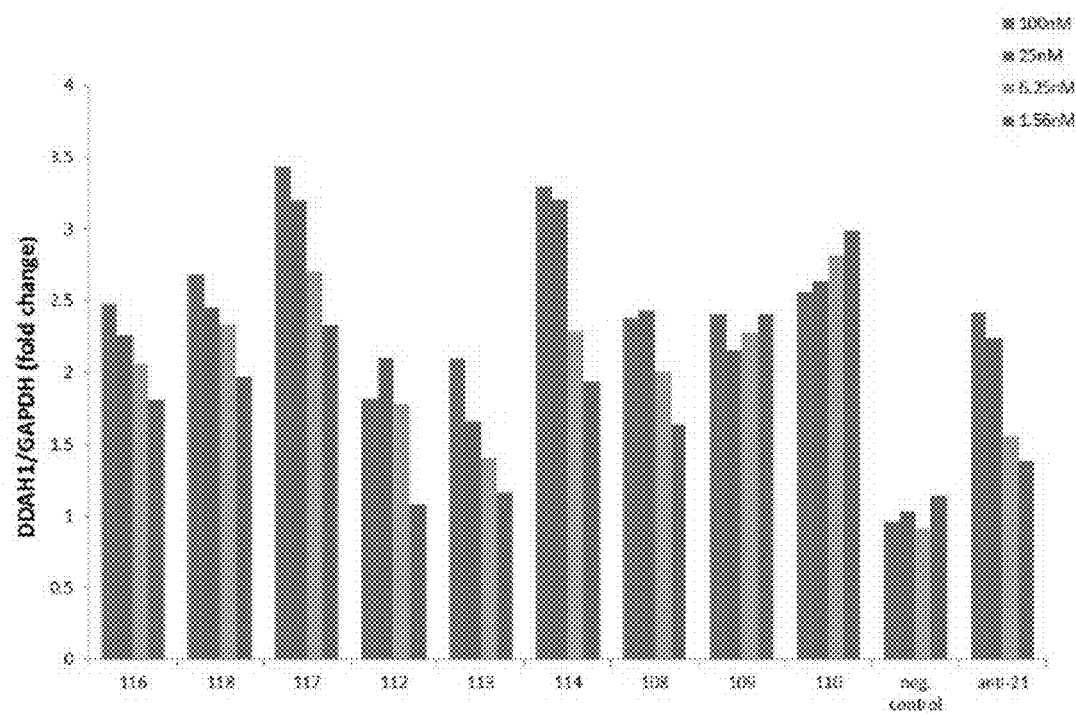
FIG. 16B is a graph showing activity of compounds 116, 118, 117, 112, 113, 114, 108, 109, 110, a negative control, and anti-miR-21 (anti-21) of SEQ ID NO:3, in DDAH1 (DDAHUGAPDH (fold change) at 100 nM, 25 nM, 6.25 nM, 1.56 nM).

FIG. 16B is a graph showing activity of compounds 116, 118, 117, 112, 113, 114, 108, 109, 110, a negative control, and AM-21 (anti-21), in DDAH1 (DDAH1/GAPDH (fold change) at 100 nM, 25 nM, 6.25 nM, 1.56 nM).

Figure 16C:
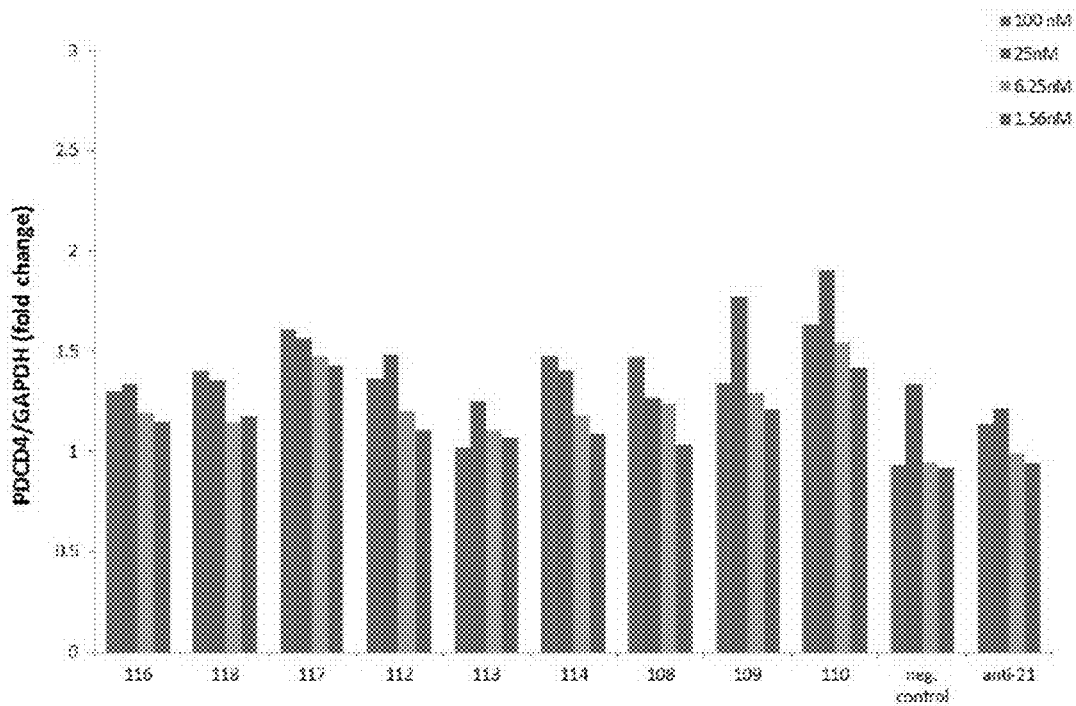
FIG. 16C is a graph showing activity of compounds 116, 118, 117, 112, 113, 114, 108, 109, 110, a negative control, and anti-miR-21 (anti-21) of SEQ ID NO:3, in PDCD4 (PDCD4/GAPDH (fold change) at 100 nM, 25 nM, 6.25 nM, 1.56 nM).

FIG. 16C is a graph showing activity of compounds 116, 118, 117, 112, 113, 114, 108, 109, 110, a negative control, and AM-21 (anti-21), in PDCD4 (PDCD4/GAPDH (fold change) at 100 nM, 25 nM, 6.25 nM, 1.56 nM).

Example 8b

Figure 17A:
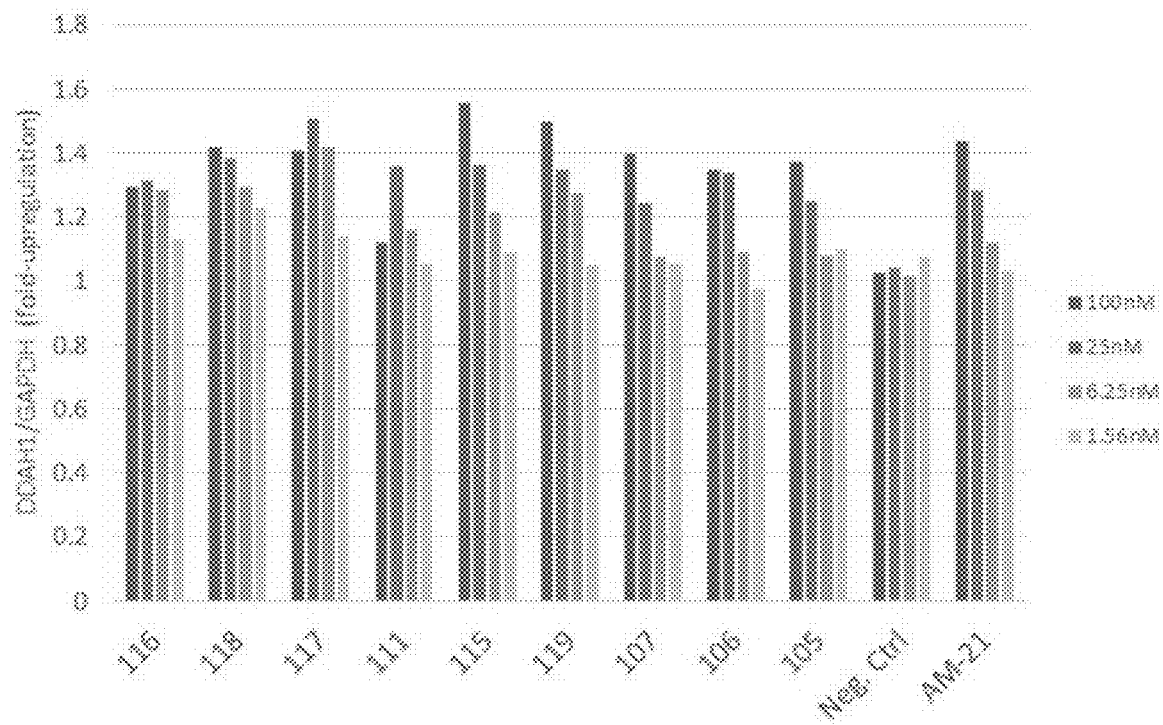
FIG. 17A is a graph showing activity of compounds 116, 118, 117, 111, 115, 119, 107, 106, 105, a negative control, and anti-miR-21 of SEQ ID NO:3 (AM-21), in DDAH1 (DDAHUGAPDH (fold change) at 100 nM, 25 nM, 6.25 nM, 1.56 nM).

FIG. 17A is a graph showing activity of compounds 116, 118, 117, 111, 115, 119, 107, 106, 105, a negative control, and anti-AM21, in DDAH1 (DDAH1/GAPDH (fold change) at 100 nM, 25 nM, 6.25 nM, 1.56 nM).

Figure 17B:
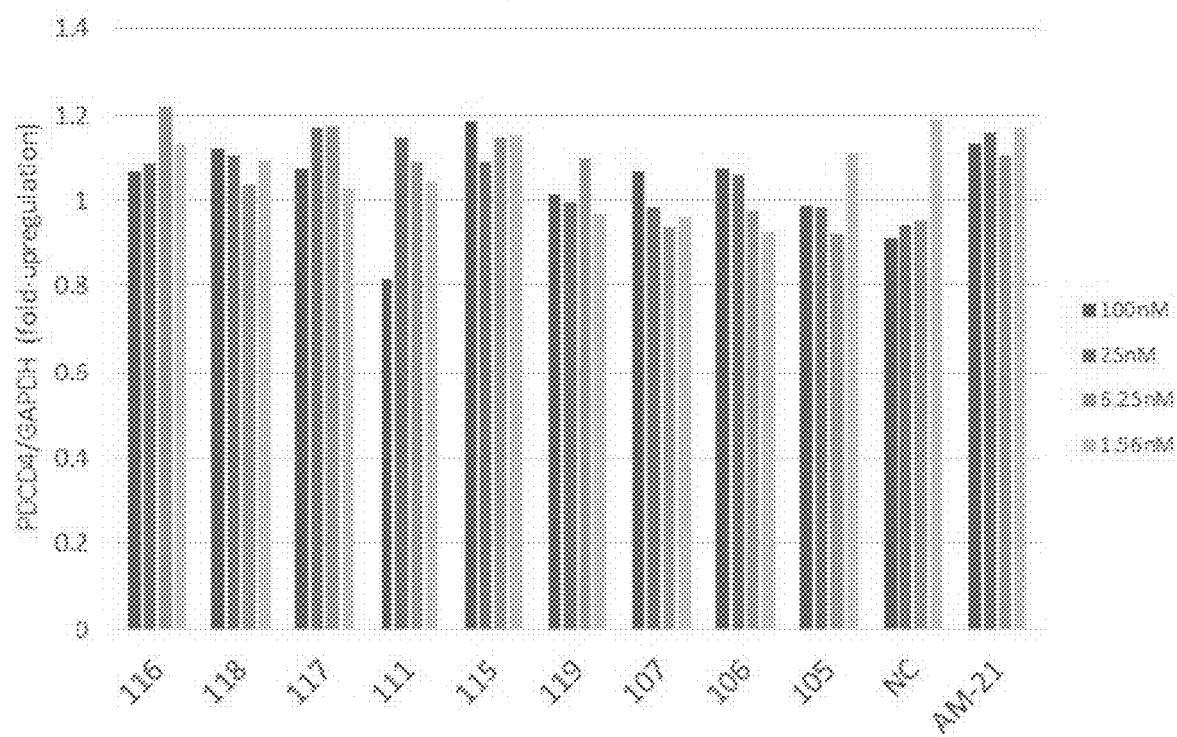
FIG. 17B is a graph showing activity of compounds 116, 118, 117, 111, 115, 119, 107, 106, 105, a negative control, and anti-miR-21 of SEQ ID NO:3 (AM-21), in PDCD4 (PDCD4/GAPDH (fold change) at 100 nM, 25 nM, 6.25 nM, 1.56 nM).

FIG. 17B is a graph showing activity of compounds 116, 118, 117, 111, 115, 119, 107, 106, 105, a negative control, and anti-AM21, in PDCD4 (PDCD4/GAPDH (fold change) at 100 nM, 25 nM, 6.25 nM, 1.56 nM).

Example 8c

Figure 18A:
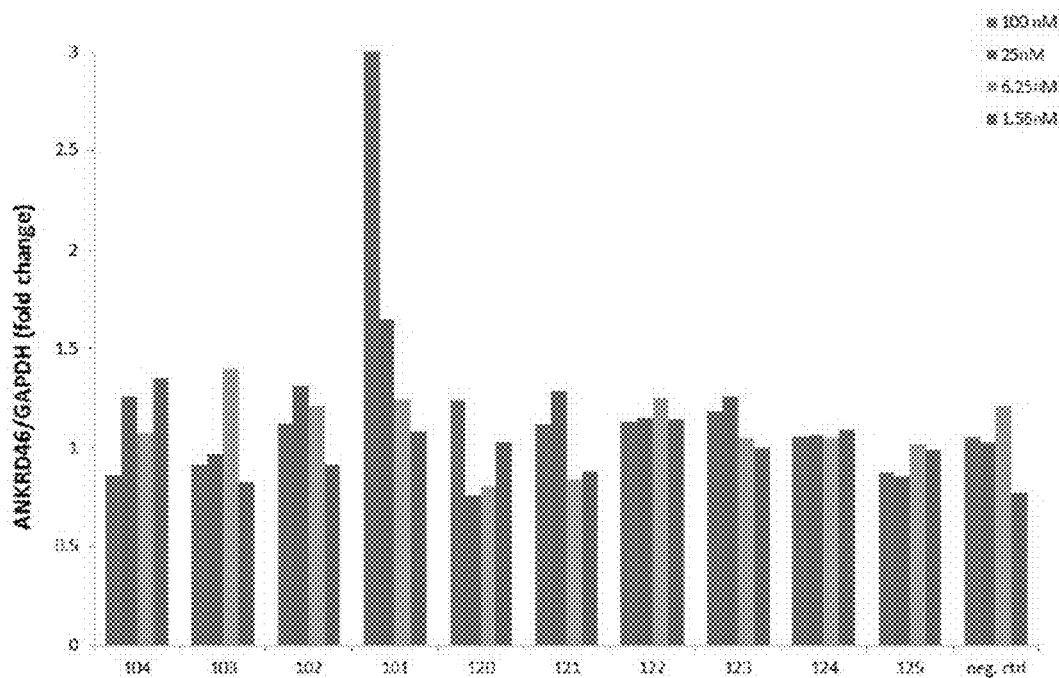
FIG. 18A is a graph showing activity of compounds 104, 103, 102, 101, 120, 121, 122, 123, 124, 125, a negative control, and anti-miR-21 of SEQ ID NO:3 (anti-21), in ANKRD46 (ANKRD46/GAPDH (fold change) at 100 nM, 25 nM, 6.25 nM, 1.56 nM).

FIG. 18A is a graph showing activity of compounds 104, 103, 102, 101, 120, 121, 122, 123, 124, 125, a negative control, and AM-21 (anti-21), in ANKRD46 (ANKRD46/GAPDH (fold change) at 100 nM, 25 nM, 6.25 nM, 1.56 nM).

Figure 18B:
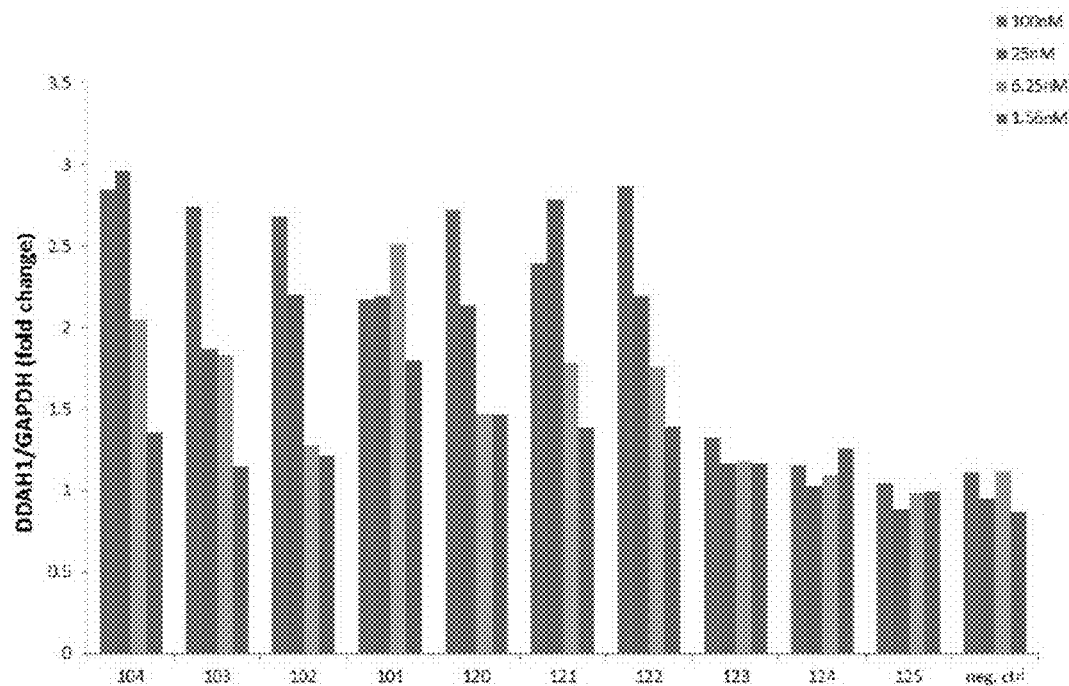
FIG. 18B is a graph showing activity of compounds 104, 103, 102, 101, 120, 121, 122, 123, 124, 125, a negative control, and anti-miR-21 of SEQ ID NO:3 (anti-21), in DDAH1 (DDAN1/GAPDH (fold change) at 100 nM, 25 nM, 6.25 nM, 1.56 nM).

FIG. 18B is a graph showing activity of compounds 104, 103, 102, 101, 120, 121, 122, 123, 124, 125, a negative control, and AM-21 (anti-21), in DDAH1 (DDAN1/GAPDH (fold change) at 100 nM, 25 nM, 6.25 nM, 1.56 nM).

Figure 18C:
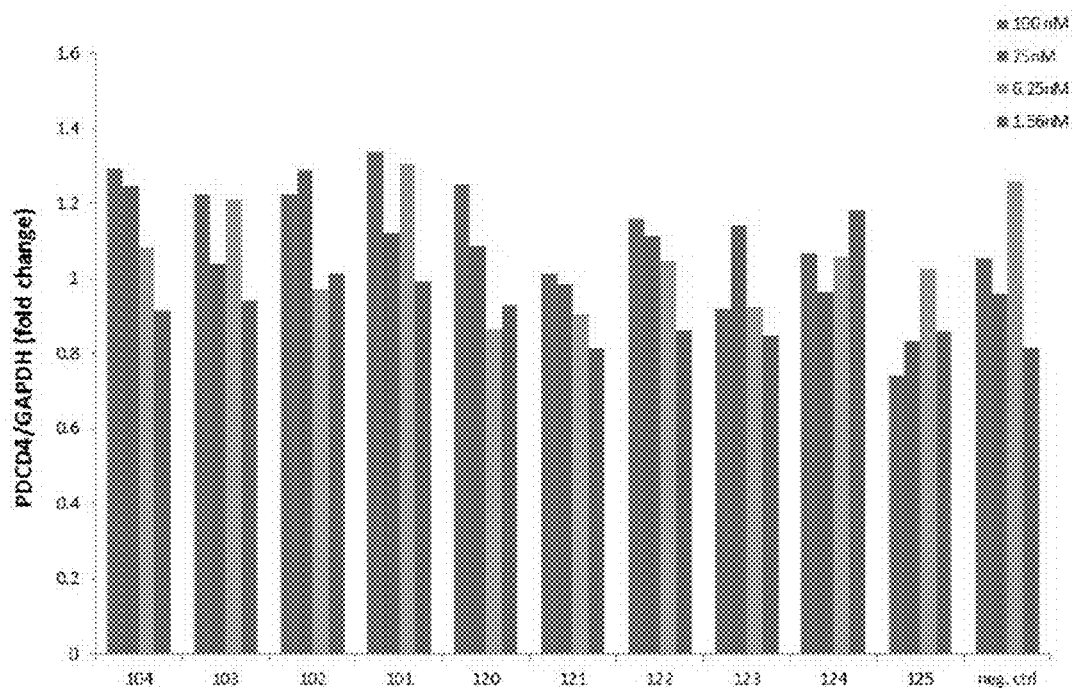
FIG. 18C is a graph showing activity of compounds 104, 103, 102, 101, 120, 121, 122, 123, 124, 125, a negative control, and anti-miR-21 of SEQ ID NO:3 (anti-21), in PDCD4 (PDCD4/GAPDH (fold change) at 100 nM, 25 nM, 6.25 nM, 1.56 nM).

FIG. 18C is a graph showing activity of compounds 104, 103, 102, 101, 120, 121, 122, 123, 124, 125, a negative control, and AM-21 (anti-21), in PDCD4 (PDCD4/GAPDH (fold change) at 100 nM, 25 nM, 6.25 nM, 1.56 nM).

Example 8d

Figure 19A:
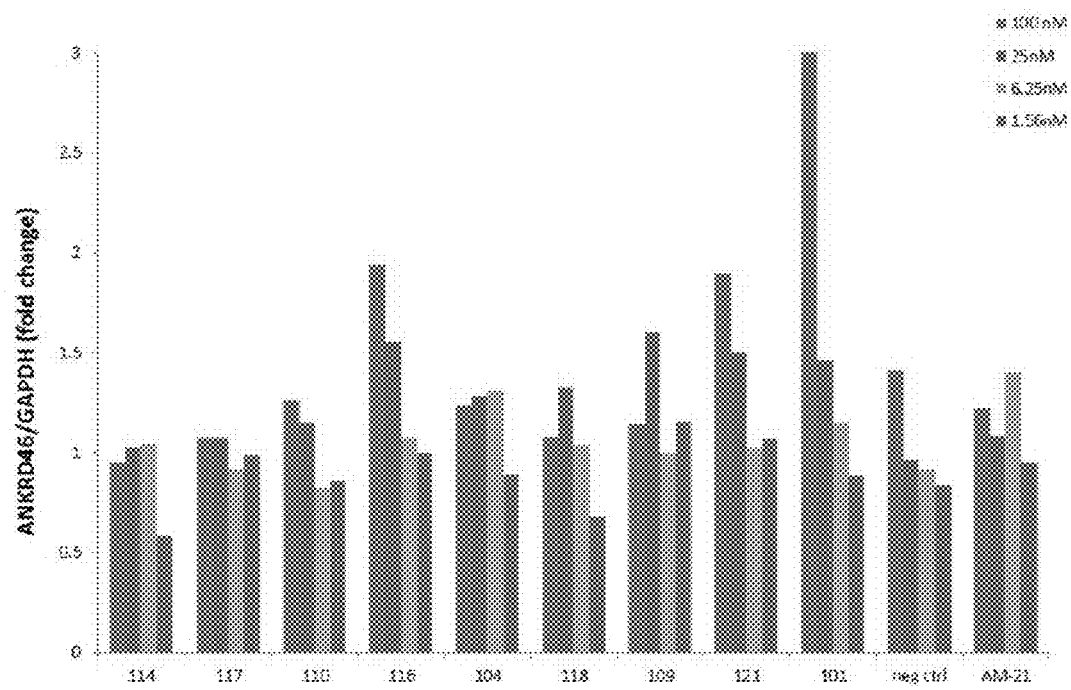
FIG. 19A is a graph showing activity of compounds 114, 117, 110, 116, 118, 109, 121, 101, a negative control, and anti-miR-21 of SEQ ID NO: 3 (AM-21), in ANKRD46 (ANKRD46/GAPDH (fold change) at 100 nM, 25 nM, 6.25 nM, 1.56 nM).

FIG. 19A is a graph showing activity of compounds 114, 117, 110, 116, 118, 109, 121, 101, a negative control, and AM-21, in ANKRD46 (ANKRD46/GAPDH (fold change) at 100 nM, 25 nM, 6.25 nM, 1.56 nM).

Figure 19B:
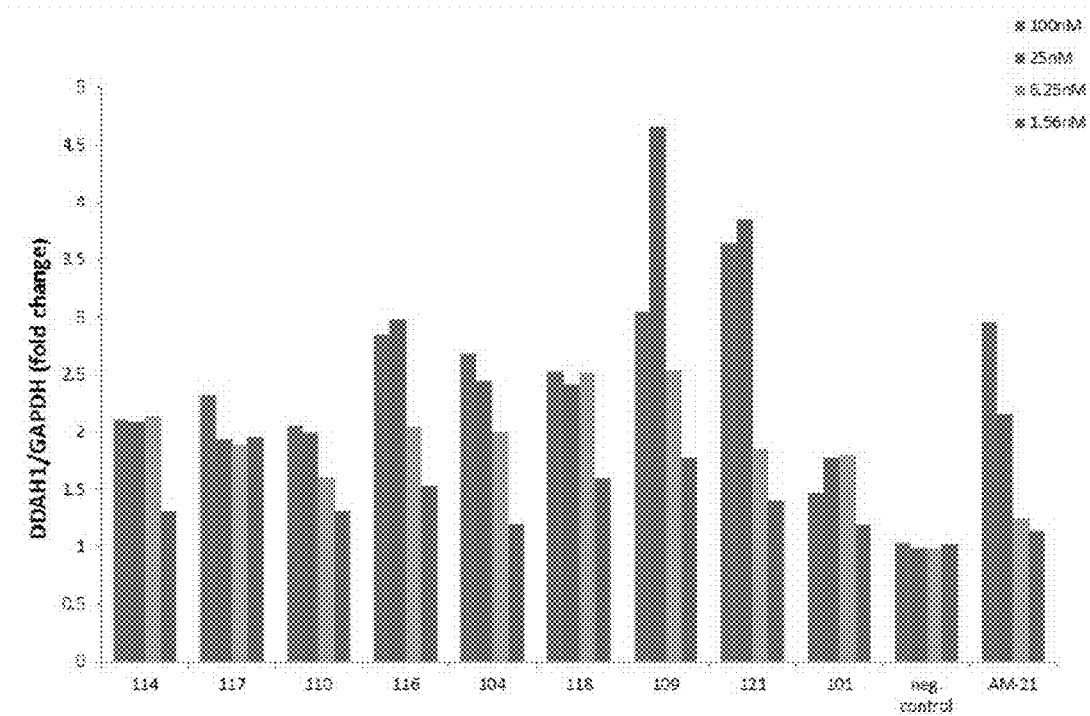
FIG. 19B is a graph showing activity of compounds 114, 117, 110, 116, 118, 109, 121, 101, a negative control, and AM-21, in DDAH1 (DDAHUGAPDH (fold change) at 100 nM, 25 nM, 6.25 nM, 1.56 nM).

FIG. 19B is a graph showing activity of compounds 114, 117, 110, 116, 118, 109, 121, 101, a negative control, and AM-21, in DDAH1 (DDAH1/GAPDH (fold change) at 100 nM, 25 nM, 6.25 nM, 1.56 nM).

Figure 19C:
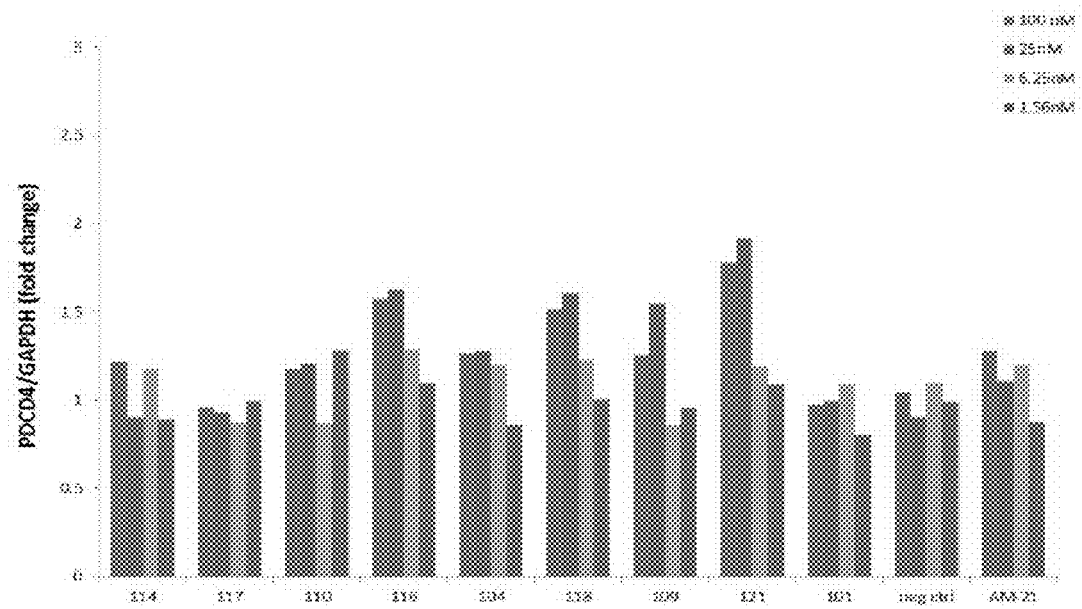
FIG. 19C is a graph showing activity of compounds 114, 117, 110, 116, 118, 109, 121, 101, a negative control, and AM-21, in PDCD4 (PDCD4/GAPDH (fold change) at 100 nM, 25 nM, 6.25 nM, 1.56 nM).

FIG. 19C is a graph showing activity of compounds 114, 117, 110, 116, 118, 109, 121, 101, a negative control, and AM-21, in PDCD4 (PDCD4/GAPDH (fold change) at 100 nM, 25 nM, 6.25 nM, 1.56 nM).

Example 8e

Figure 20A:
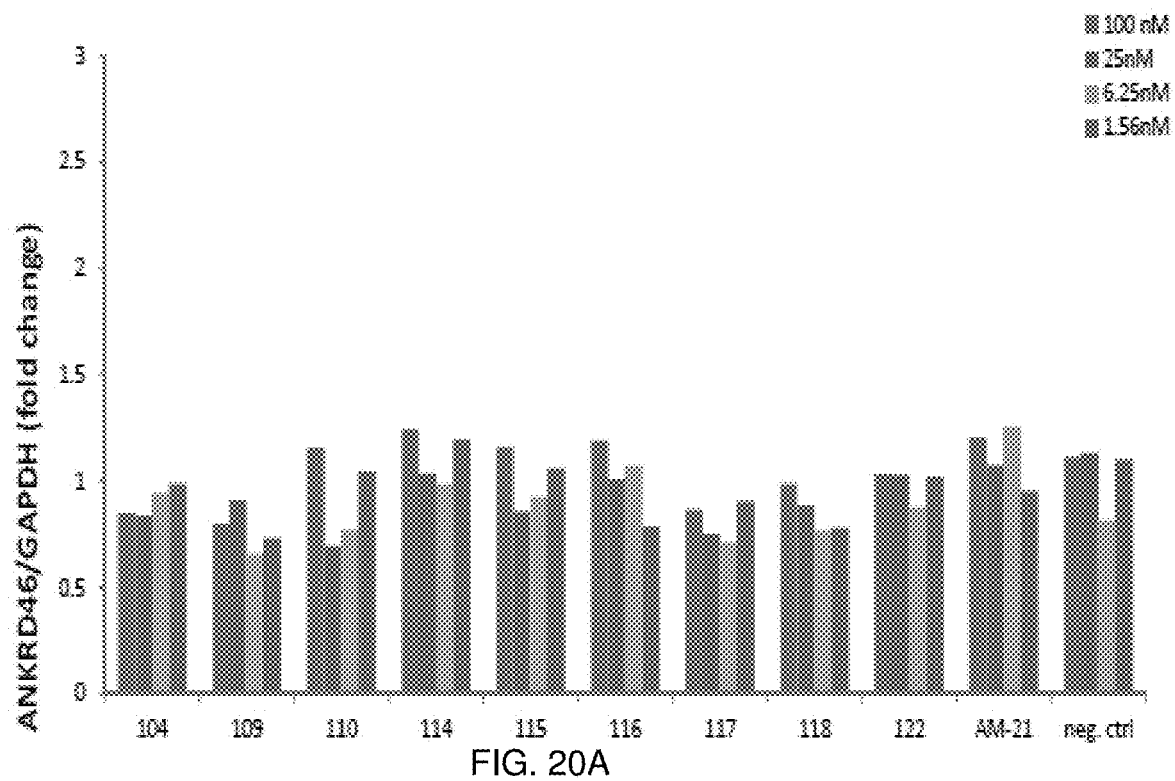
FIG. 20A is a graph showing activity of compounds 104, 109, 110, 114, 115, 116, 117, 118, 122, AM-21 and a negative control, in ANKRD46 (ANKRD46/GAPDH (fold change) at 100 nM, 25 nM, 6.25 nM, 1.56 nM).

FIG. 20A is a graph showing activity of compounds 104, 109, 110, 114, 115, 116, 117, 118, 122, AM-21 and a negative control, in ANKRD46 (ANKRD46/GAPDH (fold change) at 100 nM, 25 nM, 6.25 nM, 1.56 nM).

Figure 20B:
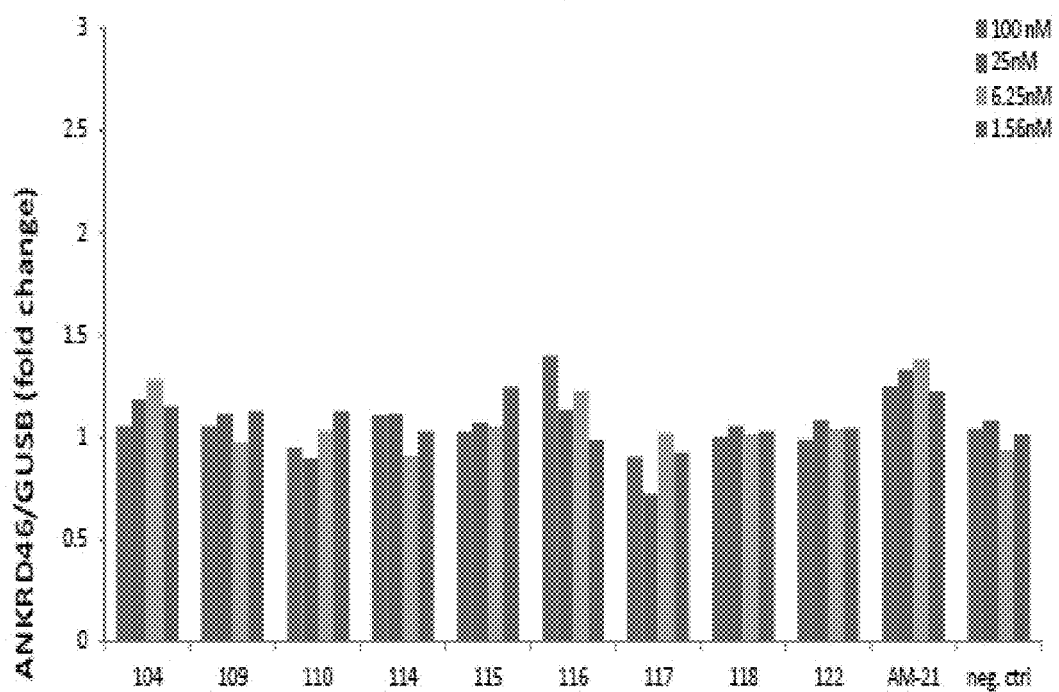
FIG. 20B is a graph showing activity of compounds 104, 109, 110, 114, 115, 116, 117, 118, 122, AM-21 and a negative control, in ANKRD46 (ANKRD46/GUSB (fold change) at 100 nM, 25 nM, 6.25 nM, 1.56 nM).

FIG. 20B is a graph showing activity of compounds 104, 109, 110, 114, 115, 116, 117, 118, 122, AM-21 and a negative control, in ANKRD46 (ANKRD46/GUSB (fold change) at 100 nM, 25 nM, 6.25 nM, 1.56 nM).

Example 8f

Figure 21A:
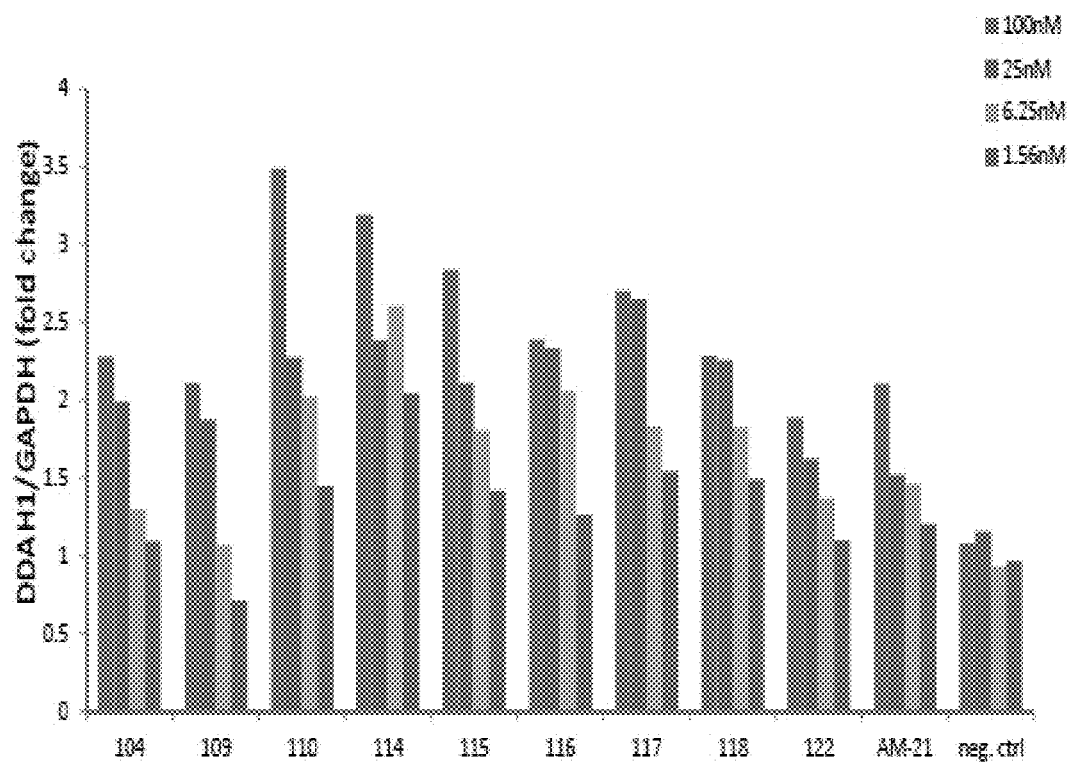
FIG. 21A is a graph showing activity of compounds 104, 109, 110, 114, 115, 116, 117, 118, 122, AM-21 and a negative control, in DDAH1 (DDAH1/GAPDH (fold change) at 100 nM, 25 nM, 6.25 nM, 1.56 nM).

FIG. 21A is a graph showing activity of compounds 104, 109, 110, 114, 115, 116, 117, 118, 122, AM-21 and a negative control, in DDAH1 (DDAH1/GAPDH (fold change) at 100 nM, 25 nM, 6.25 nM, 1.56 nM).

Figure 21B:
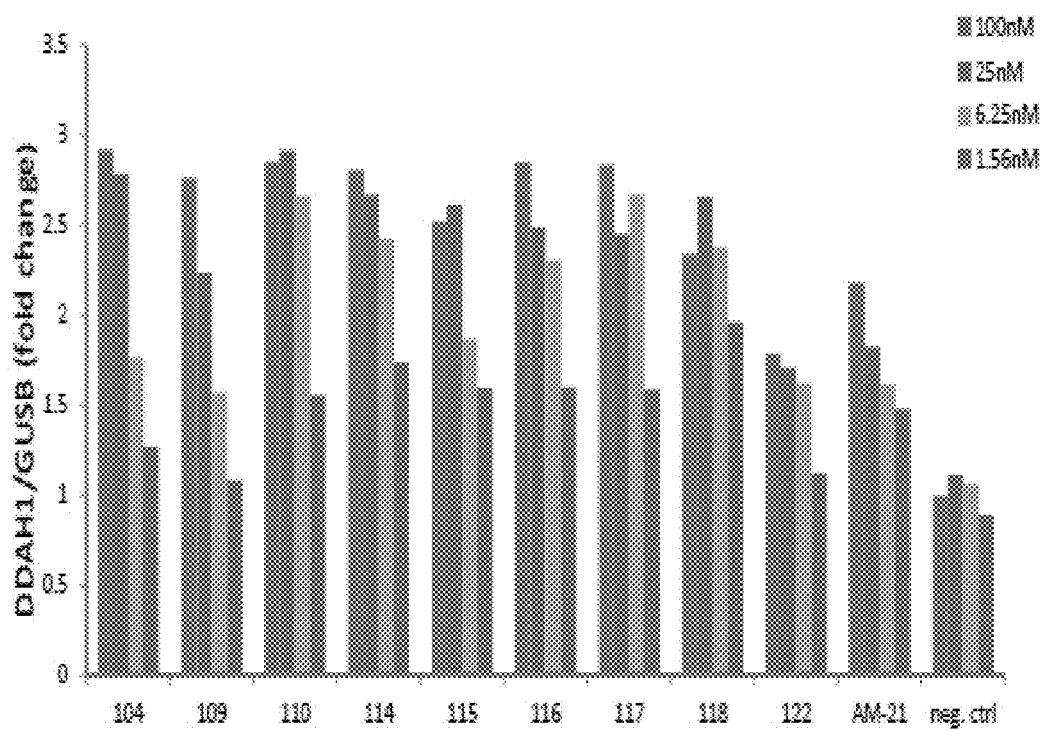
FIG. 21B is a graph showing activity of compounds 104, 109, 110, 114, 115, 116, 117, 118, 122, AM-21 and a negative control, in DDAH1 (DDAH1/GUSB (fold change) at 100 nM, 25 nM, 6.25 nM, 1.56 nM).

FIG. 21B is a graph showing activity of compounds 104, 109, 110, 114, 115, 116, 117, 118, 122, AM-21 and a negative control, in DDAH1 (DDAHUGUSB (fold change) at 100 nM, 25 nM, 6.25 nM, 1.56 nM).

Example 8g

Figure 22A:
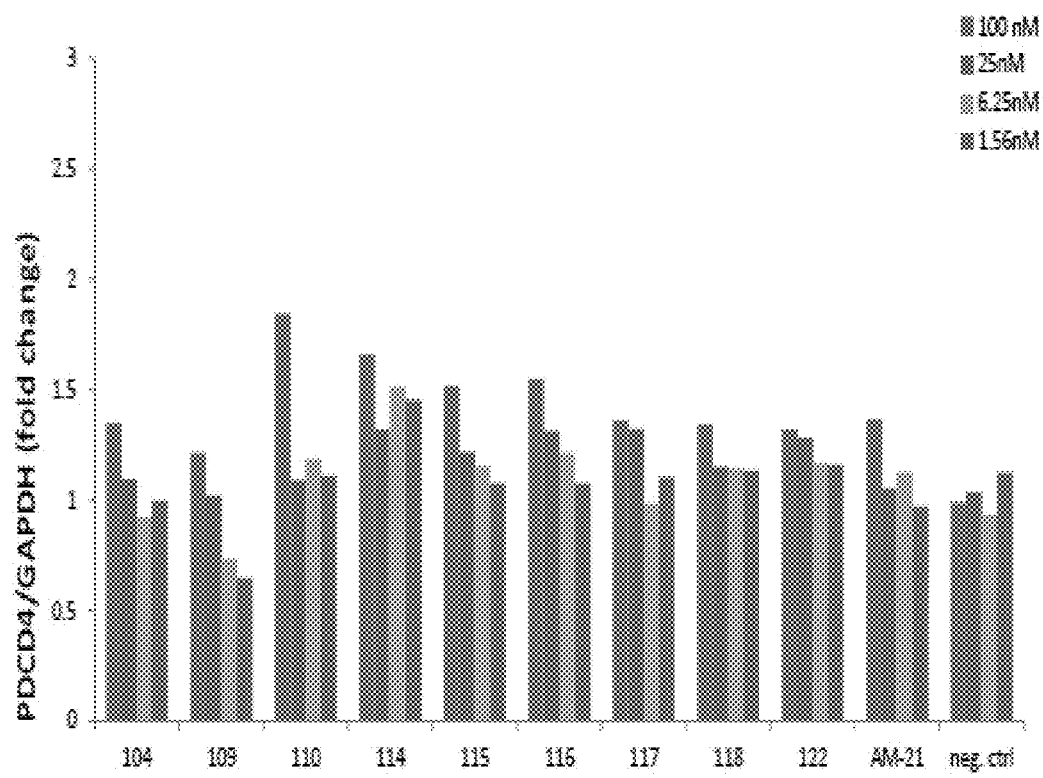
FIG. 22A is a graph showing activity of compounds 104, 109, 110, 114, 115, 116, 117, 118, 122, AM-21 and a negative control, in PDCD4 (PDCD4/GAPDH (fold change) at 100 nM, 25 nM, 6.25 nM, 1.56 nM).

FIG. 22A is a graph showing activity of compounds 104, 109, 110, 114, 115, 116, 117, 118, 122, AM-21 and a negative control, in PDCD4 (PDCD4/GAPDH (fold change) at 100 nM, 25 nM, 6.25 nM, 1.56 nM).

Figure 22B:
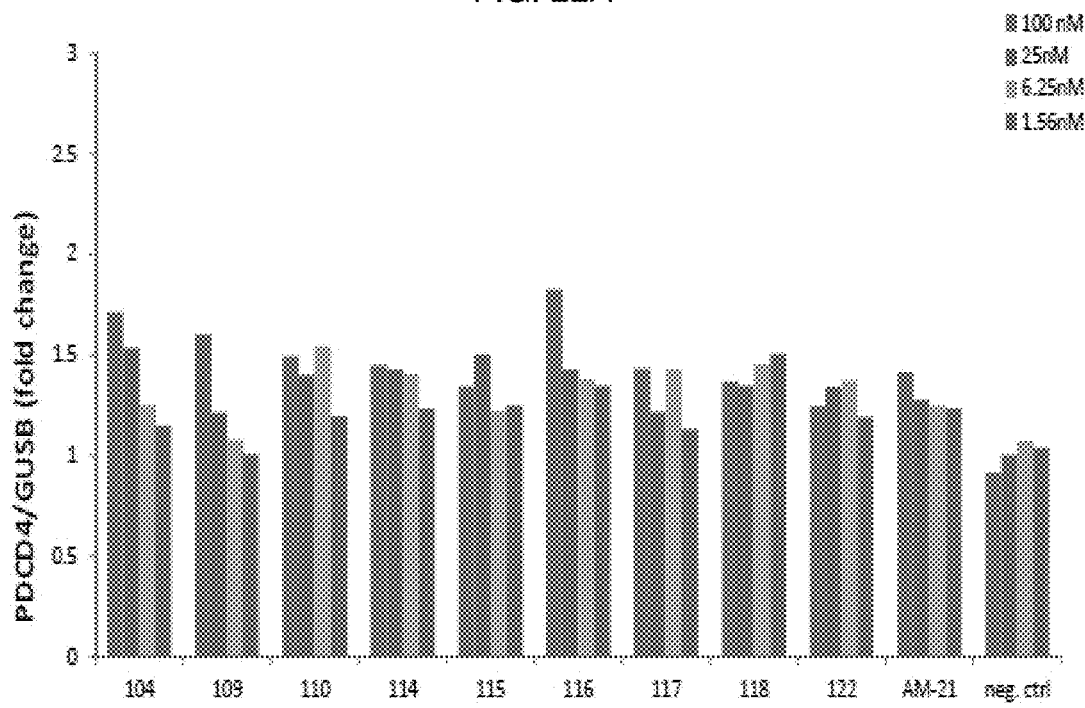
FIG. 22B is a graph showing activity of compounds 104, 109, 110, 114, 115, 116, 117, 118, 122, AM-21 and a negative control, in PDCD4 (PDCD4/GUSB (fold change) at 100 nM, 25 nM, 6.25 nM, 1.56 nM).

FIG. 22B is a graph showing activity of compounds 104, 109, 110, 114, 115, 116, 117, 118, 122, AM-21 and a negative control, in PDCD4 (PDCD4/GUSB (fold change) at 100 nM, 25 nM, 6.25 nM, 1.56 nM).

Example 8h

Figure 23A:
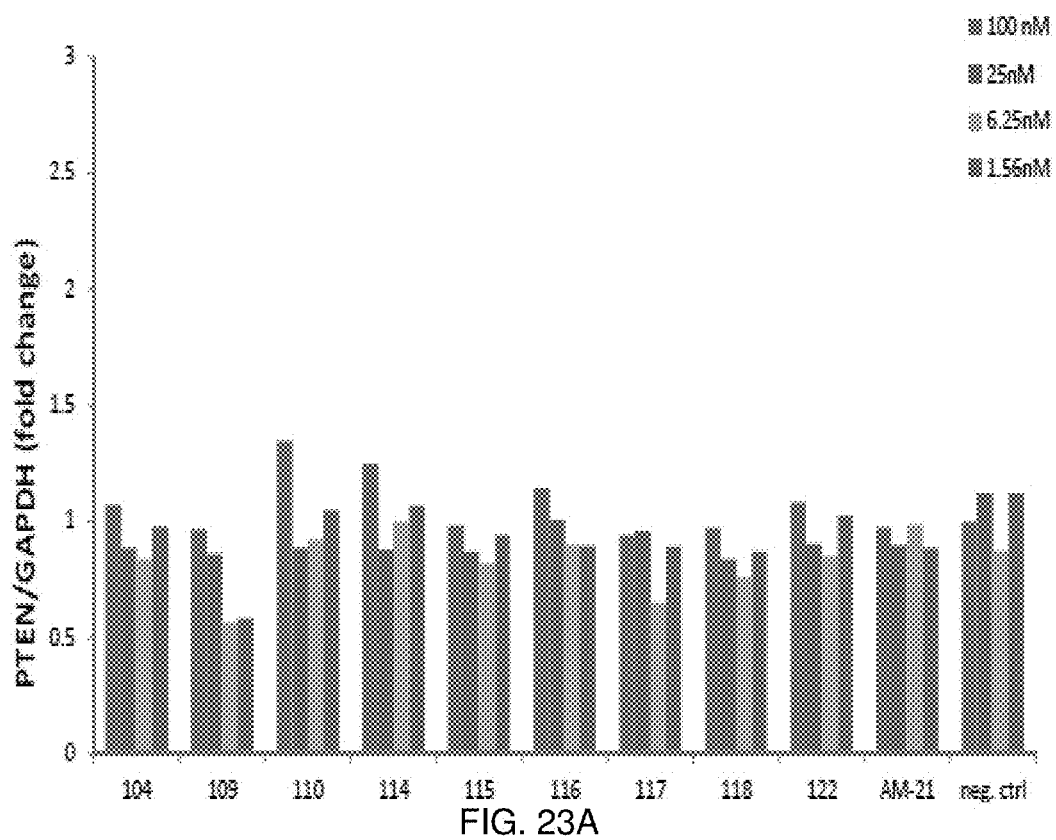
FIG. 23A is a graph showing activity of compounds 104, 109, 110, 114, 115, 116, 117, 118, 122, AM-21 and a negative control, in PTEN (PTEN/GAPDH (fold change) at 100 nM, 25 nM, 6.25 nM, 1.56 nM).

FIG. 23A is a graph showing activity of compounds 104, 109, 110, 114, 115, 116, 117, 118, 122, AM-21 and a negative control, in PTEN (PTEN/GAPDH (fold change) at 100 nM, 25 nM, 6.25 nM, 1.56 nM).

Figure 23B:
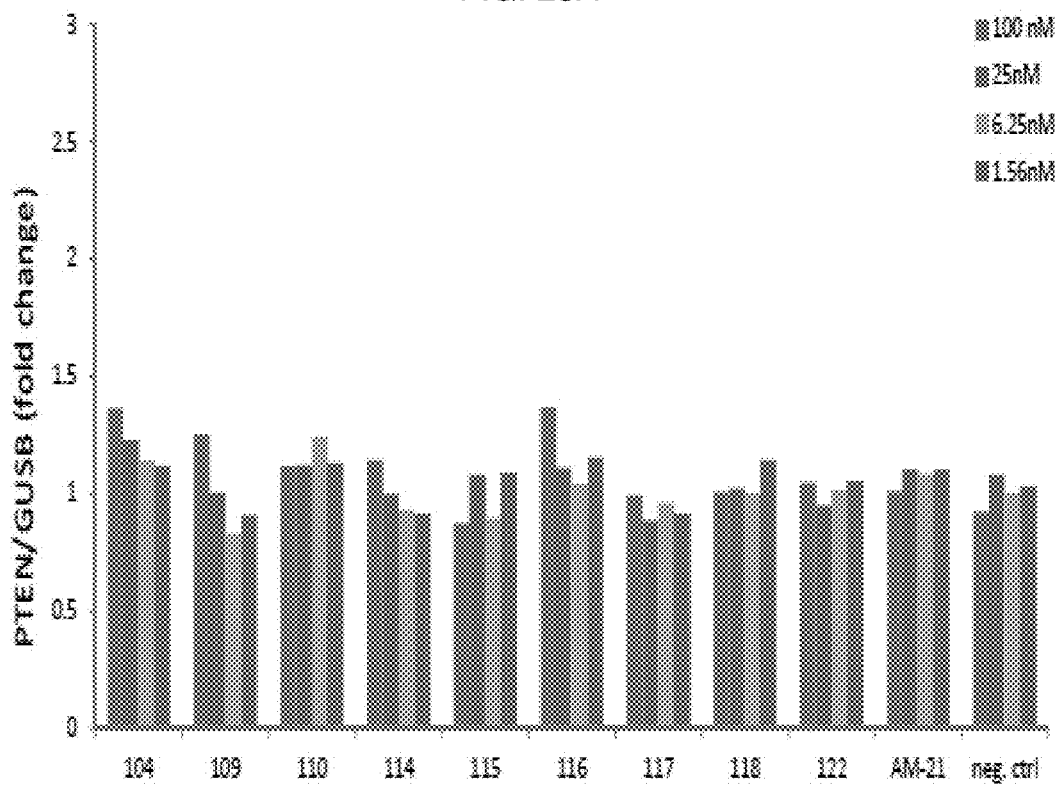
FIG. 23B is a graph showing activity of compounds 104, 109, 110, 114, 115, 116, 117, 118, 122, AM-21 and a negative control, in PTEN (PTEN/GUSB (fold change) at 100 nM, 25 nM, 6.25 nM, 1.56 nM).

FIG. 23B is a graph showing activity of compounds 104, 109, 110, 114, 115, 116, 117, 118, 122, AM-21 and a negative control, in PTEN (PTEN/GUSB (fold change) at 100 nM, 25 nM, 6.25 nM, 1.56 nM).

Example 8i

Figure 24A:
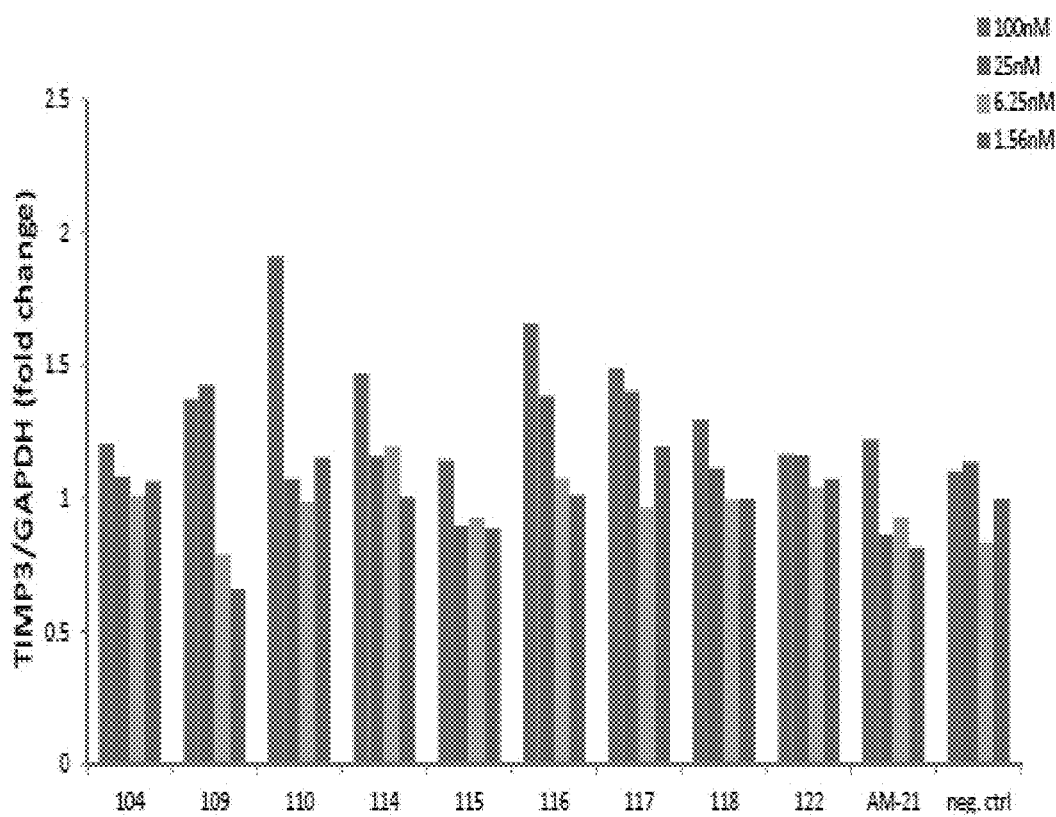
FIG. 24A is a graph showing activity of compounds 104, 109, 110, 114, 115, 116, 117, 118, 122, AM-21 and a negative control, in TIMP3 (TIMP3/GAPDH (fold change) at 100 nM, 25 nM, 6.25 nM, 1.56 nM).

FIG. 24A is a graph showing activity of compounds 104, 109, 110, 114, 115, 116, 117, 118, 122, AM-21 and a negative control, in TIMP3 (TIMP3/GAPDH (fold change) at 100 nM, 25 nM, 6.25 nM, 1.56 nM).

Figure 24B:
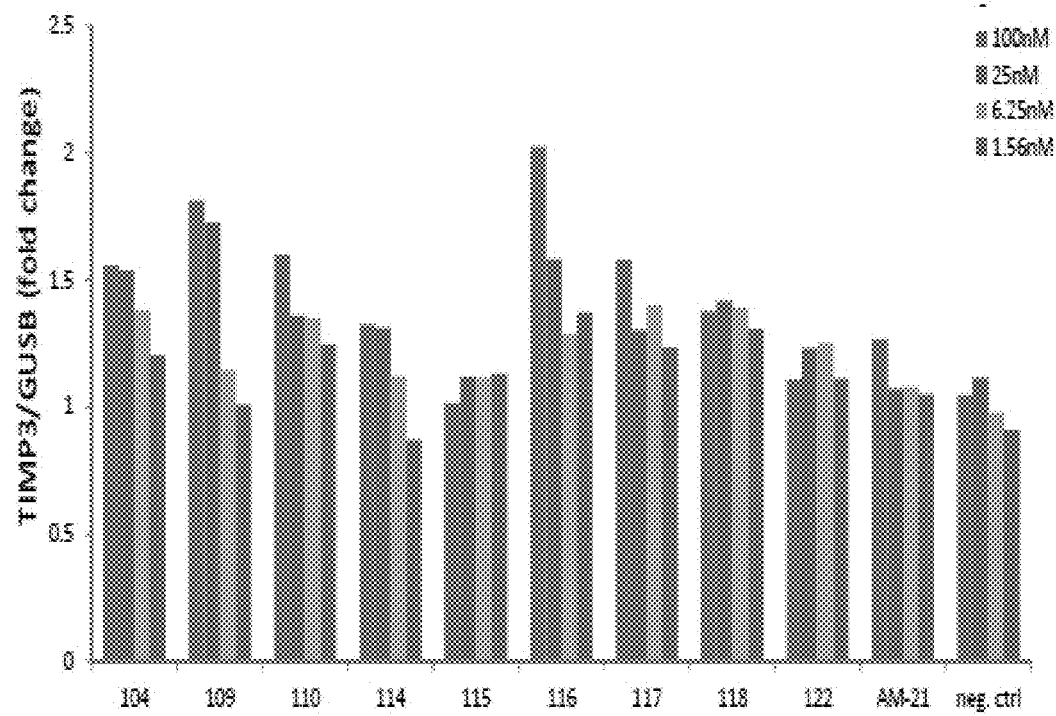
FIG. 24B is a graph showing activity of compounds 104, 109, 110, 114, 115, 116, 117, 118, 122, AM-21 and a negative control, in TIMP3 (TIMP3/GUSB (fold change) at 100 nM, 25 nM, 6.25 nM, 1.56 nM).

FIG. 24B is a graph showing activity of compounds 104, 109, 110, 114, 115, 116, 117, 118, 122, AM-21 and a negative control, in TIMP3 (TIMP3/GUSB (fold change) at 100 nM, 25 nM, 6.25 nM, 1.56 nM).

Example 8i

Figure 25A:
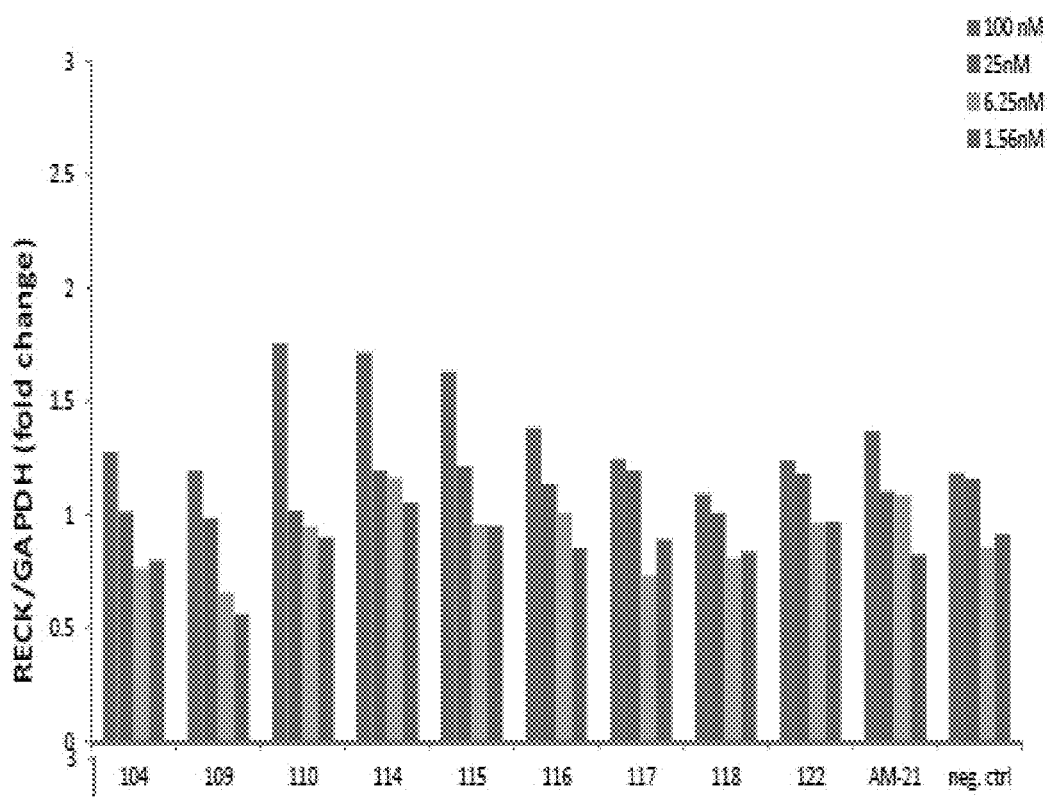
FIG. 25A is a graph showing activity of compounds 104, 109, 110, 114, 115, 116, 117, 118, 122, AM-21 and a negative control, in RECK (RECK/GAPDH (fold change) at 100 nM, 25 nM, 6.25 nM, 1.56 nM).

FIG. 25A is a graph showing activity of compounds 104, 109, 110, 114, 115, 116, 117, 118, 122, AM-21 and a negative control, in RECK (RECK/GAPDH (fold change) at 100 nM, 25 nM, 6.25 nM, 1.56 nM).

Figure 25B:
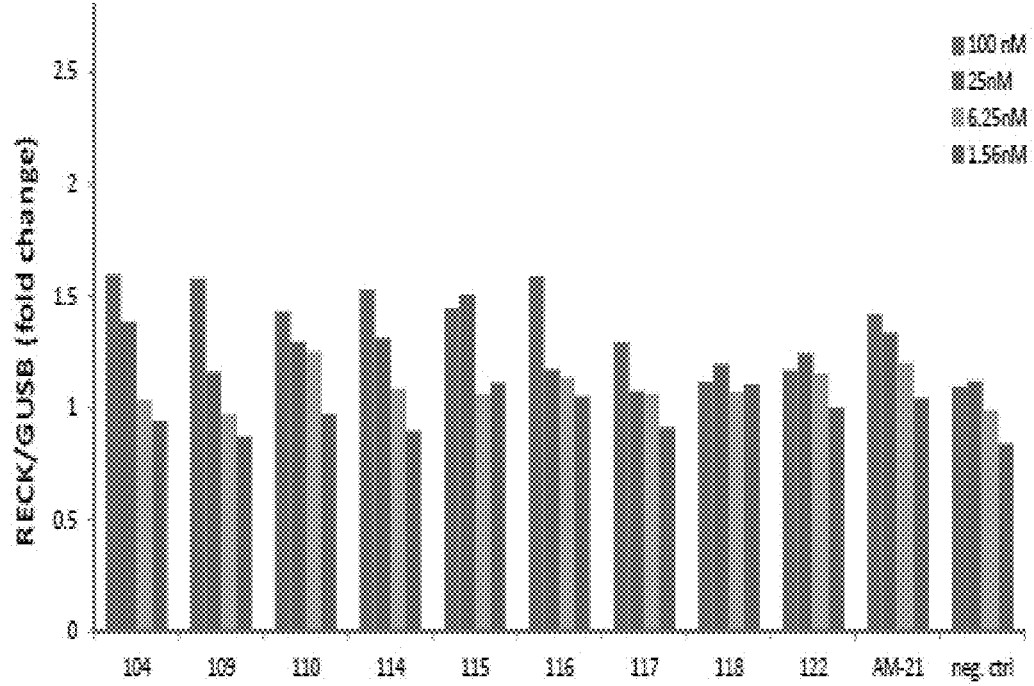
FIG. 25B is a graph showing activity of compounds 104, 109, 110, 114, 115, 116, 117, 118, 122, AM-21 and a negative control, in RECK (RECK/GUSB (fold change) at 100 nM, 25 nM, 6.25 nM, 1.56 nM).

FIG. 25B is a graph showing activity of compounds 104, 109, 110, 114, 115, 116, 117, 118, 122, AM-21 and a negative control, in RECK (RECK/GUSB (fold change) at 100 nM, 25 nM, 6.25 nM, 1.56 nM).

These examples show how a pH-sensitive carrier, QT is especially useful for the delivery of therapeutic oligonucleotides. Tertiary lipoamines form the pH-sensitive component of QT and upon exposure to acidic conditions as in the endosome, the tertiary lipoamine becomes cationized, enabling interaction with negatively charged lipids forming the endosomal bilayer and consequently leading to efficient endosomal escape of the oligonucleotides. Release of drug from the endosomal compartment is a critical step in determining drug efficacy. The inclusion quaternary amine is used to electrostatically stabilize the charge of the lipid nanoparticles under physiological pH conditions. The presence of a significant amount of quaternary amine maintains interactions with the negative charge of the oligonucleotides, thereby resulting in particles of smaller average particle size relative to particles containing mostly tertiary amine content.

In terms of surface charge, one embodiment (QT15-25) displayed an intermediary response to changing buffer condition relative to other embodiments (QT40-0 or QT0-40). The lipid nanoparticles furthermore demonstrated excellent colloidal stability and efficient drug loading, thus demonstrating practicality for clinical use and commercialization. Also, in certain embodiments, the QT may be further stabilized by the addition of cryoprotectant and processing by lyophilization to retain the drug form's integrity over long term storage.

QT/AM-21 was able to strongly downregulate miR-21 and upregulate several key targets of miR-21 including tumor suppressors, matrix metalloprotease inhibitors, and migration inhibitors. PTX kills cancer cells by stabilization of microtubules, which prevents mitosis. It is to be noted that patients normally respond to PTX with a 40-80% response rate, but many of these patients develop resistance to PTX over time. The combination of QT/AM-21 and PTX demonstrated herein shows greater reductions in cell proliferation over use of the combination of free AM-21 and PTX, thus showing greater uptake and/or efficacy of AM-21 when delivered via QT.

As another example, in an ovarian cancer model, the resistance against PTX is believed to be regulated by miR-21's effect on hypoxia-inducible factor-1α (HIF-1α) and P-glycoprotein (P-gp). HIF-1α and HIF-1β are subunits of the heterodimeric transcription factor HIF-1. HIF-1α is upregulated in response to oncogene activity, hypoxia, and growth factors. HIF-1β is comparatively benign and constitutively expressed in the body. P-gp is a member of the ATP-binding cassette (ABC) transporter family, which has been found to play a role in the development of multidrug resistance in cancer. As demonstrated herein, decreased migratory and invasion potential was observed in a dose dependent manner in response to QT/AM-21 treatment. Also, it is to be noted that, as another example, lung cancer is often diagnosed in late in its development, when metastasis has already begun. Therefore, the QT/AM-21 lipid nanoparticles described herein address a critical need that is currently unmet by chemotherapy administered in the late stage.

Further, treatment with QT/AM-21 in a xenograft mouse model was able to significantly suppress tumor growth at 1 mg/kg. Targets of miR-21 were also found to be upregulated, supporting trends observed in vitro. It is to be noted that relative increase in body weight indicated mice with better health condition. As demonstrated herein, liver and spleen weight did not differ much between the two groups, showing that the formulation was not toxic to those organs. This is an important advantage since liver and spleen are heavily fenestrated organs involved in the reticuloendothelial system with large local populations of macrophages, and lipid nanoparticles may accumulate in these organs as a result. The combination of PTX and QT/AM-21 demonstrated greater therapeutic activity than either agent administered alone. Interestingly, while PTX displayed greater therapeutic activity in vitro than QT/AM-21, the trend in tumor suppression was opposite and QT/AM-21 was slightly more effective than PTX. While not wishing to be bound by theory, it is now believed that the relative increase in QT/AM-21 activity is attributed to increased retention of the lipid nanoparticles in the tumor vasculature following injection, leading to a greater duration of therapeutic effect.

The lipid nanoparticle formulations described herein provide a broad spectrum of useful application for drug loading and treating other diseases. As a large majority of oligonucleotides are roughly 20-25 nucleotides in length and encapsulation is sequence independent, dependent instead on the relative anionic charge of the sequence, it i to be understood that the QTsome ™ lipid nanoparticle formulations described herein are not limited to administration for AM-21. Rather, the QTsome ™ lipid nanoparticle formulations are also useful to deliver virtually any type of AM, siRNA, or miR mimic, with little optimization required.

It is also within the contemplated scope of the present disclosure that the addition of a targeting agent may also improve the specificity of delivery of QTsome ™ lipid nanoparticle formulations to cancer cell, such as NSCLC cells. One non-limiting example of such additional agent can be the targeting of epidermal growth factor receptor with cetuximab.

Example 9

Figures 26A, 26B:
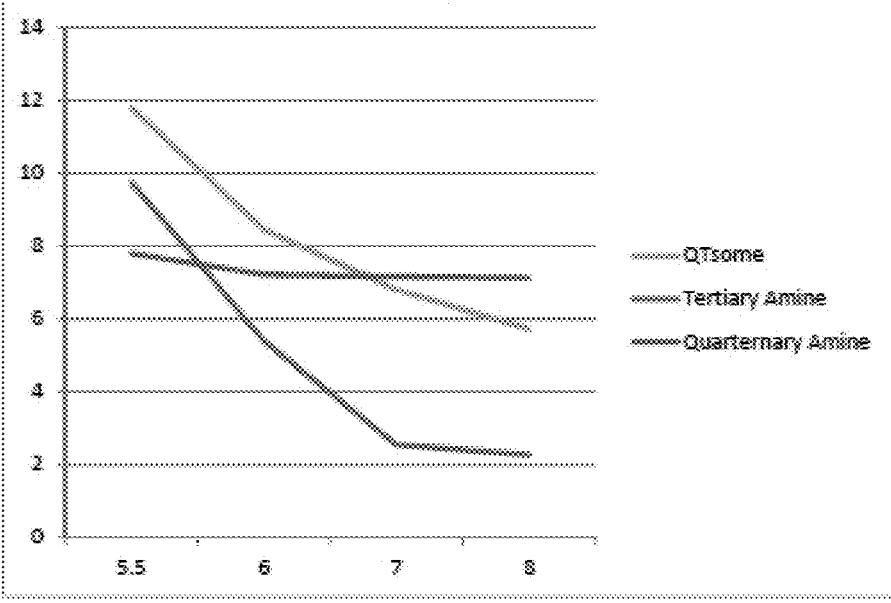
FIG. 26A is a table showing the zeta potential without an oligonucleotide for: tertiary amine, quaternary amine, and a QTsome™ lipid nanoparticle formulation.
FIG. 26B is a graph showing the zeta potential without an oligonucleotide for: tertiary amine, quaternary amine, and a QTsome™ lipid nanoparticle formulation.

FIG. 26A is a table showing the zeta potential without an oligonucleotide for: tertiary amine, quaternary amine, and a QTsome™ lipid nanoparticle formulation.

FIG. 26B is a graph showing the zeta potential without an oligonucleotide for: tertiary amine, quaternary amine, and a QTsome™ lipid nanoparticle formulation.

Example 10

Figures 27A, 27B:
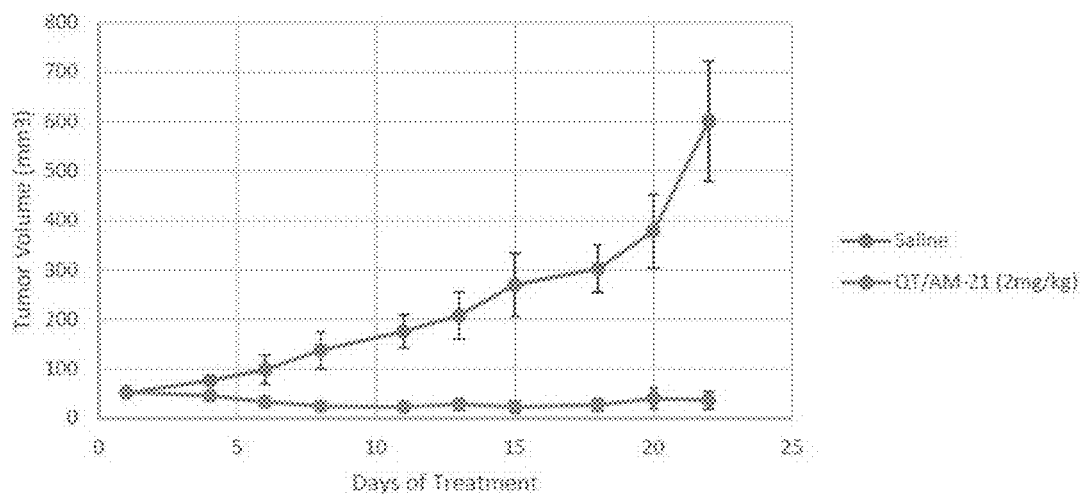
FIG. 27A is a table showing tumor volume ($mm^3$) over a course of days for treatment with saline and QT/AM-21 (2 mg/kg) in an A549 xenograft model.
FIG. 27B is a graph showing tumor volume ($mm^3$) over a course of days for saline and QT/AM-21 (2 mg/kg) treatment in an A549 xenograft model.

FIG. 27A is a table showing tumor volume ($mm^3$) over a course of days for saline and AT/AM-21 (2 mg/kg).

FIG. 27B is a graph showing tumor volume ($mm^3$) over a course of days for saline and AT/AM-21 (2 mg/kg).

Example 11

Figures 28A, 28B:
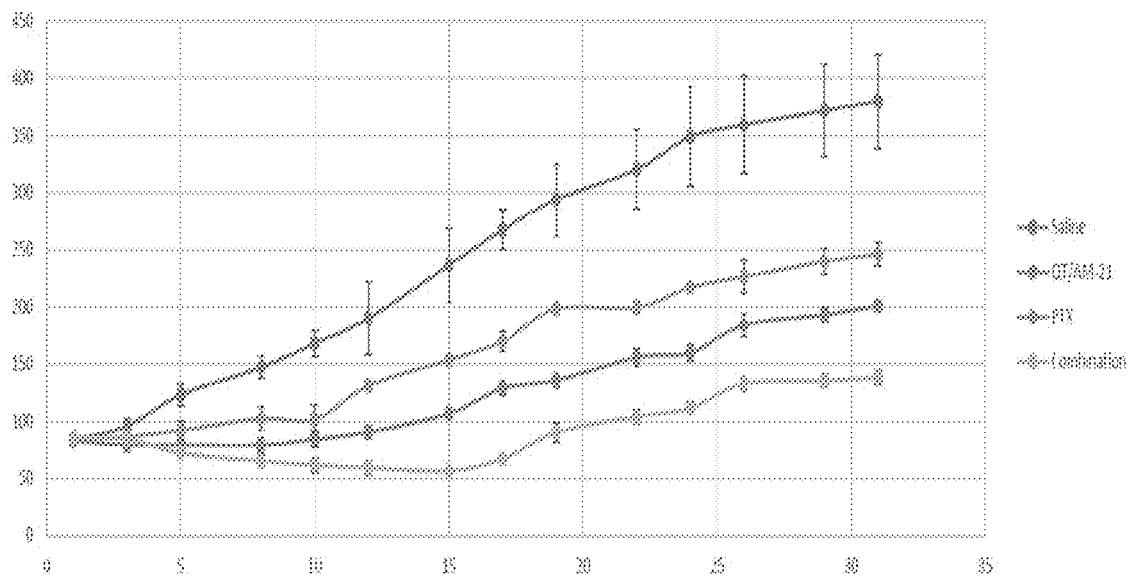
FIG. 28A is a table showing tumor volume ($mm^3$) over a course of days for saline and QT/AM-21 (2 mg/kg), PTX, and a combination of QT/AM-21+PTX treatment in an A549 xenograft model.
FIG. 28B is a graph showing tumor volume ($mm^3$) over a course of days for saline and QT/AM-21 (2 mg/kg), PTX, and a combination of QT/AM-21+PTX treatment in an A549 xenograft model.

FIG. 28A is a table showing tumor volume ($mm^3$) over a course of days for saline and QT/AM-21 (2 mg/kg), PTX, and a combination of QT/AM-21+PTX.

FIG. 28B is a graph showing tumor volume ($mm^3$) over a course of days for saline and QT/AM-21 (2 mg/kg), PTX, and a combination of QT/AM-21+PTX.

Example 12

In certain embodiments, the methods provided herein comprise at least one additional therapy. The at least one additional therapy may comprise a chemotherapeutic agent and/or radiation therapy. The chemotherapeutic agent may be selected from 5-fluorouracil, gemcitabine, doxorubicine, mitomycin c, sorafenib, etoposide, carboplatin, epirubicin, irinotecan and oxaliplatin. The at least one additional therapy may be administered at the same time, less frequently, or more frequently than administration of a composition provided herein.

In any of the methods provided herein, the composition may be administered once per day, once per week, once per two weeks, once per three weeks, or once per four weeks.

In any of the methods provided herein, administering results in reduction of tumor size, and/or reduction of tumor number. In any of the methods provided herein, the administering prevents an increase in tumor size and/or an increase in tumor number. The administering may prevent, stop or slow metastatic progression. The administering may extend the overall survival time of the subject. The administering may extend progression-free survival of the subject.

Certain embodiments of the formulations and methods disclosed herein are defined in the above examples. It should be understood that these examples, while indicating particular embodiments of the invention, are given by way of illustration only. From the above discussion and these examples, one skilled in the art can ascertain the essential characteristics of this disclosure, and without departing from the spirit and scope thereof, can make various changes and modifications to adapt the compositions and methods described herein to various usages and conditions. Various changes may be made and equivalents may be substituted for elements thereof without departing from the essential scope of the disclosure. In addition, many modifications may be made to adapt a particular situation or material to the teachings of the disclosure without departing from the essential scope thereof.

What is claimed is:

1. A method of inhibiting miRNA activity in vitro in a cell from a subject or in vivo to a cell in a subject, comprising:
introducing an inhibitor composition to a location in vitro or in vivo where miRNA activity exists,
wherein the composition comprises at least one oligonucleotide encapsulated in a lipid nanoparticle;
the lipid nanoparticle being comprised of a combination of permanently ionized quaternary amine-cationic lipids and conditionally ionized tertiary amine-cationic lipids; the lipid nanoparticle having a formulation comprising at least:
quaternary amine 1,2-dioleoyl-3-dimethylammonium-propane (DOTAP);
tertiary amine 1,2-dioeyloxy-N,N-dimethyl-3-aminopropane (DODMA);
neutral lipid 1,2-dioleoyl-sn-glycero-3-phosphocholine (DOPC);
helper lipid cholesterol (CHOL); and,
PEGylating agent N-(carbonyl-methoxypolyethylenegly-col 2000)-1,2-dipalmitoyl-sn-glycero-3-phosphoethanolamine (DPPE-PEG),
wherein DOTAP and DODMA each constitute 40 mol percent of the total amount of lipids in the composition, or
wherein the lipids in the composition consist of DOTAP, DODMA, DOPC, CHOL, and PEG-DPPE present in respective molar ratios of 15:25:36:20:4; and,
inhibiting miRNA activity in vitro or in vivo.

2. The method of claim 1, wherein the oligonucleotide comprises one of compounds 101-119, having SEQ ID NOs. 4-22, respectively.

3. The method of claim 1, wherein the oligonucleotide is a synthetic oligonucleotide.

4. The method of claim 1, wherein the miRNA is miR-21.

5. The method of claim 1, wherein the oligonucleotide is an anti-miR-21 oligonucleotide.

6. The method of claim 1, wherein the oligonucleotide comprises an anti-miR-21 oligonucleotide selected from the group consisting of SEQ ID NO: 1, 2, 3, 4, 5, 6, 7, 8, 9, 10, 11, 12, 13, 14, 15, 16, 17, 18, 19, 20, 21, 22, 23, 23, 24, 25, 26, 27 and 28.

7. The method of claim 1, wherein the oligonucleotide is an anti-miR-21 oligonucleotide that comprises compound 116 having SEQ ID NO:19, or compound 117 having SEQ ID NO:20.

8. The method of claim 1, wherein the oligonucleotide is an anti-miR-21 oligonucleotide having SEQ ID NO:3.

9. The method of claim 1, wherein the lipid nanoparticles are coformulated with one or more peptides selected from the group consisting of gramicidin A, B, C, D, and S; HA2; JTS-1; proteinase K (PrK); trichorovin-Xlla (TV-Xlla); rabies virus glycoprotein (RVG); interleukin-1 ~; HIV-Tat; herpes simplex virus (HSV), and VP22 protein.

10. The method of claim 1, wherein inhibiting miRNA activity comprises lowering the activity of the miRNA in vivo in a subject, by contacting a biological sample expressing miR-21 therein with the inhibitor composition.

11. The method of claim 10 wherein the biological sample is a cancer cell which over-expresses miR-21 relative to non-tumor cells.

12. The method of claim 1, wherein the miRNA activity is measured as the expression levels of miR-21 target genes selected from: ANKRD46, PTEN, PDCD4, DDAH1, RECK and/or TIMP3.

13. The method of claim 1, further including administering at least one additional therapeutic agent to the subject prior to, simultaneous with, or subsequent to, administration of the inhibitor composition.

14. The method of claim 13, wherein the therapeutic agent comprises paclitaxel.

15. The method of claim 1, wherein the subject has one or more of lung cancer, ovarian cancer, breast cancer, or a glioma.

16. The method of claim 1, wherein the tertiary amine-cationic lipids further include one or more of: DODAP, DC-CHOL, N,N-dimethylhexadecylamine, or combinations thereof; and, the quaternary amine-cationic lipids further include one or more of: DOTMA, DDAB, or combinations thereof.

17. A method of treating a condition characterized by over-expression of miRNA comprising,
administering an inhibitor composition to a subject at a concentration sufficient to inhibit the action of the miRNA;
wherein the composition comprises at least one oligonucleotide capable of inhibiting activity of the miRNA encapsulated in the lipid nanoparticle of claim 1.

* * * * *

SEQUENCE LISTING

<160> NUMBER OF SEQ ID NOS: 28

<210> SEQ ID NO 1
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(22)
<223> OTHER INFORMATION: 2'O-methylated modified base
<220> FEATURE:
<221> NAME/KEY: misc_feature
<222> LOCATION: (19)..(22)
<223> OTHER INFORMATION: Phosphorothioate linkage

<400> SEQUENCE: 1
ucaacaucag ucugauaagc ua                                              22

<210> SEQ ID NO 2
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(22)
<223> OTHER INFORMATION: 2'O-methylated modified base
<220> FEATURE:
<221> NAME/KEY: misc_feature
<222> LOCATION: (19)..(22)
<223> OTHER INFORMATION: Phosphorothioate linkage
<220> FEATURE:
<221> NAME/KEY: modified_base
<222> LOCATION: (22)..(22)
<223> OTHER INFORMATION: a-CHOL

<400> SEQUENCE: 2
ucaacaucag ucugauaagc ua                                              22

<210> SEQ ID NO 3
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: misc_feature
<222> LOCATION: (19)..(22)
<223> OTHER INFORMATION: Phosphorothioate linkage

<400> SEQUENCE: 3
ucaacaucag ucugauaagc ua                                              22

<210> SEQ ID NO 4

```
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(22)
<223> OTHER INFORMATION: Phosphorothioate linkage
<220> FEATURE:
<221> NAME/KEY: modified_base
<222> LOCATION: (1)..(2)
<223> OTHER INFORMATION: Locked nucleic acid
<220> FEATURE:
<221> NAME/KEY: modified_base
<222> LOCATION: (8)..(8)
<223> OTHER INFORMATION: Locked nucleic acid
<220> FEATURE:
<221> NAME/KEY: modified_base
<222> LOCATION: (12)..(12)
<223> OTHER INFORMATION: Locked nucleic acid
<220> FEATURE:
<221> NAME/KEY: modified_base
<222> LOCATION: (16)..(16)
<223> OTHER INFORMATION: Locked nucleic acid
<220> FEATURE:
<221> NAME/KEY: modified_base
<222> LOCATION: (20)..(22)
<223> OTHER INFORMATION: Locked nucleic acid

<400> SEQUENCE: 4
tcaacatcag tctgataagc ta                                             22

<210> SEQ ID NO 5
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(15)
<223> OTHER INFORMATION: Phosphorothioate linkage
<220> FEATURE:
<221> NAME/KEY: modified_base
<222> LOCATION: (1)..(1)
<223> OTHER INFORMATION: Locked nucleic acid
<220> FEATURE:
<221> NAME/KEY: modified_base
<222> LOCATION: (3)..(3)
<223> OTHER INFORMATION: Locked nucleic acid
<220> FEATURE:
<221> NAME/KEY: modified_base
<222> LOCATION: (6)..(7)
<223> OTHER INFORMATION: Locked nucleic acid
<220> FEATURE:
<221> NAME/KEY: modified_base
<222> LOCATION: (10)..(10)
<223> OTHER INFORMATION: Locked nucleic acid
<220> FEATURE:
<221> NAME/KEY: modified_base
<222> LOCATION: (12)..(12)
<223> OTHER INFORMATION: Locked nucleic acid
<220> FEATURE:
<221> NAME/KEY: modified_base
<222> LOCATION: (14)..(15)
<223> OTHER INFORMATION: Locked nucleic acid

<400> SEQUENCE: 5
cagtctgata agcta                                                     15

<210> SEQ ID NO 6
<211> LENGTH: 8
```

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(8)
<223> OTHER INFORMATION: Phosphorothioate linkage
<220> FEATURE:
<221> NAME/KEY: modified_base
<222> LOCATION: (1)..(8)
<223> OTHER INFORMATION: Locked nucleic acid

<400> SEQUENCE: 6 gataagct                                                                        8

<210> SEQ ID NO 7
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(16)
<223> OTHER INFORMATION: Phosphorothioate linkage
<220> FEATURE:
<221> NAME/KEY: modified_base
<222> LOCATION: (1)..(2)
<223> OTHER INFORMATION: Locked nucleic acid
<220> FEATURE:
<221> NAME/KEY: modified_base
<222> LOCATION: (6)..(6)
<223> OTHER INFORMATION: Locked nucleic acid
<220> FEATURE:
<221> NAME/KEY: modified_base
<222> LOCATION: (10)..(10)
<223> OTHER INFORMATION: Locked nucleic acid
<220> FEATURE:
<221> NAME/KEY: modified_base
<222> LOCATION: (12)..(13)
<223> OTHER INFORMATION: Locked nucleic acid
<220> FEATURE:
<221> NAME/KEY: modified_base
<222> LOCATION: (15)..(16)
<223> OTHER INFORMATION: Locked nucleic acid

<400> SEQUENCE: 7
tcagtctgat aagcta                                                              16

<210> SEQ ID NO 8
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(6)
<223> OTHER INFORMATION: Phosphorothioate linkage
<220> FEATURE:
<221> NAME/KEY: modified_base
<222> LOCATION: (1)..(2)
<223> OTHER INFORMATION: Locked nucleic acid
<220> FEATURE:
<221> NAME/KEY: modified_base
<222> LOCATION: (6)..(6)
<223> OTHER INFORMATION: Locked nucleic acid
<220> FEATURE:
<221> NAME/KEY: misc_feature
<222> LOCATION: (7)..(10)
<223> OTHER INFORMATION: Phosphorothioate linkage
```

```
<220> FEATURE:
<221> NAME/KEY: modified_base
<222> LOCATION: (10)..(10)
<223> OTHER INFORMATION: Locked nucleic acid
<220> FEATURE:
<221> NAME/KEY: misc_feature
<222> LOCATION: (11)..(12)
<223> OTHER INFORMATION: Phosphorothioate linkage
<220> FEATURE:
<221> NAME/KEY: modified_base
<222> LOCATION: (12)..(13)
<223> OTHER INFORMATION: Locked nucleic acid
<220> FEATURE:
<221> NAME/KEY: misc_feature
<222> LOCATION: (14)..(16)
<223> OTHER INFORMATION: Phosphorothioate linkage
<220> FEATURE:
<221> NAME/KEY: modified_base
<222> LOCATION: (15)..(16)
<223> OTHER INFORMATION: Locked nucleic acid

<400> SEQUENCE: 8
tcagtctgat aagcta                                                       16

<210> SEQ ID NO 9
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(15)
<223> OTHER INFORMATION: Phosphorothioate linkage
<220> FEATURE:
<221> NAME/KEY: modified_base
<222> LOCATION: (1)..(2)
<223> OTHER INFORMATION: Locked nucleic acid
<220> FEATURE:
<221> NAME/KEY: modified_base
<222> LOCATION: (6)..(6)
<223> OTHER INFORMATION: Locked nucleic acid
<220> FEATURE:
<221> NAME/KEY: modified_base
<222> LOCATION: (10)..(10)
<223> OTHER INFORMATION: Locked nucleic acid
<220> FEATURE:
<221> NAME/KEY: modified_base
<222> LOCATION: (12)..(12)
<223> OTHER INFORMATION: Locked nucleic acid
<220> FEATURE:
<221> NAME/KEY: modified_base
<222> LOCATION: (14)..(15)
<223> OTHER INFORMATION: Locked nucleic acid

<400> SEQUENCE: 9
tcagtctgat aagct                                                        15

<210> SEQ ID NO 10
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(10)
<223> OTHER INFORMATION: Phosphorothioate linkage
<220> FEATURE:
<221> NAME/KEY: modified_base
<222> LOCATION: (1)..(2)
<223> OTHER INFORMATION: Locked nucleic acid
<220> FEATURE:
```

<221> NAME/KEY: modified_base
<222> LOCATION: (6)..(6)
<223> OTHER INFORMATION: Locked nucleic acid
<220> FEATURE:
<221> NAME/KEY: modified_base
<222> LOCATION: (10)..(10)
<223> OTHER INFORMATION: Locked nucleic acid
<220> FEATURE:
<221> NAME/KEY: misc_feature
<222> LOCATION: (11)..(12)
<223> OTHER INFORMATION: Phosphorothioate linkage
<220> FEATURE:
<221> NAME/KEY: modified_base
<222> LOCATION: (12)..(12)
<223> OTHER INFORMATION: Locked nucleic acid
<220> FEATURE:
<221> NAME/KEY: misc_feature
<222> LOCATION: (13)..(15)
<223> OTHER INFORMATION: Phosphorothioate linkage
<220> FEATURE:
<221> NAME/KEY: modified_base
<222> LOCATION: (14)..(15)
<223> OTHER INFORMATION: Locked nucleic acid

<400> SEQUENCE: 10
tcagtctgat aagct                                                     15

<210> SEQ ID NO 11
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(16)
<223> OTHER INFORMATION: Phosphorothioate linkage
<220> FEATURE:
<221> NAME/KEY: modified_base
<222> LOCATION: (1)..(2)
<223> OTHER INFORMATION: Locked nucleic acid
<220> FEATURE:
<221> NAME/KEY: modified_base
<222> LOCATION: (6)..(6)
<223> OTHER INFORMATION: Locked nucleic acid
<220> FEATURE:
<221> NAME/KEY: modified_base
<222> LOCATION: (10)..(10)
<223> OTHER INFORMATION: Locked nucleic acid
<220> FEATURE:
<221> NAME/KEY: modified_base
<222> LOCATION: (13)..(13)
<223> OTHER INFORMATION: Locked nucleic acid
<220> FEATURE:
<221> NAME/KEY: modified_base
<222> LOCATION: (15)..(16)
<223> OTHER INFORMATION: Locked nucleic acid

<400> SEQUENCE: 11
tcagtctgat aagcta                                                    16

<210> SEQ ID NO 12
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(10)
<223> OTHER INFORMATION: Phosphorothioate linkage
<220> FEATURE:
<221> NAME/KEY: modified_base

```
<222> LOCATION: (1)..(2)
<223> OTHER INFORMATION: Locked nucleic acid
<220> FEATURE:
<221> NAME/KEY: modified_base
<222> LOCATION: (6)..(6)
<223> OTHER INFORMATION: Locked nucleic acid
<220> FEATURE:
<221> NAME/KEY: modified_base
<222> LOCATION: (10)..(10)
<223> OTHER INFORMATION: Locked nucleic acid
<220> FEATURE:
<221> NAME/KEY: misc_feature
<222> LOCATION: (11)..(13)
<223> OTHER INFORMATION: Phosphorothioate linkage
<220> FEATURE:
<221> NAME/KEY: modified_base
<222> LOCATION: (13)..(13)
<223> OTHER INFORMATION: Locked nucleic acid
<220> FEATURE:
<221> NAME/KEY: misc_feature
<222> LOCATION: (14)..(16)
<223> OTHER INFORMATION: Phosphorothioate linkage
<220> FEATURE:
<221> NAME/KEY: modified_base
<222> LOCATION: (15)..(16)
<223> OTHER INFORMATION: Locked nucleic acid

<400> SEQUENCE: 12
tcagtctgat aagcta                                               16

<210> SEQ ID NO 13
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(10)
<223> OTHER INFORMATION: Phosphorothioate linkage
<220> FEATURE:
<221> NAME/KEY: modified_base
<222> LOCATION: (1)..(2)
<223> OTHER INFORMATION: Locked nucleic acid
<220> FEATURE:
<221> NAME/KEY: modified_base
<222> LOCATION: (6)..(6)
<223> OTHER INFORMATION: Locked nucleic acid
<220> FEATURE:
<221> NAME/KEY: modified_base
<222> LOCATION: (10)..(10)
<223> OTHER INFORMATION: Locked nucleic acid
<220> FEATURE:
<221> NAME/KEY: misc_feature
<222> LOCATION: (11)..(13)
<223> OTHER INFORMATION: Phosphorothioate linkage
<220> FEATURE:
<221> NAME/KEY: modified_base
<222> LOCATION: (13)..(16)
<223> OTHER INFORMATION: Locked nucleic acid
<220> FEATURE:
<221> NAME/KEY: misc_feature
<222> LOCATION: (14)..(16)
<223> OTHER INFORMATION: Phosphorothioate linkage

<400> SEQUENCE: 13
tcagtctgat aagcta                                               16

<210> SEQ ID NO 14
<211> LENGTH: 16
<212> TYPE: DNA
<213> ORGANISM: Artificial Sequence
<220> FEATURE:
<223> OTHER INFORMATION: Description of Artificial Sequence: Synthetic
```

```
        oligonucleotide
<220> FEATURE:
<221> NAME/KEY: misc_feature
<222> LOCATION: (1)..(16)
<223> OTHER INFORMATION: Phosphorothioate linkage
<220> FEATURE:
<221> NAME/KEY: modified_base
<222> LOCATION: (1)..(2)
<223> OTHER INFORMATION: Locked nucleic acid
<220> FEATURE:
<221> NAME/KEY: modified_base
<222> LOCATION: (6)..(6)
<223> OTHER INFORMATION: Locked nucleic acid
<220> FEATURE:
<221> NAME/KEY: modified_base
<222> LOCATION: (10)..(10)
<223> OTHER INFORMATION: Locked nucleic acid
<220> FEATURE:
<221> NAME/KEY: modified_base
<222> LOCATION: (13)..(13)
<223> OTHER INFORMATION: Locked nucleic acid
<220> FEATURE:
<221> NAME/KEY: modified_base
<222> LOCATION: (15)..(16)
<223> OTHER INFORMATION: Locked nucleic acid

<400> SEQUENCE: 14
tcagtctgat aagcta                                                        16

<210> SEQ ID NO 15
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(15)
<223> OTHER INFORMATION: Phosphorothioate linkage
<220> FEATURE:
<221> NAME/KEY: modified_base
<222> LOCATION: (1)..(2)
<223> OTHER INFORMATION: Locked nucleic acid
<220> FEATURE:
<221> NAME/KEY: modified_base
<222> LOCATION: (6)..(6)
<223> OTHER INFORMATION: Locked nucleic acid
<220> FEATURE:
<221> NAME/KEY: modified_base
<222> LOCATION: (9)..(9)
<223> OTHER INFORMATION: 2'O-methylated modified base
<220> FEATURE:
<221> NAME/KEY: modified_base
<222> LOCATION: (10)..(10)
<223> OTHER INFORMATION: Locked nucleic acid
<220> FEATURE:
<221> NAME/KEY: modified_base
<222> LOCATION: (11)..(11)
<223> OTHER INFORMATION: 2'O-methylated modified base
<220> FEATURE:
<221> NAME/KEY: modified_base
<222> LOCATION: (12)..(13)
<223> OTHER INFORMATION: Locked nucleic acid
<220> FEATURE:
<221> NAME/KEY: modified_base
<222> LOCATION: (14)..(14)
<223> OTHER INFORMATION: 2'O-methylated modified base
<220> FEATURE:
<221> NAME/KEY: modified_base
<222> LOCATION: (15)..(15)
<223> OTHER INFORMATION: Locked nucleic acid

<400> SEQUENCE: 15
tcagtctgat aagct                                                         15
```

-continued

```
<210> SEQ ID NO 16
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: misc_feature
<222> LOCATION: (1)..(16)
<223> OTHER INFORMATION: Phosphorothioate linkage
<220> FEATURE:
<221> NAME/KEY: modified_base
<222> LOCATION: (1)..(2)
<223> OTHER INFORMATION: Locked nucleic acid
<220> FEATURE:
<221> NAME/KEY: modified_base
<222> LOCATION: (3)..(5)
<223> OTHER INFORMATION: 2'O-methylated modified base
<220> FEATURE:
<221> NAME/KEY: modified_base
<222> LOCATION: (6)..(6)
<223> OTHER INFORMATION: Locked nucleic acid
<220> FEATURE:
<221> NAME/KEY: modified_base
<222> LOCATION: (7)..(9)
<223> OTHER INFORMATION: 2'O-methylated modified base
<220> FEATURE:
<221> NAME/KEY: modified_base
<222> LOCATION: (10)..(10)
<223> OTHER INFORMATION: Locked nucleic acid
<220> FEATURE:
<221> NAME/KEY: modified_base
<222> LOCATION: (11)..(11)
<223> OTHER INFORMATION: 2'O-methylated modified base
<220> FEATURE:
<221> NAME/KEY: modified_base
<222> LOCATION: (12)..(13)
<223> OTHER INFORMATION: Locked nucleic acid
<220> FEATURE:
<221> NAME/KEY: modified_base
<222> LOCATION: (14)..(14)
<223> OTHER INFORMATION: 2'O-methylated modified base
<220> FEATURE:
<221> NAME/KEY: modified_base
<222> LOCATION: (15)..(16)
<223> OTHER INFORMATION: Locked nucleic acid

<400> SEQUENCE: 16
tcagucugat aagcta                                                          16

<210> SEQ ID NO 17
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(15)
<223> OTHER INFORMATION: Phosphorothioate linkage
<220> FEATURE:
<221> NAME/KEY: modified_base
<222> LOCATION: (1)..(2)
<223> OTHER INFORMATION: Locked nucleic acid
<220> FEATURE:
<221> NAME/KEY: modified_base
<222> LOCATION: (3)..(5)
<223> OTHER INFORMATION: 2'O-methylated modified base
<220> FEATURE:
<221> NAME/KEY: modified_base
<222> LOCATION: (6)..(6)
```

```
<223> OTHER INFORMATION: Locked nucleic acid
<220> FEATURE:
<221> NAME/KEY: modified_base
<222> LOCATION: (7)..(9)
<223> OTHER INFORMATION: 2'O-methylated modified base
<220> FEATURE:
<221> NAME/KEY: modified_base
<222> LOCATION: (10)..(10)
<223> OTHER INFORMATION: Locked nucleic acid
<220> FEATURE:
<221> NAME/KEY: modified_base
<222> LOCATION: (11)..(11)
<223> OTHER INFORMATION: 2'O-methylated modified base
<220> FEATURE:
<221> NAME/KEY: modified_base
<222> LOCATION: (12)..(13)
<223> OTHER INFORMATION: Locked nucleic acid
<220> FEATURE:
<221> NAME/KEY: modified_base
<222> LOCATION: (14)..(14)
<223> OTHER INFORMATION: 2'O-methylated modified base
<220> FEATURE:
<221> NAME/KEY: modified_base
<222> LOCATION: (15)..(15)
<223> OTHER INFORMATION: Locked nucleic acid

<400> SEQUENCE: 17
tcagtctgat aagct                                              15

<210> SEQ ID NO 18
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(6)
<223> OTHER INFORMATION: Phosphorothioate linkage
<220> FEATURE:
<221> NAME/KEY: modified_base
<222> LOCATION: (1)..(2)
<223> OTHER INFORMATION: Locked nucleic acid
<220> FEATURE:
<221> NAME/KEY: modified_base
<222> LOCATION: (5)..(5)
<223> OTHER INFORMATION: 2'O-methylated modified base
<220> FEATURE:
<221> NAME/KEY: modified_base
<222> LOCATION: (6)..(6)
<223> OTHER INFORMATION: Locked nucleic acid
<220> FEATURE:
<221> NAME/KEY: misc_feature
<222> LOCATION: (7)..(10)
<223> OTHER INFORMATION: Phosphorothioate linkage
<220> FEATURE:
<221> NAME/KEY: modified_base
<222> LOCATION: (7)..(7)
<223> OTHER INFORMATION: 2'O-methylated modified base
<220> FEATURE:
<221> NAME/KEY: modified_base
<222> LOCATION: (10)..(10)
<223> OTHER INFORMATION: Locked nucleic acid
<220> FEATURE:
<221> NAME/KEY: misc_feature
<222> LOCATION: (11)..(12)
<223> OTHER INFORMATION: Phosphorothioate linkage
<220> FEATURE:
<221> NAME/KEY: modified_base
<222> LOCATION: (12)..(13)
<223> OTHER INFORMATION: Locked nucleic acid
<220> FEATURE:
<221> NAME/KEY: misc_feature
<222> LOCATION: (14)..(16)
<223> OTHER INFORMATION: Phosphorothioate linkage
<220> FEATURE:
```

```
<221> NAME/KEY: modified_base
<222> LOCATION: (14)..(14)
<223> OTHER INFORMATION: 2'O-methylated modified base
<220> FEATURE:
<221> NAME/KEY: modified_base
<222> LOCATION: (15)..(16)
<223> OTHER INFORMATION: Locked nucleic acid

<400> SEQUENCE: 18
tcagtctgat aagcta                                                          16

<210> SEQ ID NO 19
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(6)
<223> OTHER INFORMATION: Phosphorothioate linkage
<220> FEATURE:
<221> NAME/KEY: modified_base
<222> LOCATION: (1)..(1)
<223> OTHER INFORMATION: Locked nucleic acid
<220> FEATURE:
<221> NAME/KEY: misc_feature
<222> LOCATION: (8)..(11)
<223> OTHER INFORMATION: Phosphorothioate linkage
<220> FEATURE:
<221> NAME/KEY: modified_base
<222> LOCATION: (10)..(16)
<223> OTHER INFORMATION: Locked nucleic acid
<220> FEATURE:
<221> NAME/KEY: misc_feature
<222> LOCATION: (13)..(16)
<223> OTHER INFORMATION: Phosphorothioate linkage

<400> SEQUENCE: 19
tcagtctgat aagcta                                                          16

<210> SEQ ID NO 20
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(6)
<223> OTHER INFORMATION: Phosphorothioate linkage
<220> FEATURE:
<221> NAME/KEY: modified_base
<222> LOCATION: (1)..(1)
<223> OTHER INFORMATION: Locked nucleic acid
<220> FEATURE:
<221> NAME/KEY: misc_feature
<222> LOCATION: (8)..(11)
<223> OTHER INFORMATION: Phosphorothioate linkage
<220> FEATURE:
<221> NAME/KEY: modified_base
<222> LOCATION: (9)..(15)
<223> OTHER INFORMATION: Locked nucleic acid
<220> FEATURE:
<221> NAME/KEY: misc_feature
<222> LOCATION: (13)..(15)
<223> OTHER INFORMATION: Phosphorothioate linkage

<400> SEQUENCE: 20
tcagtctgat aagct                                                           15
```

```
<210> SEQ ID NO 21
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(6)
<223> OTHER INFORMATION: Phosphorothioate linkage
<220> FEATURE:
<221> NAME/KEY: modified_base
<222> LOCATION: (1)..(1)
<223> OTHER INFORMATION: Locked nucleic acid
<220> FEATURE:
<221> NAME/KEY: misc_feature
<222> LOCATION: (8)..(10)
<223> OTHER INFORMATION: Phosphorothioate linkage
<220> FEATURE:
<221> NAME/KEY: modified_base
<222> LOCATION: (9)..(16)
<223> OTHER INFORMATION: Locked nucleic acid
<220> FEATURE:
<221> NAME/KEY: misc_feature
<222> LOCATION: (13)..(16)
<223> OTHER INFORMATION: Phosphorothioate linkage

<400> SEQUENCE: 21
tcagtctgat aagcta                                                       16

<210> SEQ ID NO 22
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(10)
<223> OTHER INFORMATION: Phosphorothioate linkage
<220> FEATURE:
<221> NAME/KEY: modified_base
<222> LOCATION: (1)..(2)
<223> OTHER INFORMATION: Locked nucleic acid
<220> FEATURE:
<221> NAME/KEY: modified_base
<222> LOCATION: (6)..(6)
<223> OTHER INFORMATION: Locked nucleic acid
<220> FEATURE:
<221> NAME/KEY: modified_base
<222> LOCATION: (9)..(10)
<223> OTHER INFORMATION: Locked nucleic acid
<220> FEATURE:
<221> NAME/KEY: misc_feature
<222> LOCATION: (11)..(13)
<223> OTHER INFORMATION: Phosphorothioate linkage
<220> FEATURE:
<221> NAME/KEY: modified_base
<222> LOCATION: (13)..(15)
<223> OTHER INFORMATION: Locked nucleic acid
<220> FEATURE:
<221> NAME/KEY: misc_feature
<222> LOCATION: (14)..(15)
<223> OTHER INFORMATION: Phosphorothioate linkage

<400> SEQUENCE: 22
tcagtctgat aagct                                                        15

<210> SEQ ID NO 23
<211> LENGTH: 22
<212> TYPE: DNA
<213> ORGANISM: Artificial Sequence
<220> FEATURE:
```

<223> OTHER INFORMATION: Description of Artificial Sequence: Synthetic
      oligonucleotide
<220> FEATURE:
<221> NAME/KEY: misc_feature
<222> LOCATION: (1)..(9)
<223> OTHER INFORMATION: Phosphorothioate linkage
<220> FEATURE:
<221> NAME/KEY: modified_base
<222> LOCATION: (1)..(22)
<223> OTHER INFORMATION: 2'O-methylated modified base
<220> FEATURE:
<221> NAME/KEY: misc_feature
<222> LOCATION: (19)..(22)
<223> OTHER INFORMATION: Phosphorothioate linkage

<400> SEQUENCE: 23
tcaacatcag tctgataagc ta                                            22

<210> SEQ ID NO 24
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(7)
<223> OTHER INFORMATION: Phosphorothioate linkage
<220> FEATURE:
<221> NAME/KEY: modified_base
<222> LOCATION: (1)..(22)
<223> OTHER INFORMATION: 2'O-methylated modified base
<220> FEATURE:
<221> NAME/KEY: misc_feature
<222> LOCATION: (17)..(22)
<223> OTHER INFORMATION: Phosphorothioate linkage

<400> SEQUENCE: 24
tcaacatcag tctgataagc ta                                            22

<210> SEQ ID NO 25
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(4)
<223> OTHER INFORMATION: Phosphorothioate linkage
<220> FEATURE:
<221> NAME/KEY: modified_base
<222> LOCATION: (1)..(18)
<223> OTHER INFORMATION: 2'O-methylated modified base
<220> FEATURE:
<221> NAME/KEY: misc_feature
<222> LOCATION: (15)..(18)
<223> OTHER INFORMATION: Phosphorothioate linkage

<400> SEQUENCE: 25
catcagtctg ataagcta                                                 18

<210> SEQ ID NO 26
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature

```
<222> LOCATION: (1)..(4)
<223> OTHER INFORMATION: Phosphorothioate linkage
<220> FEATURE:
<221> NAME/KEY: modified_base
<222> LOCATION: (1)..(16)
<223> OTHER INFORMATION: 2'O-methylated modified base
<220> FEATURE:
<221> NAME/KEY: misc_feature
<222> LOCATION: (13)..(16)
<223> OTHER INFORMATION: Phosphorothioate linkage

<400> SEQUENCE: 26
tcagtctgat aagcta                                                 16

<210> SEQ ID NO 27
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(9)
<223> OTHER INFORMATION: Phosphorothioate linkage
<220> FEATURE:
<221> NAME/KEY: modified_base
<222> LOCATION: (1)..(9)
<223> OTHER INFORMATION: 2'O-methylated modified base

<400> SEQUENCE: 27 tgataagct                                                          9

<210> SEQ ID NO 28
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(9)
<223> OTHER INFORMATION: 2'O-methylated modified base

<400> SEQUENCE: 28 tgataagct                                                          9
```